United States Patent
Fraser

(10) Patent No.: US 9,137,020 B1
(45) Date of Patent: *Sep. 15, 2015

(54) AUTHENTICATION METHOD AND SYSTEM

(71) Applicant: Copilot Ventures Fund III LLC, Wilmington, TX (US)

(72) Inventor: Jay Fraser, San Antonio, TX (US)

(73) Assignee: Copilot Ventures Fund III LLC, Wilmington, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/636,293

(22) Filed: Mar. 3, 2015

Related U.S. Application Data

(63) Continuation of application No. 14/157,697, filed on Jan. 17, 2014, now Pat. No. 8,970,828, which is a continuation of application No. 13/206,074, filed on Aug. 9, 2011, now Pat. No. 8,634,066, which is a continuation of application No. 12/427,399, filed on Apr. 21, 2009, now Pat. No. 7,995,196.

(60) Provisional application No. 61/047,326, filed on Apr. 23, 2008.

(51) Int. Cl.
*G06K 9/74* (2006.01)
*H04L 9/32* (2006.01)
*G07D 7/00* (2006.01)
*G07D 7/20* (2006.01)

(52) U.S. Cl.
CPC ............ *H04L 9/3247* (2013.01); *G07D 7/0026* (2013.01); *G07D 7/2033* (2013.01); *H04L 2209/72* (2013.01)

(58) Field of Classification Search
CPC ........... G06K 9/00046; G06K 9/00013; A61B 5/1172; G07D 7/12; G07D 7/122; G07D 7/002; G07D 7/0033; G07D 7/2033; G06T 1/0021; H04N 1/32229; H04N 2201/3235; H04N 2201/3236; H04N 2201/327; B42D 15/0013; B42D 2035/33; B42D 5/00
USPC ................ 356/71; 713/176; 380/201; 726/32
See application file for complete search history.

(56) References Cited

U.S. PATENT DOCUMENTS

| | | | | |
|---|---|---|---|---|
| 5,974,150 A * | 10/1999 | Kaish et al. | | 713/179 |
| 6,975,755 B1 * | 12/2005 | Baumberg | | 382/154 |
| 2009/0008924 A1 * | 1/2009 | Ophey et al. | | 283/85 |

* cited by examiner

Primary Examiner — Tarifur Chowdhury
Assistant Examiner — Md Rahman
(74) Attorney, Agent, or Firm — Steven M. Hoffberg, Esq.; Ostrolenk Faber LLP.

(57) ABSTRACT

A method for authenticating an object, comprising determining a physical dispersion pattern of a set of elements, determining a physical characteristic of the set of elements which is distinct from a physical characteristic producible by a transfer printing technology, determining a digital code associated with the object defining the physical dispersion pattern, and authenticating the object by verifying a correspondence of the digital code with the physical dispersion pattern, and verifying the physical characteristic.

20 Claims, 15 Drawing Sheets

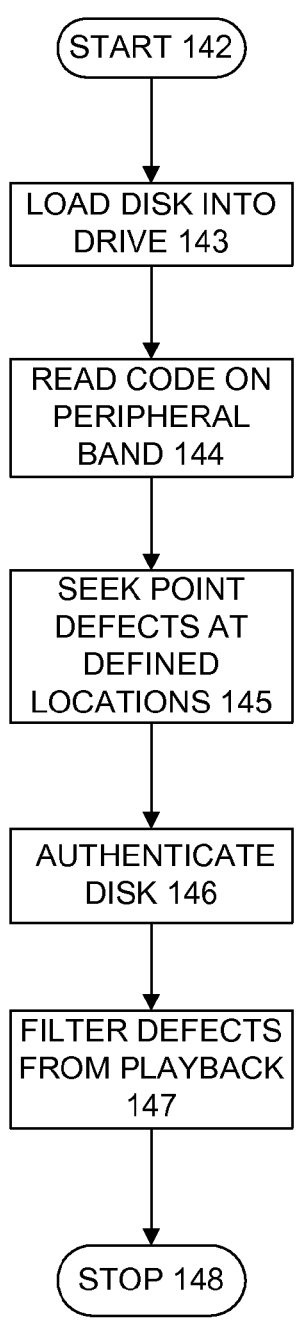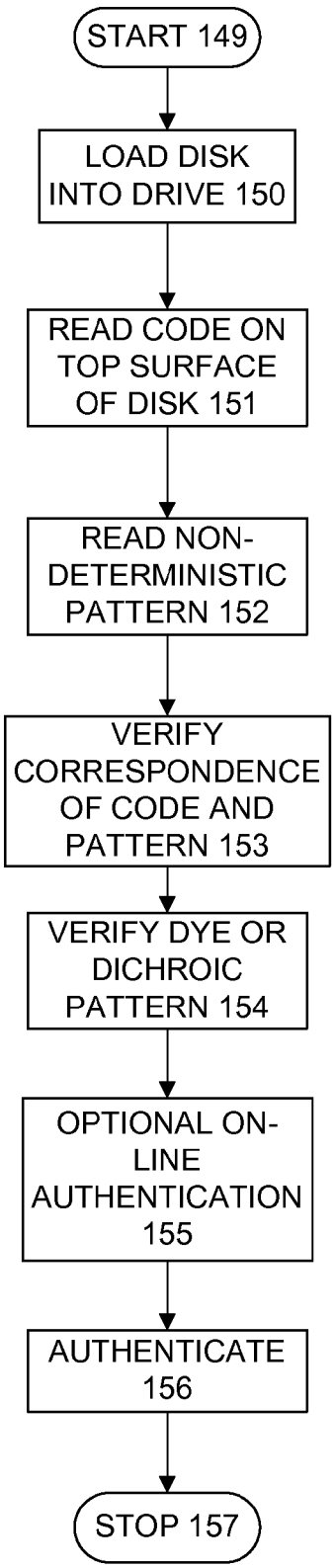
FIG. 14A
FIG. 14B

AUTHENTICATION METHOD AND SYSTEM

CROSS REFERENCE TO RELATED APPLICATIONS

The present application is a Continuation of U.S. patent application Ser. No. 14/157,697, filed Jan. 17, 2014, now U.S. Pat. No. 8,970,828, issued Mar. 3, 2015, which is a Continuation of U.S. patent application Ser. No. 13/206,074, filed Aug. 9, 2011, now U.S. Pat. No. 8,634,066, issued Jan. 21, 2014, which is a continuation of U.S. patent application Ser. No. 12/427,399, filed Apr. 21, 2009, now U.S. Pat. No. 7,995,196, issued Aug. 9, 2011, which claims priority from U.S. Provisional Application No. 61/047,326, filed Apr. 23, 2008, each of which is expressly incorporated herein by reference in its entirety.

FIELD OF THE INVENTION

The present invention relates to the fields of authentication, security, anti-counterfeiting, and cryptography.

BACKGROUND OF THE INVENTION

The issues of authentication and counterfeit deterrence can be important in many contexts. Bills of currency, stock and bond certificates, credit cards, passports, bills of lading, as well as many other legal documents (e.g., deeds, wills, etc.) all must be reliably authentic to be useful. Authentication and avoidance of counterfeiting can also be important in many less obvious contexts. For example, improved verification/counterfeiting prevention mechanisms would be very useful in, for example, verifying the contents of shipping containers, quickly identifying individuals with particular health or criminal histories, etc. Counterfeit products are, by definition, unauthorized copies of a product, its packaging, labeling, and/or its logo(s). Attractive targets for counterfeiters are items with significant brand equity or symbolic value, where the cost of production is below the market value.

In the commercial manufacturing world, it is not uncommon for counterfeit or otherwise unauthorized goods to be manufactured, distributed, and sold in direct competition with authentic goods. Counterfeiting has reached epidemic proportions worldwide, especially in the area of consumer goods including goods made from fabric, plastic, leather, metal, or combinations thereof such as clothing, handbags and wallets, perfumes, and other consumer goods. Electronics and software products are also particular targets of counterfeiters, who appropriate the value of trademarks or copyrights without license. Since costs savings based on decreased incremental cost of production (exclusive of license fees) is not a necessary element in the counterfeiting scheme, the counterfeit articles may be of apparently high quality and closely resemble authentic articles. Indeed, counterfeit articles can so closely resemble genuine goods that consumers readily confuse the counterfeit articles with the authentic articles. In other circumstances, the manufacturer segments the world market for different sales and distribution practices, so that the "counterfeit" goods may be essentially identical to authorized goods. Further, in many instances, a manufacturer produces goods under license from an intellectual property owner, and thus sales outside the terms of the license agreement are also "counterfeit".

Counterfeit deterrence and self-authentication issues are an integral component in the modern world, where information is transmitted with lightening-like speed. Stock and bond certificates, bills of currency, credit cards, bills of lading, passports, and other legal documents such as deeds and wills must all be determined to be reliably authentic if they are to serve any purpose. Authentication and the avoidance of counterfeiting can be of vital import in the contexts of improving product verification and counterfeit deterrence, or in quickly identifying individuals with certain health or criminal histories, or in determining the contents of shipping containers. The most obvious choices for the would-be counterfeiter are those items which have a very low cost of production, yet high financial returns, such as articles with designer logos, brand names, and trademarks. Since counterfeiting is essentially the unauthorized copying of these types of products, the market and incentive to counterfeit are great.

In the United States, crime and fraud prevention is a massive, multi-billion dollar market. New methods of marking authentic goods and anti-counterfeiting technology are at the forefront of this business. The everyday marking of day to day products such as jeans, CDs and software, audio and videotapes, and cosmetics can prevent widespread counterfeiting and the import of fraudulent copies unauthorized by the legitimate producers.

There are many methods of preventing counterfeiting and deterring fraudulent producers of goods. Some attempts have included putting encoded or unencoded markings directly on the goods themselves (analogous to an artist's signature on his or her painting). The problem with this methodology is that as soon as the counterfeiter learns to emulate the "signature", the technique becomes defunct and worthless for authentication purposes.

In the realm of currency, anti-counterfeiting methods have become quite sophisticated—the use of two-dimensional authentication mechanisms such as watermarks or special threads incorporated within the paper itself are helpful. However, they remain vulnerable to reverse-engineering. Once a potential counterfeiter learns how to emulate the anti-counterfeiting technology, he may use it to his own advantage. Therefore, the simple release of anti-counterfeiting technology into the world can be an indirect pathway to advance the state of criminal technology.

There is thus a great need to develop a system in order to reproduce these highly encrypted patterns which can be used to authenticate associated objects, as well as an ability to quickly and accurately verify these objects for authenticity. Thermal and digital printers, for example, can be used to duplicate highly complicated patterns having, for example, macroscopically detectable anisotropic optical properties and domains, as well as encrypted codes, while hand-held readers and variations thereon could make this process extremely brisk, while not sacrificing accuracy. There is therefore a great need to demarcate the means for the cheap and relatively simple reproduction of these highly technical encrypted patterns and the tools used to authenticate them, so that criminals would be discouraged from, essentially, counterfeiting the anti-counterfeiting measures described herein.

Two types of methods evolved for preventing counterfeiting: counterfeit resistant features, such as signatures, special printing, special document recording medium recording stock, magnetic and/or electrical features, and the like; and legal sanctions for an otherwise easy copying process. For example, most cultures provide heavy sanctions for counterfeiting of currency, typically much harsher than private document counterfeiting.

PRIOR ART

A wide variety of attempts have been made to limit the likelihood of counterfeiting. For example, some have tried to assure the authenticity of items by putting coded or uncoded markings thereon (e.g., an artist's signature on his or her painting). Unfortunately, as soon as the code is broken—e.g., a counterfeiter learns to duplicate a signature, this method becomes worthless for authentication purposes. In the context of paper products (e.g., currency), counterfeiting-prevention methods have also used two-dimensional authentication mechanisms—e.g., watermarks or special threads incorporated within the paper used to make the currency. These mechanisms are clearly helpful, but they can also be overcome. For example, counterfeiters routinely bleach a one-dollar bill (in such a way that the colored threads, which mark the special currency paper, are not damaged) and then imprint the markings of a one hundred-dollar bill thereon. Thus, the mere release of physical security materials into the market forms one limitation on their unfettered use.

Other authentication methods have utilized mechanisms that provide three dimensions of data. For example, the holograms provided on many credit cards provide more variables (i.e., relative to two-dimensional threads or watermarks) which may be precalibrated, and thereafter, used to verify the authenticity of an item. Nevertheless, since holograms have a pre-set, or deterministic, pattern they may also be duplicated and counterfeit products made. Further, since the holograms are invariant, they are subject to pilferage before application to goods, or translocation from authorized to unauthorized goods in the marketplace. Authentication mechanisms, which utilize deterministic patterns, are inherently vulnerable to counterfeiting since the counterfeiter, in essence, has a "fixed" target to shoot at. High security schemes, such as military codes, have encryption keys that change frequently. This method, however, assists prospectively in securing valuable time-sensitive information, and does not prevent subsequent decryption of a previously transmitted message. At the other end of the spectrum, a random element-based authentication mechanism would provide an incessantly "moving" and nonrepeating target that would be practically impossible to undetectably duplicate, without knowledge of the encoding scheme.

Finally, although existing authentication mechanisms provide adequate protection against counterfeiting in some contexts, increasingly powerful tools are available to decode encrypted messages, making more secure schemes necessary for long-term protection. For example, in conjunction with its monitoring and surveillance activities, governments routinely seek to break or circumvent encryption codes. The technologies employed are then quickly adopted by the private sector, and indeed government regulations seek to maintain weak encryption standards, facilitating code-breaking. In addition to computers, current counterfeiters have access to extremely powerful tools for undermining physical copy-protection schemes—e.g., color photocopying equipment, reverse engineering of semiconductor chips, etc. These factors have combined to continually provoke strong demand for new methods and mechanisms for authenticating items, especially methods and mechanisms that are less vulnerable to counterfeiting and/or employ new copy-protection mechanisms.

More recently, techniques have evolved for authentication of digital information, for example based on cryptographic techniques. However, these techniques do not serve to verify the authenticity of a particular copy of the information. In fact, modern digital content protection schemes do seek to prevent digital copying of content; however, these rely on secure hardware for storage of the digital content, and a breach of hardware security measures results in copyable content with no distinction between an original and a copy thereof.

A number of modern systems implement challenge-response authentication, which provide enhanced security for encryption keys and encrypted content. See, for example, U.S. Pat. No. 6,028,937 (Tatebayashi et al.), U.S. Pat. No. 6,026,167 (Aziz), U.S. Pat. No. 6,009,171 (Ciacelli et al.) (Content Scrambling System, or "CSS"), U.S. Pat. No. 5,991,399 (Graunke et al.), U.S. Pat. No. 5,948,136 (Smyers) (IEEE 1394-1995), and U.S. Pat. No. 5,915,018 (Aucsmith), and Jim Wright and Jeff Robillard (Philsar Semiconductor), "Adding Security to Portable Designs", Portable Design, March 2000, pp. 16-20, expressly incorporated herein by reference.

The present invention therefore addresses instances where the issue is not merely whether the information is authentic, but rather whether the information is authentic (and unaltered), and the copy itself an original. Obviously, known techniques may be used to authenticate the content of a document, for example, by providing self-authenticating digital signatures, remote database authentication, trusted intermediary techniques, and the like. Likewise, numerous techniques are available for providing self-authenticating features for the physical medium, for example, security threads, inks, papers and watermarks, printing techniques (e.g., intaglio printing, microlithography), fluorescent inks and/or fibers, steganographic patterns, magnetic and/or electrical/electronic patterns, and the like.

In fact, database techniques are known for authenticating objects associated with documents (labels or certificates), in which the document is both self-authenticating and may further reference a remote database with authentication information for the document or associated object. These techniques, however, are not intended to primarily secure the document itself, and thus the techniques fail to particularly address document content security and authentication, as well as models for commercial exploitation thereof.

It is known that the color of an object can be represented by three values, and that the color may be used for identification and authentication. For example, the color of an object can be represented by red, green and blue values, an intensity value and color difference values, by a CIE (International Commission on Illumination, usually known as the "CIE" for its French-language name Commission internationale de l'eclairage) value, or by what are known as "tristimulus values" or numerous other orthogonal combinations. For most tristimulus systems, the three values are orthogonal; i.e., any combination of two elements in the set cannot be included in the third element. One such method of quantifying the color of an object is to illuminate an object with broad band "white" light and measure the intensity of the reflected light after it has been passed through narrow band filters. Typically three filters (such as red, green and blue) are used to provide tristimulus light values representative of the color of the surface. Yet another method is to illuminate an object with three monochromatic light sources or narrow band light sources (such as red, green and blue) one at a time and then measure the intensity of the reflected light with a single light sensor. The three measurements are then converted to a tristimulus value representative of the color of the surface. Such color measurement techniques can be utilized to produce equivalent tristimulus values representative of the color of the surface. Generally, it does not matter if a "white" light source is used with a plurality of color sensors (or a continuum in the case of a spectrophotometer), or if a plurality of colored light sources are utilized with a single light sensor.

Tamper Evident Certificates

U.S. Pat. Nos. 5,913,543 and 5,370,763 (Curiel), expressly incorporated herein by reference, relates to a tamper evident and counterfeit resisting document, for example a temporary vehicle registration which may be made of paper or paperboard. The document has a zone for inserting information and a pattern within said zone for resisting counterfeiting. A transparent tape which preferably has a silicone resin coating which contains a wax is adhesively secured over information contained within the zone. In other embodiments, an alteration resistant article contains variable data and includes an outer film having an upper surface and a lower surface with an adhesive secured to the lower surface. A hologram for receiving at least a portion of the variable data on the upper surface is secured to the outer film lower surface and, in one embodiment, the hologram has portions which have release properties and portions which have greater adhesive bonding properties than the release containing portions. These respective portions may be established by providing a release material on certain portions of the upper surface of the hologram and providing adhesive enhancing materials on other portions of the hologram upper surface. The hologram may be embossed and have a metalized upper surface. A plurality of relatively small hologram particles may be provided in the outer layer and/or the adhesive layer. The hologram is secured to a substrate which, in one embodiment, has an upper surface printed with pattern means which are printed to a lesser depth than the variable data. In another embodiment, the hologram is provided as a unit with the outer film and overlies the variable data. This system therefore provides physical techniques for document authentication and preventing content alteration.

U.S. Pat. No. 5,601,683 (Martin, Feb. 11, 1997), expressly incorporated herein by reference, provides a photocopy resistant document, having a background pattern or logo which is printed with solvent-sensitive, dye based ink. The presence of this photocopy-resistant background pattern or logo limits copying.

U.S. Pat. No. 5,949,042 (Dietz, II, et al., Sep. 7, 1999), expressly incorporated herein by reference, provides a gaming ticket validation system and method. This patent discloses the use of a validating system, whereby to deter fraud, a validation code is provided which uniquely identifies an article by a combination of a validator machine and a host computer. The validator machine reads the validation code and relays it to the host computer to check for legitimacy (proper form and availability) and to correlate it to a stored record of indicia. If approved, the host computer sends its record of indicia back to the validator machine for display on a monitor. The method is summarized as (1) printing a validation code on an article consisting of a combination of numbers and/or symbols which validation code uniquely identifies said article; (2) inserting said article into a first validator which reads the validation code and communicates this code to a separate second validator; (3) comparing the validation code with second validator to a list of legitimate and available article validation codes stored in a memory of this second validator and determining if the code is valid; (4) finding a record in the memory of the second validator which spits out certain necessary information correlating to that code (location of sale, date of manufacture, style, etc).

Artificial Watermarks

U.S. Pat. No. 5,928,471 (Howland, et al. Jul. 27, 1999), expressly incorporated herein by reference, relates to improved security features for paper, and in particular to a method of making paper and "transparentising" selected areas of paper to provide enhanced security features. The invention thus provides a method of making paper comprising the step of depositing fibers onto a support surface to form a porous absorbent sheet, applying a "transparentising" resin to at least portion of said porous sheet and subsequently impregnating the porous sheet with a sizing resin.

The following patents, expressly incorporated herein by reference, provide enhanced security features for use with finished paper and for non-currency and non-security papers. EP-A2-0203499 discloses a method of applying a pseudo watermark to paper. This method comprises the preparation of a paper containing thermally sensitive material, the presence of which renders the translucency of the paper variable by temperature change. When heat is subsequently applied to a part of the surface of the paper, a region of the paper becomes semi-translucent. U.S. Pat. No. 2,021,141 (Boyer, November 1935) discloses a method of applying pseudo watermarks to paper, by applying a resinous composition to finished paper which permeates the paper and causes it to become more transparent, or translucent, than the surrounding area. GB-A-1489084 describes a method of producing a simulated watermark in a sheet of paper. The sheet is impregnated in the desired watermark pattern with a "transparentising" composition which, when submitted to ultra violet radiation, polymerizes to form a simulated watermark. U.S. Pat. No. 5,118,526 (Allen, et al., Jun. 2, 1992) describes a method of producing simulated watermarks by applying heat, in the desired watermark pattern, onto a thin solid matrix of waxy material placed in contact with a sheet of paper. This results in an impression of a durable translucent watermark. U.S. Pat. No. 4,513,056 (Vernois, et al., Apr. 23, 1985) relates to a process for rendering paper either wholly or partially transparent by impregnation in a special bath of a "transparentization" resin and subsequent heat cross-linking of the resin. EP-A1-0388090 describes a method of combining a see-through or print-through feature with a region of paper which has a substantially uniform transparency which is more transparent than the majority of the remainder of the sheet. JP 61-41397 discloses a method for making paper transparent and a method for its manufacture for see-through window envelopes. The method utilizes the effect of causing ink cross-linked by ultra-violet rays to permeate paper thus causing that part of the paper to become transparent.

Copy Resistant Printing Techniques

U.S. Pat. No. 5,946,103 (Curry, Aug. 31, 1999), expressly incorporated herein by reference, relates to halftone patterns for trusted printing. Predetermined machine and/or human readable information is embedded in at least one serpentine pattern that is printed on each original document, so that any given instance of such a document can be later verified or refuted as being the original by determining whether this information can be recovered from the document or not. The method for verifying the originality of printed documents, said comprises providing at least one trusted printer for printing original documents, embedding predetermined information in each of the original documents in at least one halftone pattern that is composed of halftone cells, each of the cells containing a fill pattern which is symmetric about a central axis of the cell, with the information being represented by the angular orientations of the respective axis of symmetry of at least some of the cells; and classifying the documents as original documents only if said predetermined information can be recovered therefrom. Thus, the technique relies on information which can be readily printed but not readily photocopied.

Self-clocking glyph codes have been developed for embedding machine readable digital data in images of various descriptions. See, for example, Bloomberg et al. (U.S. Ser. No. 08/240,798) for Self-Clocking Glyph Codes and U.S.

Pat. No. 5,453,605 (Hecht et al., Sep. 26, 1995) for Global Addressability for Self-Clocking Glyph Codes, which are expressly incorporated herein by reference. To integrate these glyph codes into line art images, the data typically are embedded in small, similarly sized, spatially formatted, elliptical or slash-like marks or "glyphs" which are slanted to the left or right in generally orthogonal orientations to encode binary zeros ("0's") or ones ("1's"), respectively. Customarily, these glyphs are written on a spatially periodic, two-dimensional lattice of centers at a density that enables up to about 500 bytes of data per square inch to be stored on a document. These glyph codes are well suited for incorporating digital data channels into textual and other types of line art images.

U.S. Pat. No. 5,193,853 (Wicker, Mar. 16, 1993), and U.S. Pat. No. 5,018,767 (Wicker, May 28, 1991), expressly incorporated herein by reference, provide anti-counterfeiting methods wherein a marked image has a minute dot or line pitch which varies from normal scanning resolution of typical copying devices, making such mechanical copying detectable.

U.S. Pat. No. 5,315,112, (Tow, May 24, 1994) expressly incorporated herein by reference, for Methods and Means for Embedding Machine Readable Digital Data in Halftone Images, describes the use of "circularly asymmetric" halftone dots for incorporating self-clocking glyph codes into halftone images, and defines a workable approach if the data is confined to the midtone regions of the image in accordance with a known or identifiable spatial formatting rule. High sensitivity, however, is required to recover the embedded data with acceptable reliability from the darker or lighter regions of the image.

U.S. Pat. No. 5,706,099, (Curry, Jan. 6, 1998) for Method and Apparatus for Generating Serpentine Halftone Images, expressly incorporated herein by reference, provides circular serpentine halftone cell structures, e.g., Truchet tiles, for embedding data in images. These serpentine halftone cells have a high degree of rotational tone invariance. The arcuate fill patterns may be rotated 45 degrees with respect to the halftone cell boundaries to produce another rotationally distinguishable pair of halftone structures. These structures have been called Manhattans and also are sometimes referred to as ortho-serpentines.

As described in more detail in U.S. Pat. No. 5,696,604, (Curry, Dec. 9, 1997) for Analytic Halftone Dot Construction for a Hyperacuity Printer U.S. Pat. No. 5,410,414 (Curry, Apr. 25, 1995) for Halftoning in a Hyperacuity Printer, and U.S. Pat. No. 5,710,636 (Curry, Jan. 20, 1998) for Method and Apparatus for Generating Halftone Images Having Human Readable Patterns Formed Therein, which are hereby expressly incorporated by reference, halftone patterns may be generated somewhat differently from the traditional way that halftones are generated. The goal is to more precisely control the way the edges of the halftone fill pattern or "shape" evolves as it grows from highlight to shadow. More particularly, in traditional digital halftoning, turning on an appropriate number of bits in a threshold array generates the desired tone. The array holds a sequence of threshold values that may spiral outward from a central location as the threshold values ascend. Bits corresponding to those locations in the halftone cell "turn on" if the incoming data intensity is equal to or greater than the threshold value for that bit location. This method generates halftone dots that grow asymmetrically, as one threshold after another is traversed through a range of intensity values from, say, 0 to 255. For serpentine patterns, however, it is desired to grow the halftone fill pattern at all positions on its perimeter simultaneously to maintain better control of the shape. Therefore, a two step process typically is employed for generating the halftone fill patterns. First, an analytical shape function is defined which grows according to a predetermined evolution from the smallest shape for highlight regions, through midtones, and finally to full coverage of the halftone cell. In this step, shape information is maintained with "infinite precision" with analytic functions. Second, as the area of the shape gets larger, the fill pattern or shape is rendered as if it were a segment of text or line art with a corresponding shape. The result is more control over the shape and the tone evolution of the halftone because they are defined with analytic functions. Nevertheless, it is believed that would be possible to use the traditional thresholding array to generate serpentines given a large enough threshold array.

There are two main goals when analytically defining the shape function. The first is to define functions that can evolve through growth from the smallest shape at intensity value of zero to the largest shape at a value of, say, 255 in a continuous manner. Any jumps in tone caused by discontinuities in the functions will be readily visible in the halftone images. The second goal is ensure that the functions can be solved for the position and angle of the nearest edge of the shape from any point within the halftone cell, at all stages of its evolution with analytic accuracy. This allows the shape, which is defined by a hyperbolic shape function, to be precisely rendered. The strategy used to create a family of curves is to fix the focal point to a suitable value, and then select a x, y value along a halftone cell side, for each family member.

One of the qualities that causes the tone of serpentine halftone patterns to be substantially invariant to rotation is that there is very little change at the boundary between neighboring halftone cells upon 90-degree rotation. This is achieved by selecting the points of intersection for the curve pair defining the fill patterns or shape to be equidistant from the midpoint of the halftone cell side. Two hyperbolic curves are used to define the serpentine shape, and the points at which those curves intersect the periphery of the halftone cell are selected so that these intersections are equally displaced in opposite directions from the midpoint of the cell side. In order to make full use of the analytic precision with which the halftone shape is defined, the rendering of the edges of the shape typically is carried out by modulating the laser of a laser printer with a precision that is finer than the size of the scan spot. For instance, in the time it takes the spot to sweep out its own diameter, up to eight bits of digital information can be provided for modulating it. Likewise, inkjet printers may also produce modulated dot patterns.

The serpentines printed in full color, with the correct color balance and halftone shapes are extremely difficult to reproduce reprographically. The narrow, diagonally extending, unfilled areas in halftone cells representing the darker tones are especially difficult to reproduce faithfully because ordinary copying tends to cause near neighboring shapes to blur together, thereby degrading (if not obliterating) the shape information and clues that aid in determining cell direction. Without these distinguishing features, the image takes on the form of a "waffle" pattern, and is easily recognized as a forgery. Although typical color copiers are excellent at reproducing the correct tones for high quality images, they must supply their own halftone algorithms to do this properly. They usually have their own electronic halftoners embedded in the electronics of the machine, and these halftoners typically are optimized for machine dependent tone reproduction curves and implementationally dependent halftone dot shapes. Accordingly, it is extremely unlikely that an existing halftone that is not a serpentine can reproduce a serpentine halftone. Another possible method of reproducing serpentine images is to scan them in, process the image to determine cell orientation, then reproduce the original data file required to print an "original". This requires access to a printer that can print serpentines, an unlikely prospect for the casual counterfeiter.

Accordingly, serpentines are an excellent candidate for trusted printing applications. For this application, a "trusted printer" (i. e., a printer controlled by a trusted party, such as a service bureau) typically is employed for printing original documents that are designed to include one or more serpentine patterns. Predetermined machine and/or human readable information is embedded in at least one of the serpentine patterns that is printed on each original document, so that any given instance of such a document can be later verified or refuted as being the original instance by attempting to recover this known information from the document in question. This is not an absolute safeguard against counterfeiting, but it is a significant hindrance to those who may attempt to pass off xerographic copies or other conveniently produced copies as original documents.

The feature that gives serpentines a large dynamic range also makes them difficult to copy. As the hyperbolas asymptotically approach the limiting diagonal of the halftone cell, the small region of white is extremely difficult to copy without loss of contrast. The resulting "waffle" appearance of the halftone screen conveniently lacks directionality. This makes serpentines a candidate for image authentication and counterfeit deterrence.

Moiré effects have been used in prior art for the authentication of documents. For example, United Kingdom Pat. No. 1,138,011 (Canadian Bank Note Company) discloses a method which relates to printing on the original document special elements which, when counterfeited by means of halftone reproduction, show a moiré pattern of high contrast. Similar methods are also applied to the prevention of digital photocopying or digital scanning of documents (for example, U.S. Pat. No. 5,018,767 (Wicker), or U.K. Pat. Application No. 2,224,240 A (Kenrick & Jefferson)). In all these cases, the presence of moiré patterns indicates that the document in question is counterfeit. Another known method provides a moiré effect used to make visible an image en coded on the document (as described, for example, in the section "Background" of U.S. Pat. No. 5,396,559 (McGrew, Mar. 7, 1995)), based on the physical presence of that image on the document as a latent image, using the technique known as "phase modulation". In this technique, a uniform line grating or a uniform random screen of dots is printed on the document, but within the pre-defined borders of the latent image on the document the same line grating (or respectively, the same random dot-screen) is printed in a different phase, or possibly in a different orientation. For a layman, the latent image thus printed on the document is hard to distinguish from its background; but when a reference transparency consisting of an identical, but unmodulated, line grating (respectively, random dot-screen) is superposed on the document, thereby generating a moiré effect, the latent image pre-designed on the document becomes clearly visible, since within its pre-defined borders the moiré effect appears in a different phase than in the background.

U.S. Pat. No. 6,039,357 (Kendrick, Mar. 21, 2000), expressly incorporated herein by reference, relates to security bands to prevent counterfeiting with color copies. A protected/security document is provided that foils counterfeiting even if a laser photocopy machine is utilized. The document has at least three discrete half-tone printed bands disposed on its surface, provided by dots or lines. Each printed band has a different screen density and within each bands the dots or lines comprise a warning word or symbol (e.g. "Void"), or a background. The dots or lines of either the "Void" or background drop out when photocopied, while the dots or lines of the other do not. The dots or lines that do not drop out may be dimensioned so that there are about 24-34 per centimeter, while for those that do drop out there are about 52-64 per centimeter. The bands are typically arranged either linearly or in concentric circles, and interband areas having density gradually transitioning between the densities of adjacent bands are provided. The total density variation between discrete bands is typically about 10-35%, depending upon ink color, typically about 1.0-10% gradation between adjacent bands. Full tone indicia, which does readily reproduce, is also printed on the substrate.

U.S. Pat. No. 5,995,638 (Amidror, et al., Nov. 30, 1999), expressly incorporated herein by reference, relates to methods and apparatus for authentication of documents by using the intensity profile of moiré patterns, occurring between superposed dot-screens. By using a specially designed basic screen and master screen, where at least the basic screen is comprised in the document, a moiré intensity profile of a chosen shape becomes visible in their superposition, thereby allowing the authentication of the document. If a microlens array is used as a master screen, the document comprising the basic screen may be printed on an opaque reflective support, thereby enabling the visualization of the moiré intensity profile by reflection. Automatic document authentication is supported by an apparatus comprising a master screen, an image acquisition means such as a CCD camera and a comparing processor whose task is to compare the acquired moiré intensity profile with a prestored reference image. Depending on the match, the document handling device connected to the comparing processor accepts or rejects the document. An important advantage is that the process can be incorporated into the standard document printing process, so that it offers high security at the same cost as standard state of the art document production. The system is based on the moiré phenomena which are generated between two or more specially designed dot-screens, at least one of which being printed on the document itself. Each dot-screen consists of a lattice of tiny dots, and is characterized by three parameters: its repetition frequency, its orientation, and its dot shapes. Dot-screens with complex dot shapes may be produced by means of the method disclosed in U.S. patent application Ser. No. 08/410,767 filed Mar. 27, 1995 (Ostromoukhov, Hersch).

U.S. Pat. No. 6,014,453 (Sonoda, et al., Jan. 11, 2000), expressly incorporated herein by reference, relates to a counterfeit detecting method and device to generate counterfeit probability data and apparatus employing same. Counterfeit probability data are generated indicating that a non-reproducible document is being processed even when the pattern which identifies such documents has been defaced. One set of rules and membership functions is stored in each of three memory sets, for each of (1) an unaltered pattern identifying a non-reproducible document, (2) an altered version of that pattern, and (3) a pattern identifying an ordinary reproducible document. A fuzzy inference unit uses these rules and membership functions to generate data representing the probability that a counterfeiting attempt is occurring. These probability data are transmitted to the copy machine through a control CPU to prevent unlawful copying.

U.S. Pat. Nos. 6,045,881, 6,001,516, 5,919,730, 5,864,742, 5,856,266, 5,843,564, and 5,752,152, expressly incorporated herein by reference, provide a label or certificate which contains one or more microdots that are embedded in the label or certificate for providing a non-visual, but machine detectable mark or marks. The detected means for detecting the presence of one or more microdots in the label or certificate inhibits a copy machine from copying the document (another embodiment can include the encryption or encoding of signatures into a plurality of microdots for assigning document ownership). Here the original label or certificate is placed on a bed of a scanner to provide a digitized sequence of scanner signals to a digital image processing unit that incorporates a keyboard, touch screen and/or a mouse, for operator interfacing and a monitor for viewing the scanned image. A printer is directly attached to the digital image processing unit or is attached via a communication link. With either configuration the printer forms hard copy prints. An algorithm residing in the digital image processing unit, detects the presence of the microdot pattern in the original document and automatically deactivates the printer to abort the document copying process thereby restricting the unauthorized copying of the original document. In other words, the microdots are undetectable by the unaided eye, but detectable by copying machines associated with software that programs the machine to prevent copying, when microdots are detected.

Chemical Testing

U.S. Pat. No. 6,030,655 (Hansmire, et al., Feb. 29, 2000), expressly incorporated herein by reference, relates to positive identification and protection of documents using inkless fingerprint methodology. A system is provided for coating a portion of the document with a chemical compound, for determining an image thereupon, including the steps of first providing a document; next, applying a clear chemical coating onto at least a portion of the document; applying an non-visible image onto the chemical coated portion of the document; providing an activator solution; applying the activated solution to the chemically coated portion of the document to reveal the image thereupon; identifying the stamped image for assuring that the stamped image is not a counterfeit or the like.

U.S. Pat. No. 5,289,547 (Ligas, et al., Feb. 22, 1994), expressly incorporated herein by reference, discloses a method for authenticating articles including incorporating into a carrier composition a mixture of at least two photochromic compounds that have different absorption maxima in the activated state and other different properties to form the authenticating display data on the article, subjecting the display data to various steps of the authenticating method, activation of all photochromic compounds, preferential bleaching of less than all of the photochromic compounds, and/or bleaching of all the photochromic compounds, and subsequent examination of the display data following the various activation and bleaching steps by verifying means to enable authentication.

U.S. Pat. No. 4,507,349 (Fromson, et al. Mar. 26, 1985), expressly incorporated herein by reference, provides a currency security system employing synthetic layers and sublimatable dye-formed images on the layers.

Physical Characteristics

U.S. Pat. No. 4,767,205 (Schwartz, et al., Aug. 30, 1988), expressly incorporated herein by reference, discloses an identification method and identification kit based upon making up groups of microsized particles normally visible to the naked eye with each particle in each group being of a selected uniform size, shape and color. Coded identification is established by transferring a population of particles from a selected number of the groups to the item to be identified and then confirming such identification by examining the marked item under high magnification with a light microscope.

Physical Security Schemes—Films and Embedded Filaments

U.S. Pat. No. 4,157,784 (Grottrup, et al., Jun. 12, 1979), expressly incorporated herein by reference, discloses a document security system that optically reveals erasures or modifications of printed matter.

U.S. Pat. No. 3,391,479 (Buzzell et al., July, 1968), expressly incorporated herein by reference, discloses a card security system that provides a dichroic film covering information on the card.

U.S. Pat. No. 3,880,706 (Williams, April, 1975), expressly incorporated herein by reference, discloses a document security system provided by a fused polymer net within a paper pulp substrate.

U.S. Pat. No. 4,247,318 (Lee, et al., Jan. 27, 1981), expressly incorporated herein by reference, provides a security paper formed from non-woven polyethylene film-fibril sheets.

U.S. Pat. No. 4,186,943 (Lee, Feb. 5, 1980), expressly incorporated herein by reference, discloses a banknote or document security system that provides an optically distinctive thin film structure in the body of the banknote or document.

U.S. Pat. No. 4,445,039 (Yew, Apr. 24, 1984), expressly incorporated herein by reference, discloses an encoded document security system having a security element with a readable physical characteristic.

U.S. Pat. No. 4,652,015 (Crane, Mar. 24, 1987), expressly incorporated herein by reference, discloses security paper for banknotes and currency having a metalized film having fine imprinting thereon.

U.S. Pat. No. 4,552,617 (Crane, Nov. 12, 1985), expressly incorporated herein by reference, discloses a document security system provides dissolvable strips of microcarrier material having encoding thereon which persists after the carrier dissolves.

U.S. Pat. No. 4,437,935 (Crane, Jr., Mar. 20, 1984), expressly incorporated herein by reference, discloses a document security system provides a dissolvable carrier web material having encoding thereon which attaches to the paper fibers and persists after the web dissolves.

U.S. Pat. No. 5,393,099 (D'Amato, Feb. 28, 1995), expressly incorporated herein by reference, provides an anti-counterfeiting method for currency and the like having embedded micro image security features, such as holograms and diffraction gratings.

Physical Security Schemes—Electromagnetic

U.S. Pat. No. 5,602,381 (Hoshino, et al., Feb. 11, 1997), and U.S. Pat. No. 5,601,931 (Hoshino, et al., Feb. 11, 1997), expressly incorporated herein by reference, relate to system and method for authenticating labels based on a random distribution of magnetic particles within the label and an encrypted code representing the distribution printed on the label, and possibly data imprinted on the label.

U.S. Pat. No. 3,701,165 (Huddlester, October, 1972), expressly incorporated herein by reference, discloses a method of marking garments with a substance detectable by magnetic detecting devices. When the magnetized substance on the garment part is detected in a process of making garments, subsequent garment making steps are actuated in response to the detection of the stitching.

U.S. Pat. No. 4,820,912 (Samyn, Apr. 11, 1989), expressly incorporated herein by reference, provides a method and apparatus utilizing microwaves for authenticating documents, having a random distribution of stainless steel fibers embedded and scattered in a card base member. Microwaves are applied to a large number of metallic wires which are embedded and scattered at random in a document or a card, and a proper digital mark responsive to a response microwave signature is recorded in a suitable region of the document or card according to specific rules. To check the authenticity of the document or card, microwaves are applied to the document or card, and a response microwave signature is collated with the digital mark. The document or card is determined as being authentic when the microwave signature and the mark correspond.

Optical Characteristics and Detection

U.S. Pat. No. 5,325,167 (Melen, Jun. 28, 1994), expressly incorporated herein by reference, relates to a record document authentication by microscopic grain structure and method. A record document may be authenticated against reference grain data obtained from the document at a prior time. The body of the document is formed by base medium bearing the record entries such as text within record site. The grain seal site is located at a predetermined location within the base medium. The unique grain structure within the seal site are microscopic and function as a seal for authenticating the document. The seal site is initially scanned to provide a stream of reference data generated by the surface reflection of the grain structure. This reference grain data is stored in memory for future authentication use. The seal site is then currently scanned to generate a stream of current grain data for comparison to the reference grain data.

U.S. Pat. No. 3,942,154 (Akami, et al., Mar. 2, 1976), expressly incorporated herein by reference, discloses a method and apparatus for recognizing colored patterns. The method includes encoding the colors of individual picture elements in a fabric pattern by comparing the level of transmittance or reflectance of the picture element at pre-selected wavelengths with stored values representing a reference color to generate a multibit code indicative of the color of the picture element. A comparator used for this purpose incorporates an error either proportional to the wavelength or of constant value so that the output of the comparator will indicate identity with the stored value if the input value for the picture element is within a certain range of the stored value.

U.S. Pat. No. 4,514,085 (Kaye, Apr. 30, 1985), expressly incorporated herein by reference, provides a method for authenticating documents by marking the document with an encapsulated liquid crystal, and then observing the document under conditions which exploit the unique optical characteristics of liquid crystals.

U.S. Pat. No. 5,591,527 (Lu, Jan. 7, 1997), expressly incorporated herein by reference, provides optical security articles and methods for making same, having layers of varying refractive index forming an image, which is viewable only across a narrow range of viewing angles and is viewable in ambient (diffuse) light, thus affording a readily apparent verification of the authenticity of the substrate.

U.S. Pat. No. 5,580,950 (Harris, et al., Dec. 3, 1996), expressly incorporated herein by reference, provides negative birefringent rigid rod polymer films, formed of a class of soluble polymers having a rigid rod backbone, which when used to cast films, undergo a self-orientation process aligning the polymer backbone parallel to the film surface, resulting in a film that displays negative birefringence.

U.S. Pat. No. 5,549,953 (Li, Aug. 27, 1996), expressly incorporated herein by reference, provides optical recording media having optically variable security properties. Thin film structures, which have an inherent color shift with viewing angle, provide both optically variable security properties and optical data decodable by optical means. The multilayer interference coating has a dielectric material, which is transparent, and a recording layer made of a light absorbing material, a crystalline-structural changing material, or a magneto-optic material. Data is encoded optically or photolithographically as bar codes or digital data.

The use of optically variable pigments has been described in the art for a variety of applications, such as inks for counterfeit-proof applications such as currency, and generically for coating compositions. They are described, for example, in U.S. Pat. No. 4,434,010 (Ash, Feb. 28, 1984), U.S. Pat. No. 4,704,356 (Ash, Feb. 28, 1984), U.S. Pat. No. 4,779,898 (Berning, et al., Oct. 25, 1988), U.S. Pat. No. 4,838,648 (Phillips, et al., Jun. 13, 1989), U.S. Pat. No. 4,930,866 (Berning, et al., Jun. 5, 1990), U.S. Pat. No. 5,059,245 (Phillips, et al., Oct. 22, 1991), U.S. Pat. No. 5,135,812 (Phillips, et al., Aug. 4, 1992), U.S. Pat. No. 5,171,363 (Phillips, et al., Dec. 15, 1992), and U.S. Pat. No. 5,214,530 (Coombs, et al., May 25, 1993), expressly incorporated herein by reference. Pigments of these types are prepared by depositing inorganic transparent dielectric layers, semi-transparent metal layers, and metal reflecting layers onto a flexible web, and separating the layers from the web in such a manner as to fragment the deposited thin film layer structure into pigment particles. These particles are in the form of irregularly shaped flat pigment flakes. These pigments are capable of producing dramatic visual effects, including dichroic effects not observed in other types of pigments. A multilayer thin film interference structure is formed having at least one metal reflecting layer, at least one transparent dielectric layer, and at least one semi-transparent metal layer. Various combinations of these layers can be utilized to achieve the desired optically variable effect. Layer thickness can be varied according to the particular desired characteristics of the pigment. For example, U.S. Pat. No. 5,135,812, expressly incorporated herein by reference, describes useful thickness being on the order of 80 nm for the metal reflecting layer, 5 nm for the semi-opaque metal layers, and thickness of a plurality of halfwaves of the particular design wavelength for the transparent dielectric layers.

U.S. Pat. No. 6,038,016 (Jung, et al., Mar. 14, 2000) and U.S. Pat. No. 5,966,205 (Jung, et al., Oct. 12, 1999), expressly incorporated herein by reference, relate to a method and apparatus for optically detecting and preventing counterfeiting. Perimeter receiver fiber optics are spaced apart from a source fiber optic and receive light from the surface of the object being measured. Light from the perimeter fiber optics pass to a variety of filters. The system utilizes the perimeter receiver fiber optics to determine information regarding the height and angle of the probe with respect to the object being measured. Under processor control, the optical characteristics measurement may be made at a predetermined height and angle. Translucency, fluorescence, gloss and/or surface texture data also may be obtained. Measured data also may be stored and/or organized as part of a data base. Such methods and implements are desirably utilized for purposes of detecting and preventing counterfeiting or the like.

Fluorescent Fibers and Patterns

U.S. Pat. No. 1,938,543 (Sanburn, December, 1933), expressly incorporated herein by reference, teaches that detectable fibers which have been specially treated with a chemically sensitive substance can be incorporated into paper and, upon contacting such paper with a second chemical agent, the detectable fibers change color and become distinguishable. As illustrated in U.S. Pat. No. 2,208,653 (Whitehead, July, 1940), expressly incorporated herein by reference, authenticatable paper can also be made by including fibers of an organic ester of cellulose that have been treated with a tertiary amine. The treated fibers are invisible in the paper and become fluorescent under ultraviolet light. U.S. Pat. No.

2,379,443 (Kantrowitz et al., July, 1945), expressly incorporated herein by reference, discloses authenticatable paper made by the addition of a small percentage of cellulosic fibers that have been treated with hydrated ferric chloride which has been hydrolyzed to iron hydroxide. The treated fibers are capable of acquiring a deep blue color upon application to the paper of a potassium ferrocyanide solution, followed by an orthophosphoric acid solution.

U.S. Pat. No. 3,839,637 (Willis, Oct. 1, 1974), expressly incorporated herein by reference, discloses the impregnation of spaced courses of yarn in a fabric with a material which is not visible under daylight, but which is visible only when subjected to ultra-violet light, so as to provide guide lines for cutting, or measuring indicia to enable visual counting of the number of yards of cloth in a roll from the end thereof without the necessity of unrolling the bolt.

U.S. Pat. No. 4,623,579 (Quon, Nov. 18, 1986), expressly incorporated herein by reference, discloses a decorative composite article, which may be longitudinally slit to form a yarn product, which has a combined phosphorescent and fluorescent decorative appearance. The composite article includes paired outer layers of a thermoplastic resin between which is disposed a decorative layer comprising a composition including a colorant component having a phosphorescent colorant and a fluorescent colorant, and a resin binder material. The fluorescent colorant is present in an amount by weight that is up to an amount equal to that of the phosphorescent colorant. The present binder material may be selected from polyester, polyurethane and acrylic polymers and copolymers, with a mixture of butadiene-acrylonitrile rubber and polyurethane composition being preferred. The composite article is prepared by coating two resin films with the composition, followed by contacting the films with each other on their coated surfaces and applying heat and pressure to bond them together to form the decorative composite article.

U.S. Pat. No. 4,756,557 (Kaule, et al., Jul. 12, 1988), expressly incorporated herein by reference, relates to a security document having a security thread embedded therein and methods for producing and testing the authenticity of the security document. In order to increase the protection of security documents such as ban notes, etc., against forgery, security threads are embedded in the document that have at least two areas extending in the longitudinal direction of the thread and differing in their physical properties. The thread is preferably a coextruded multicomponent synthetic thread whose individual components contain additives such as dyes or fluorescent substances and/or particles having electrical or magnetic properties. The testing of the authenticity of the security thread is directed toward the presence of these additives and their mutual geometrical distribution in certain areas of the security thread.

U.S. Pat. No. 6,019,872 (Kurrle, Feb. 1, 2000), expressly incorporated by reference, relates to authenticatable bleached chemical paper products, prepared from a bleached chemical papermaking furnish containing a minor but detectable amount of lignin containing fibers selected from the group consisting of mechanical, thermomechanical, chemi-thermomechanical and bleached-chemi-thermomechanical, in an amount sufficient to be detectable with the use of a phloroglucinol staining technique.

U.S. Pat. No. 6,054,021 (Kurrle, et al., Apr. 25, 2000), expressly incorporated herein by reference, relates to a process of manufacturing authenticatable paper products, in which the paper made from the papermaking furnish includes fluorescent cellulosic fibers.

U.S. Pat. No. 6,045,656 (Foster, et al., Apr. 4, 2000), expressly incorporated herein by reference, relates to a process for making and detecting anti-counterfeit paper. In this process, a certain percentage of wood fiber lumens which have been loaded with one or more fluorescent agents are added to the papermaking pulp. These wood fiber lumens would look normal under regular light, but will glow when exposed to various manners of radiation.

U.S. Pat. No. 6,035,914 (Ramsey, et al., Mar. 14, 2000), expressly incorporated herein by reference, for counterfeit-resistant materials and a method and apparatus for authenticating materials, relates to the use of fluorescent dichroic fibers randomly incorporated within a media to provide an improved method for authentication and counterfeiting protection. The dichroism is provided by an alignment of fluorescent molecules along the length of the fibers. The fluorescent fibers provide an authentication mechanism of varying levels of capability. The authentication signature depends on four parameters; the x, y position, the dichroism and the local environment. The availability of so many non-deterministic variables makes counterfeiting difficult. Essentially, fibers having a readily detectable, non-RGB colorspace characteristic, e.g., fluorescent dichroism, are embedded randomly within a fibrous substrate. Fibers near the surface are readily identified due to their fluorescence. The fibers are then analyzed for dichroism, i.e., having a polarization axis. The positions of these dichroic fibers are useful for authenticating the substrate.

The fibers are distributed throughout the media in a random fashion during the production process. Thus the fiber related signature is a random variable rather than a deterministic one. In fact, it is not believed that any methods presently exist for copying fiber placement within a substrate. The signature of every item will be different making it more difficult to reverse engineer. For example, two-dimensional images (e.g. in the x-y plane) of papers incorporating the inventive fluorescent dichroic fibers provide increased security over the prior art "blue" threads used in currency. A comparison of a white light image and a fluorescence image showing the two-dimensional distribution of florescent dichroic fibers provides unique information. Fibers lying at or near the surface of the paper are easily observed by the white light image but are quickly masked below the surface. In a fluorescence image, fibers that lie below the surface are also readily observable. A comparison of the two images provides a signature. Furthermore, processing of the paper (calendaring) further alters this image comparison. The pressing process reduces the fluorescence from the surface fibers while not perturbing the subsurface fibers thus depth information is available by comparing the two images.

The fluorescent fibers' emission characteristics will also vary depending upon the angular orientation of the fibers within the media relative to a polarized excitation source. For example, at a given wavelength, the intensity of electro-magnetic energy emitted by the fibers may vary considerably depending upon whether the fibers within the media are vertically or horizontally oriented relative to the direction of a linearly polarized excitation source and a parallel polarization analyzer. Hence, the dichroic nature of the fibers provides a fourth variable for each point along the fiber (i.e., x, y, z and dichroism/emission behavior).

The emission spectrum of each fluorescent dichroic fiber, can provide data on the fiber's local environment. For example, consider the use of the present invention in paper media or in an aerosol application. The local environment of the fluorescent, dichroic fibers cause photon scattering (e.g., the orientation and number density of the paper fibers) and absorption (e.g., varying thickness of the dried carrier vehicle in an aerosol application). This local environment is indirectly observed through the measurement of the fluorescent dichroic fiber's apparent fluorescent anisotropy. This apparent fluorescent anisotropy assumes random values because the process of incorporating the fibers into the media is a random process.

It is not necessary to analyze each variable for authentication; varying levels of security may be obtained by selecting one or more feature for analysis. For example, at the first level (i.e., the lowest authentication/lowest cost), an item having fluorescent dichroic fibers incorporated therewith may merely be checked to see that the fluorescent fibers are present in the item. The particular fluorescent agent used may be kept secret and dyes which fluoresce in non-visible regions of the electromagnetic spectrum may be employed, so copying this feature may be difficult. At the second level of authentication accuracy, an item having fluorescent, dichroic fibers may be checked to see that the florescent fibers present in the media have the correct fluorescence anisotropy. This level of authentication exceeds that of the first level because the fluorescence anisotropy is dependent upon the molecular structure of the fluorescent molecule and the specific processing conditions used to prepare the fibers containing the fluorescent molecules. The third level of authentication accuracy involves generating a prerecorded x-y pattern of the fluorescent fibers in the item (e.g., by logging the particular random pattern of fibers present in a particular credit card when the card is manufactured). When the item is presented for authentication the observed pattern is compared with the prerecorded pattern. Since each item would have a unique pattern, detection of a counterfeit would simply involve detection of a duplicate or unmatchable pattern. At the highest level of authentication accuracy, the x-y-apparent fluorescent anisotropy pattern of the fluorescent dichroic fibers in the item would be prerecorded. As in the above case, when the item is presented for authentication the observed pattern is compared with the prerecorded pattern. Since the values for the variables in the x-y-apparent fluorescent anisotropy pattern are random, this level of authentication yields an item that is virtually impossible to duplicate. Calculations, using the number density of "blue" and "red" fibers incorporated into currency paper as a base case, indicate that the probability of a random repeat of the x-y-apparent fluorescent anisotropy pattern is about 1 part in $10^{1000}$, an extremely unlikely event.

Cryptographic Techniques

The original forms of cryptography involved the use of a single secret key that was used to both encrypt and decrypt the message (known as symmetric cryptography). One challenge to this technique is the logistics of communicating the secret key to the intended recipient without other parties gaining knowledge of the key. In 1976, Whitfield Diffie and Martin Hellman introduced the concept of Public Key cryptography (asymmetric cryptography). In their system, each person is the owner of a mathematically related pair of keys: a Public Key, intended to be available to anyone who wants it; and a Private Key, which is kept secret and only known by the owner. Because messages are encrypted with a Public Key and can only be decrypted by the related Private Key, the need for the sender and receiver to communicate secret information (as is the case in symmetric cryptography) is eliminated.

Public Key encryption is based on two mathematically related keys that are generated together. Each key in the pair performs the inverse function of the other so what one key encrypts, the other key decrypts, and vice versa. Because each key only encrypts or decrypts in a single direction, Public Key encryption is also known as asymmetric encryption. Encryption and authentication take place without any sharing of Private Keys: each person uses only another's Public Key or their own Private Key. Anyone can send an encrypted message or verify a signed message, but only someone in possession of the correct Private Key can decrypt or sign a message.

The two primary uses of Public Key cryptography, encryption and digital signatures. Encryption messages are encrypted by using the Public Key of the intended recipient. Therefore, in order to encrypt a message, the sender must either have or obtain the Public Key from the intended recipient. The recipient of the message decrypts the message by using their Private Key. Because only the recipient has access to the Private Key (through password protection or physical security), only the recipient can read the message. In order to create a digital signature, the sender's computer performs a calculation that involves both the sender's Private Key and the message. The result of the calculation is a digital signature, which is then included as an attachment to the original message. The recipient of the message performs a similar calculation that includes the message, the digital signature of the sender, and the sender's Public Key. Based on the result of the recipient's calculation, known as a hash, it can be determined whether the signature is authentic (or is fraudulent) and whether the message had been intercepted and/or altered at any point between the sender and the recipient.

In most cryptosystems, with some exceptions, such as elliptic key encryption, the larger the key size, the stronger the encryption. While some people could argue that you can never have too strong a level of encryption, in the world of cryptography the word 'overkill' can certainly be applicable. With stronger encryption comes greater system complexity and longer processing durations to both encrypt and decrypt.

Presently, there are four different 'grades,' that refer to the strength of the protection: Export grade gives minimal real protection (40-bit for symmetric encryption or 512 for asymmetric). Personal grade (56- or 64-bits symmetric, 768 asymmetric) is recommended for keys that are not very important, such as those that protect one person's personal e-mail or those that serve as 'session keys' for low-importance transactions. Commercial grade (128-bit symmetric or 1024 asymmetric) is recommended for information that is valuable and fairly sensitive, such as financial transactions. Military grade (160-bit symmetric or 2048-bit asymmetric) is recommended for information that is truly sensitive and must be kept secret at any cost.

U.S. Pat. No. 5,984,366 (Priddy, Nov. 16, 1999), expressly incorporated herein by reference, relates to unalterable self-verifying articles. Self-verifying article creation includes receiving recipient-specific data, encoding a first selected subset of the recipient-specific data and fixing the encoded subset along with other human-recognizable data on a surface of an article. Self-verifying article authentication includes scanning a surface to locate an encoded first data set, decoding the first data set and comparing the decoded first data set with a control data set, which may also be fixed upon the surface, to determine the authenticity of the received self-verifying article. According to one disclosed embodiment, enhanced data security can be obtained and maintained by verifying a machine-readable data set on an object for acceptability against predetermined criteria which may include searching a data base (e.g., an organized, comprehensive collection of data stored for use by processing system(s)) of previously issued articles to determine uniqueness. The transmission may be by wired or non-wired communication. In order to verify authenticity, an encoded data set (divided in two) on an article to be authenticated is read and processed, locally or remotely, to first check consistency between the divided parts, and to provide biometric authentication information about a presenter or bearer of the object.

U.S. Pat. No. 5,932,119 (Kaplan, et al. Aug. 3, 1999), and WO 97/25177, Shachrai et al., expressly incorporated herein by reference, relate to a laser marking system, with associated techniques for authenticating a marked workpiece. Images of marked objects are stored, and may be authenticated through a database, and/or through a secure certificate of authenticity, including an image of the marked object. According to Kaplan et al., difficult to reproduce characteristics of an object are used as an integrity check for an encoded message associated with the object. These characteristics may be measured or recorded, and stored, for example within a marking on the object, or in a database. Advantageously, these measurements and characteristics may be derived from an image of the object captured in conjunction with the marking process. In fact, by storing such images and providing a pointer to the image, e.g., a serial number, the measurements or characteristics to be compared need not be determined in advance. Therefore, according to such a scheme, the object to be authenticated need only include a pointer to a record of a database containing the data relating to the object to be authenticated. This allows information relating to characteristics of the object, which may be difficult to repeatably determine or somewhat subjective, to be preserved in conjunction with the object. An image of the object on a certificate of authenticity may be used to verify that the object is authentic, while providing a tangible record of the identification of the object. Known secure documents and methods for making secure documents and/or markings are disclosed in U.S. Pat. No. 5,393,099 (D'Amato, Feb. 28, 1995); U.S. Pat. No. 5,380,047 (Molee, et al., Jan. 10, 1995); U.S. Pat. No. 5,370,763 (Curiel, Dec. 6, 1994); U.S. Pat. No. 5,243,641 (U.S. Pat. No. 4,247,318 (Lee, et al., Jan. 27, 1981); U.S. Pat. No. 4,199,615 (Wacks, et al., Apr. 22, 1980); U.S. Pat. No. 4,059,471 (Haigh, Nov. 22, 1977); U.S. Pat. No. 4,178,404 (Allen, et al., Dec. 11, 1979); and U.S. Pat. No. 4,121,003 (Williams, Oct. 17, 1978), expressly incorporated herein by reference. U.S. Pat. No. 5,464,690 (Boswell, Nov. 7, 1995) and U.S. Pat. No. 4,913,858 (Miekka, et al., Apr. 3, 1990), expressly incorporated herein by reference, relate to certificate having holographic security devices.

It is known to provide a number of different types messages for cryptographic authentication. A so-called public key/private key encryption protocol, such as available from RSA, Redwood Calif., may be used to label the workpiece with a "digital signature". See, "A Method for Obtaining Digital Signatures and Public Key Cryptosystems" by R. L. Rivest, A. Shamir and L. Adelmann, Communications of ACM 21(2):120-126 (February 1978), expressly incorporated herein by reference. In this case, an encoding party codes the data using an appropriate algorithm, with a so-called private key. To decode the message, one must be in possession of a second code, called a public key because it may be distributed to the public and is associated with the encoding party. Upon use of this public key, the encrypted message is deciphered, and the identity of the encoding party verified. In this scheme, the encoding party need not be informed of the verification procedure. Known variations on this scheme allow private communications between parties or escrowed keys to ensure security of the data except under exceptional authentication procedures. See also, W. Diffie and M. E. Hellman, "New directions in cryptography", IEEE Trans. Information Theory, Vol. IT-22, pp. 644-654, November 1976; R. C. Merkle and M. E. Hellman, "Hiding information and signatures in trapdoor knapsacks", IEEE Trans. Information Theory, Vol. IT-24, pp. 525-530, September 1978; Fiat and Shamir, "How to prove yourself: practical solutions to identification and signature problems", Proc. Crypto 86, pp. 186-194 (August 1986); "DSS: specifications of a digital signature algorithm", National Institute of Standards and Technology, Draft, August 1991; and H. Fell and W. Diffie, "Analysis of a public key approach based on polynomial substitution", Proc. Crypto. (1985), pp. 340-349, expressly incorporated herein by reference. Another encoding scheme uses a DES-type encryption system, which does not allow decoding of the message by the public, but only by authorized persons in possession of the codes. This therefore requires involvement of the encoding party, who decodes the message and assists in authentication.

U.S. Pat. No. 6,028,936 (Hillis, Feb. 22, 2000), U.S. Pat. No. 6,021,202 (Anderson, et al., Feb. 1, 2000), U.S. Pat. No. 6,009,174 (Tatebayashi, et al. Dec. 28, 1999), U.S. Pat. No. 5,375,170 (Shamir, Dec. 20, 1994), U.S. Pat. No. 5,263,085 (Shamir, Nov. 16, 1993), and U.S. Pat. No. 4,405,829 (Rivest, et al., Sep. 20, 1983), incorporated herein by reference, provide encryption and digital signature or document content distribution schemes. U.S. Pat. No. 5,600,725 (Rueppel, et al., Feb. 4, 1997), and U.S. Pat. No. 5,604,804 (Micali, Feb. 18, 1997), incorporated herein by reference, provide public key-private key encryption systems. U.S. Pat. No. 5,166,978 (Quisquater, Nov. 24, 1992), incorporated herein by reference, provides a microcontroller for implementing so-called RSA schemes. U.S. Pat. No. 6,002,772 (Saito, Dec. 14, 1999), expressly incorporated herein by reference, provides an embedded digital watermark scheme.

The document content, or a digital signature thereof, may be stored remotely, and retrieved based on a unique identification of the document. The required communications may, for example, occur through use of the Internet. See, U.S. Pat. No. 6,052,780 (Glover, Apr. 18, 2000), U.S. Pat. No. 6,011,905 (Huttenlocher, et al. Jan. 4, 2000) and U.S. Pat. No. 5,933,829 (Durst, et al., Aug. 3, 1999), expressly incorporated herein by reference.

U.S. Pat. No. 6,065,119 (Sandford, II, et al., May 16, 2000), expressly incorporated herein by reference, provides a method of authenticating digital data such as measurements made for medical, environmental purposes, or forensic purpose, and destined for archival storage or transmission through communications channels in which corruption or modification in part is possible. Authenticated digital data contain data-metric quantities that can be constructed from the digital data by authorized persons having a digital key. To verify retrieved or received digital data, the data-metrics constructed from the retrieved or received data are compared with similar data-metrics calculated for the retrieved or received digital data. The comparison determines the location and measures the amount of modification or corruption in the retrieved or received digital data.

Methods that hide validation information within the data being authenticated offer an alternative means to validate digital data. Digital watermarks can be added to data by methods falling generally into the field of steganography. Steganographic methods are reviewed by W. Bender, D. Gruhl, and N. Morimoto in "Techniques for Data Hiding," Proc. SPIE, Storage and Retrieval for Image and Video Databases III, 9-10 Feb. 1995, San Jose, Calif., expressly incorporated herein by reference.

One method of impressing a digital watermark is given by G. Caronni, in "Assuring Ownership Rights for Digital Images," Proc. Reliable IT Systems, VIS '95, 1995, edited by H. H. Bruggemann and W. Gerhardt-Hackl (Vieweg Publ. Co.: Germany). Another method is given by I. J. Cox, J. Kilian, T. Leighton, and T. Shamoon in "Secure Spread Spectrum Watermarking for Multimedia," NEC Research Inst.

Tech. Report 95-10, 1995. These references also are expressly incorporated herein by reference.

Unlike the checksum or digital signature that calculate a measure of the original data, digital watermarking techniques modify the data in order to encode a known signature that can be recovered. The presence of the hidden signature in received data verifies that the data are unchanged, or its absence reveals that the data were modified from the watermarked form. The method of Cox et al., NEC Research Inst. Tech. Report 95-10 (1995) is designed specifically for digital images, and it is sufficiently robust to survive even transformations of the digital data to analog form. However, all the above methods proposed for digital watermarking generally detect modifications by means of an external signature, i.e., no metric that measures the fidelity of the original digital data is used. Consequently, there exists no ability to measure in any detail the extent of the changes made or to estimate the precision of the received data. The steganographic watermarking methods differ from the digital signature and checksum methods primarily by being invisible, and by using the digital data to convey the watermark, thus eliminating the need for an appended value.

U.S. Pat. No. 5,592,549 (Nagel, et al., Jan. 7, 1997), expressly incorporated herein by reference, relates to a method and apparatus for retrieving selected information from a secure information source. A device is disclosed for retrieving information from a secure electronic information source, wherein at least some of the information is in encrypted form and may be decrypted for use. The device comprises: (a) a computer, having an input device and a display device, for selecting information to be retrieved from the information source; (b) an information retrieval device, coupled to the computer, for retrieving the selected information from the information source; (c) a decryption device, coupled to the computer, for decrypting at least portions of the selected information retrieved from the information source; and (d) a data logging device, coupled to the computer, for maintaining a data log of the selected information as it is retrieved from said information source and decrypted. According to the invention, a unique brand code is automatically, electronically added to at least some of the selected and decrypted information, and to the data log.

U.S. Pat. No. 5,394,469, expressly incorporated herein by reference, of Robert Nagel and Thomas H. Lipscomb discloses a personal computer or "host computer" a CD-ROM reader and a "decryption controller". The decryption controller is addressable by the host computer as if it were the CD-ROM reader. Upon receipt of an information request, the decryption controller initiates a request to the CD-ROM reader for the desired information, retrieves this information, decrypts it (if it is encrypted) and then passes it to the host computer. The decryption controller is thus "transparent" to the host computer.

U.S. Pat. No. 6,044,463 (Kanda, et al., Mar. 28, 2000) expressly incorporated herein by reference, relates to a method and system for message delivery utilizing zero knowledge interactive proof protocol. The message delivery system guarantees the authenticity of a user, the reliability of a message delivery, and the authenticity of the message delivery, while preventing an illegal act, and which can prove them at a later time. The system has an information provider terminal including a user authentication unit for carrying out a user authentication of the user according to a zero knowledge interactive proof protocol using check bits E generated according to a work key W, and a transmission unit for transmitting to the user a cipher-text C in which a message M to be delivered to the user is enciphered according to a secret key cryptosystem by using the work key W, and the check bits E. The system also has a user terminal including a message reception unit for taking out the work key W by using at least the check bits E, and obtaining the message M by deciphering the ciphertext C according to the secret key cryptosystem by using the work key W.

U.S. Pat. No. 5,926,551 (Dwork, et al., Jul. 20, 1999) expressly incorporated herein by reference, elates to a system and method for certifying content of hard-copy documents. The system and method facilitate proof that a specific item, such as a document, has been sent via a communication medium, such as the mail service of the United States Postal Service, at a specific time. A bit map image is produced, such as by scanning a hard copy document. Preferably the bit map is compressed into a data string and hashed. The hash file is signed by a certifying authority, such as the USPS, using an existentially unforgeable signature scheme. The original document, a code representation of the string, and a code representation of the signature are sent via the communication medium. As a result, the combination of materials sent provides proof of the authenticity of the content of the document.

U.S. Pat. No. 5,745,574 (Muftic, Apr. 28, 1998), expressly incorporated herein by reference, relates to a security infrastructure for electronic transactions. A plurality of certification authorities connected by an open network are interrelated through an authentication and certification system for providing and managing public key certificates. The certification system with its multiple certification and its policies constitute a public key infrastructure facilitating secure and authentic transactions over an unsecure network. Security services for applications and users in the network are facilitated by a set of common certification functions accessible by well-defined application programming interface which allows applications to be developed independently of the type of underlying hardware platforms used, communication networks and protocols and security technologies.

A digital signature standard (DSS) has been developed that supplies a shorter digital signature than the RSA standard, and that includes the digital signature algorithm (DSA) of U.S. Pat. No. 5,231,668 (Kravitz, Jul. 27, 1993), expressly incorporated herein by reference. This development ensued proceeding from the identification and signature of the U.S. Pat. No. 4,995,081 (Leighton, et al., Feb. 19, 1991) and proceeding from the key exchange according to U.S. Pat. No. 4,200,770 (Hellman, et al., Apr. 29, 1980) or from the El Gamal method (El Gamal, Taher, "A Public Key Cryptosystem and a Singular Scheme Based on Discrete Logarithms", 1 III Transactions and Information Theory, vol. IT-31, No. 4, July 1985), all of which are expressly incorporated herein by reference.

U.S. Pat. No. 6,041,704 (Pauschinger, Mar. 28, 2000), expressly incorporated herein by reference, relates to a public key infrastructure-based digitally printed postage system. See also, U.S. Pat. No. 6,041,317 (Brookner, Mar. 21, 2000), U.S. Pat. No. 6,058,384 (Pierce, et al., May 2, 2000) and European Patent Application 660 270, expressly incorporated herein by reference, which apply encrypted postage markings to mail. U.S. Pat. No. 5,953,426 (Windel, et al. Sep. 14, 1999), expressly incorporated herein by reference, discloses a private key method for authenticating postage markings. A data authentication code (DAC) is formed from the imprinted postage message, this corresponding to a digital signature. The data encryption standard (DES) algorithm disclosed in U.S. Pat. No. 3,962,539 (Ehrsam et al., June. 1976), is thereby applied, this being described in FIPS PUB 113 (Federal Information Processing Standards Publication), which are expressly incorporated herein by reference.

The data in the deciphered message includes a set of unique or quasi unique characteristics for authentication. In this scheme, the encoding party need not be informed of the verification procedure.

Typical encryption and document encoding schemes that may be incorporated, in whole or in part, in the system and method according to the invention, to produce secure certificates and/or markings, are disclosed in U.S. Pat. No. 5,422,954 (Berson, Jun. 6, 1995); U.S. Pat. No. 5,337,362 (Gormish, et al. Aug. 9, 1994); U.S. Pat. No. 5,166,978 (Quisquater, Nov. 24, 1992); U.S. Pat. No. 5,113,445 (Wang, May 12, 1992); U.S. Pat. No. 4,893,338 (Pastor, Jan. 9, 1990); U.S. Pat. No. 4,879,747 (Leighton, et al., Nov. 7, 1989); U.S. Pat. No. 4,868,877 (Fischer, Sep. 19, 1989); U.S. Pat. No. 4,853,961 (Pastor, Aug. 1, 1989); and U.S. Pat. No. 4,812,965 (Taylor, Mar. 14, 1989), expressly incorporated herein by reference. See also, W. Diffie and M. E. Hellman, "New directions in cryptography", IEEE Trans. Information Theory, Vol. IT-22, pp. 644-654, November 1976; R. C. Merkle and M. E. Hellman, "Hiding information and signatures in trapdoor knapsacks", IEEE Trans. Information Theory, Vol. IT-24, pp. 525-530, September 1978; Fiat and Shamir, "How to prove yourself: practical solutions to identification and signature problems", Proc. Crypto 86, pp. 186-194 (August 1986); "DSS: specifications of a digital signature algorithm", National Institute of Standards and Technology, Draft, August 1991; and H. Fell and W. Diffie, "Analysis of a public key approach based on polynomial substitution", Proc. Crypto. (1985), pp. 340-349, expressly incorporated herein by reference.

In order to provide enduring authentication, it may be desired that multiple codes, containing different information in different schemes, be encoded on the object, so that if the security of one code is breached or threatened to be breached, another, generally more complex code, is available for use in authentication. For example, a primary code may be provided as an alphanumeric string of 14 digits. In addition, a linear bar code may be inscribed with 128-512 symbols. A further 2-D array of points may be inscribed, e.g., as a pattern superimposed on the alphanumeric string by slight modifications of the placement of ablation centers, double ablations, laser power modulation, and other subtle schemes which have potential to encode up to about 1 k-4 k symbols, or higher, using multi-valued modulation. Each of these increasingly complex codes is, in turn, more difficult to read and decipher.

As is known from U.S. Pat. No. 5,932,119 (Kaplan, et al., Aug. 3, 1999), expressly incorporated herein by reference, intrinsic imperfections or perturbations in the marking process may be exploited for authentication. Thus, a pattern may be provided which can be analyzed, but for which techniques for copying are generally unavailable. Thus, a marking pattern, even applied using standard means, may provide an opportunity for counterfeit resistant feature identification.

In like manner, intentional or "pseudorandom" irregularities (seemingly random, but carrying information in a data pattern) may be imposed on the marking, in order to encode additional information on top of a normally defined marking pattern. Such irregularities in the marking process may include intensity modulation, fine changes in marking position, and varying degrees of overlap of marked locations. Without knowledge of the encoding pattern, the positional irregularities will appear as random jitter and the intensity irregularities will appear random. Because a pseudorandom pattern is superimposed on a random noise pattern, it may be desirable to differentially encode the pseudorandom noise with respect to an actual encoding position or intensity of previously formed markings, with forward and/or backward error correcting codes. Thus, by using feedback of the actual marking pattern rather than the theoretical pattern, the amplitude of the pseudorandom signal may be reduced closer to the actual noise amplitude while allowing reliable information retrieval. By reducing the pseudorandom signal levels and modulating the pseudorandom signal on the actual noise, it becomes more difficult to duplicate the markings, and more difficult to detect the code without a priori knowledge of the encoding scheme.

A number of authentication schemes may be simultaneously available. Preferably, different information is encoded by each method, with the more rudimentary information encoded in the less complex encoding schemes. Complex information may include spectrophotometric data, and image information. Thus, based on the presumption that deciphering of more complex codes will generally be required at later time periods, equipment for verifying the information may be made available only as necessary.

Known techniques for using ID numbers and/or encryption techniques to preventing counterfeiting of secure certificates or markings are disclosed in U.S. Pat. No. 5,367,148 (Storch, et al., Nov. 22, 1994); U.S. Pat. No. 5,283,422 (Storch, et al. Feb. 1, 1994); and U.S. Pat. No. 4,814,589 (Storch, et al., Mar. 21, 1989), expressly incorporated herein by reference.

In addition to being analyzed for information content, i.e., the markings, the object image may also be compared with an image stored in a database. Therefore, based on a presumptive identification of an object, an image record in a database is retrieved. The image of the presumptive object is then compared with the stored image, and any differences then analyzed for significance. These differences may be analyzed manually or automatically. Where a serial number or other code appears, this is used to retrieve a database record corresponding to the object that was properly inscribed with the serial number or code. Where the code corresponds to characteristics of the object and markings, more than one record may be retrieved for possible matching with the unauthenticated object. In this case, the information in the database records should unambiguously authenticate or fail to authenticate the object.

U.S. Pat. No. 5,974,150 (Kaish, et al., Oct. 26, 1999), expressly incorporated herein by reference, relates to a system and method for authentication of goods. An authentication system is provided based on use of a medium having a plurality of elements, the elements being distinctive, detectable and disposed in an irregular pattern or having an intrinsic irregularity. Each element is characterized by a determinable attribute distinct from a two-dimensional coordinate representation of simple optical absorption or simple optical reflection intensity. An attribute and position of the plurality of elements, with respect to a positional reference is detected. A processor generates an encrypted message including at least a portion of the attribute and position of the plurality of elements. The encrypted message is recorded in physical association with the medium. The elements are preferably dichroic fibers, and the attribute is preferably a polarization or dichroic axis, which may vary over the length of a fiber. An authentication of the medium based on the encrypted message may be authenticated with a statistical tolerance, based on a vector mapping of the elements of the medium, without requiring a complete image of the medium and elements to be recorded.

See also: U.S. Pat. Nos. 7,336,806, 7,324,133, 7,315,629, 7,299,984, 7,288,320, 7,254,838, 7,251,347, 7,228,428, 7,226,087, 7,194,618, 7,188,258, 7,165,268, 7,162,035, 7,159,241, 7,152,047, 7,142,301, 7,119,662, 7,116,222, 7,114,750, 7,114,074, 7,092,583, 7,089,420, 7,080,857, 7,080,041, 7,076,084, 7,062,065, 7,055,814, 7,051,205, 7,035,428, 6,996,543, 6,985,607, 6,980,654, 6,979,827, 6,973,198, 6,973,196, 6,970,236, 6,948,068, 6,901,862, 6,885,755, 6,883,982, 6,882,738, 6,861,012, 6,813,011, 6,801,641, 6,788,800, 6,782,116, 6,746,053, 6,724,921, 6,722,699, 6,712,399, 6,535,128, 6,528,318, 6,522,749, 6,483,576, 6,476,351, 6,397,334, 6,381,346, 6,246,061, 6,212,638, 6,211,484, 6,086,966, 2007/0205284, 2007/0119951, 2007,0023715, 2006/0219961, 2006/0157559, each of which are expressly incorporated herein by reference.

U.S. Pat. No. 5,592,561 (Moore, Jan. 7, 1997), expressly incorporated herein by reference, suggests a system that provides an authenticating, tracking/anti-diversion, and anti-counterfeiting system that can track various goods. The system includes a control computer, a host computer, a marking system, and a field reader system, which are all compatible and can be physically linked via data transmission links. An identifiable and unique mark is placed on each good, or on materials out of which the goods are to be made, which enables subsequent inspection. The marks or patterns include areas where a marking agent is applied in an encrypted pattern and areas where it is not applied. The pattern can be scanned or captured by a reader and deciphered into encoded data. The entry can then either be compared directly to a set of authentic entries on a database or decoded and compared to a set of data on the centrally located host database. The marking system provides control over imprinting, allowing a limited number of authorized codes to be printed before reauthorization is required. In order to provide marking validation, a camera captures images of imprints. After imprinting of the encoded marking, an image of the marking is obtained and centrally authenticated as a valid code, which may be stored in a database along with stored pertinent information pertaining to this specific product. Monitoring of the marked goods is facilitated by including a unique encrypted pattern having, for example, a unique owner identifier, a unique manufacturer identifier, a unique plant identifier, a unique destination identifier, and time and date information.

U.S. Pat. No. 5,367,319 (Graham, Nov. 22, 1994), expressly incorporated herein by reference, provides a system wherein an object, such as currency, is randomly marked, such as with an ink jet printer. Counterfeiting of the object by copying is detected by sensing duplication of the random pattern.

U.S. Pat. No. 5,499,924 (Berson, et al., May 30, 1995), expressly incorporated herein by reference, relates to a digital camera with an apparatus for authentication of images produced from an image file. U.S. Pat. No. 5,351,302 (Leighton, et al., Sep. 27, 1994), expressly incorporated herein by reference, relates to a method for authenticating objects based on a public key cryptography method encoding an ascertainable characteristic of the object, such as a serial number.

U.S. Pat. No. 5,574,790 (Liang, et al., Nov. 12, 1996), expressly incorporated herein by reference, provides a multiple-reader system for authentication of articles based on multiple sensed fluorescent discriminating variables, such as wavelengths, amplitudes, and time delays relative to a modulated illuminating light. The fluorescent indicia incorporate spatial distributions such as bar codes as discriminating features, to define a user-determined and programmable encryption of the articles' authentic identity.

U.S. Pat. No. 5,426,700 (Berson, Jun. 20, 1995), expressly incorporated herein by reference, provides a public key/private key system for verification of classes of documents, to verify the information content thereof. U.S. Pat. No. 5,420,924 (Berson, et al. May 30, 1995), and U.S. Pat. No. 5,384,846 (Berson, et al., Jan. 24, 1995), expressly incorporated herein by reference, provide secure identification cards bearing an image of the object to be authenticated. U.S. Pat. No. 5,388,158, expressly incorporated herein by reference, provides a method for making a document secure against tampering or alteration.

U.S. Pat. Nos. 5,191,613, 5,163,091 (Graziano, et al., Nov. 10, 1992), U.S. Pat. No. 5,606,609 (Houser, et al., Feb. 25, 1997), and U.S. Pat. No. 4,981,370 (Dziewit, et al., Jan. 1, 1991), expressly incorporated herein by reference, provide document authentication systems using electronic notary techniques. U.S. Pat. No. 6,049,787 (Takahashi, et al., Apr. 11, 2000), U.S. Pat. No. 5,142,577 (Pastor, Aug. 25, 1992), U.S. Pat. No. 5,073,935 (Pastor, Dec. 17, 1991), and U.S. Pat. No. 4,853,961 (Pastor, Aug. 1, 1989), expressly incorporated herein by reference, provide digital notary schemes for authenticating electronic documents.

U.S. Pat. No. 4,816,655 (Musyck, et al., Mar. 28, 1989), expressly incorporated herein by reference, provides a document authentication scheme which employs a public key-private key scheme and which further employs unscrambled information from the document.

U.S. Pat. No. 4,637,051 (Clark, Jan. 13, 1987), expressly incorporated herein by reference, provides a system for printing encrypted messages which are difficult to forge or alter.

U.S. Pat. No. 4,630,201 (White, Dec. 16, 1986), expressly incorporated herein by reference, provides an electronic transaction verification system that employs random number values to encode transaction data.

U.S. Pat. No. 4,463,250 (McNeight, et al., Jul. 31, 1984), expressly incorporated herein by reference, provides a method for detecting counterfeit codes based on a low density coding scheme and an authentication algorithm.

See also, U.S. Pat. No. 4,150,781 (Silverman, et al., Apr. 24, 1979); U.S. Pat. No. 4,637,051 (Clark, Jan. 13, 1987); U.S. Pat. No. 4,864,618 (Wright, et al., Sep. 5, 1989); U.S. Pat. No. 4,972,475 (Sant' Anselmo, Nov. 20, 1990); U.S. Pat. No. 4,982,437 (Loriot, Jan. 1, 1991); U.S. Pat. No. 5,075,862 (Doeberl, et al., Dec. 24, 1991); U.S. Pat. No. 5,227,617 (Christopher, et al., Jul. 13, 1993); U.S. Pat. No. 5,285,382 (Muehlberger, et al., Feb. 8, 1994); U.S. Pat. No. 5,337,361 (Wang, et al., Aug. 9, 1994); U.S. Pat. No. 5,370,763 (Curiel, Dec. 6, 1994); U.S. Pat. No. 4,199,615 (Wacks, et al., Apr. 22, 1980); U.S. Pat. No. 4,178,404 (Allen, et al., Dec. 11, 1979); U.S. Pat. No. 4,121,003 (Williams, Oct. 17, 1978), U.S. Pat. No. 5,422,954 (Berson, Jun. 6, 1995); U.S. Pat. No. 5,113,445 (Wang, May 12, 1992); U.S. Pat. No. 4,507,744 (McFiggans, et al., Mar. 26, 1985); and EP 0,328,320, expressly incorporated herein by reference.

Anticounterfeiting Systems for Objects

U.S. Pat. No. 6,005,960, expressly incorporated herein by reference, provides an anti-counterfeiting system wherein a system and method of marking goods for authentication and tracking purposes is described. A central control unit enables the system by providing an allotment of goods to a host unit. The host unit directs marking terminals to mark particular goods with specific information coding symbols. Goods are either marked directly or are identified by means of affixed features which are marked with encoding symbols either prior to, or subsequent to, affixing to the goods. Following marking, goods of fixtures are scanned to ensure proper marking and then packaged for shipment, and/or they can be checked by illuminating the symbols marked thereon and cross referencing this data with the host database by using a field reading unit.

U.S. Pat. No. 4,397,142, expressly incorporated herein by reference, describes coded threads and sheet materials for making such threads useful in counterfeit-inhibiting garments. The sheet material comprises transparent microspheres, a specularly reflective layer underlying the microspheres, and a polymeric layer underlying the specularly reflective layer and containing particulate matter which may be varied from sheet material to sheet material to encode information and allow identification of the sheet material. The sheet material is split in narrow widths and incorporated into threads.

U.S. Pat. No. 4,527,383, expressly incorporated herein by reference, describes a thread which comprises a polymeric material onto which has been fixed a symbol or repeating multiple symbols which are detectable and readable under magnification. When incorporated into garments or garment labels, this thread is useful in identifying the true manufacturer of the goods, and the absence of such threads would help in the detection of counterfeit goods.

U.S. Pat. No. 5,956,409, expressly incorporated herein by reference, discloses a method and system for the secure application of seals. An optical image of a seal is recorded by a computer and encrypted using a key for encryption generated in response to template biometric data from the authorized persons. When a person seeks to use the seal, for example to apply the seal to a document or label, test biometric data is input from that person and used to generate a key for decryption. If the test biometric data matches the template biometric data, the key for decryption will be useful for decrypting the encrypted seal, and the person seeking access to the seal. The test biometric data represents a handwritten signature given contemporaneously by the person seeking access, and is verified against a set of template signatures earlier given by at least one authorized person. Specific signature features are determined in response to the template signatures and used for generating one or more keys for encrypting the seal. Similarly, specific signature features are determined in response to the test signature and used for generating keys for decrypting the seal. Features are embedded in the optical image of the seal, or in the printed seal in the event that the document or label is physically printed, which demonstrate to a person examining the document that the seal is genuine. These features include micro-embedding of biometric data or specific features determined in response thereto, or even the embedding of dichroic fibers in or patterns thereon.

SUMMARY AND OBJECTS OF THE INVENTION

The present invention provides a method and apparatus for the production and labeling of objects in a manner suitable for the prevention and detection of counterfeiting.

Some technologies have tried to assure the authenticity of articles by putting coded or uncoded markings onto products. Once the code is broken, however, i.e., a counterfeiter learns to duplicate a "signature," this method loses value for authentication. Two-dimensional authentication methods have also been attempted. These methods are helpful, but they, too, can be overcome. Other, pre-calibrated three-dimensional data (i.e., holograms) have also been utilized. Nevertheless, to the extent that holograms are pre-set and deterministic they may also be duplicated. Deterministic authentication mechanisms are inherently vulnerable to counterfeiting since the counterfeiter has a "fixed" target.

One aspect of the current technology exploits random (i.e., non-deterministic, meaning, to the accuracy of measurement, the metric of the characteristic is not predefined by the manufacturing procedure) patterns of distinctive and unique optical fluorescent fibers (or other optically readable materials), and provides a constantly "moving" and non-repeating target, drastically reducing, if not mathematically eliminating, the possibility of duplication. An algorithmically generated numeric value or code is then assigned and printed on to each article, appearing in close proximity to the random pattern that must correspond to the measured characteristics of the pattern.

This technology may be applied, in some embodiments, to cost effectively and dramatically enhance the protection and levels of security to detect counterfeit and diverted products. The scheme permits relatively easy detection of counterfeit products or documents by manufacturers' or government inspectors who can check document or product authenticity in real time using a reader, which can observe the random pattern and the code, and determine whether the correspondence is sufficient for validation. This validation preferably has some tolerance for deviation of the pattern as read from the encoded information, and the tolerance of the validation may be selected or defined based on likely artifacts in the authentication process not due to counterfeiting, or likely changes in the article between the creation of the authentication code and its use.

The possibility of duplicate codes occurring is statistically unlikely (for example, less than 1 in $10^{15}$). Further, a counterfeiter would have to simultaneously duplicate the fiber material, the fibers' optical traits, and must employ the same optics to break the system. Finally, the scanning of fibers must also occur at the correct location on the document, and the resulting image must match the associated code. The result is immediate authentication of any document or article protected by this technology. Therefore, the item may not be copied by any available reproduction apparatus, and a manual process for reproducing a product with an identical fiber pattern of fibers have authentic characteristics is untenable.

One embodiment of the invention employs dichroic fibers, similar to those disclosed in U.S. Pat. No. 6,035,914 (Ramsey, et al., Mar. 14, 2000) and U.S. Pat. No. 5,974,150 (Kaish, et al., Oct. 26, 1999), expressly incorporated herein by reference. These fibers have properties that are readily distinguished from most types of imprinted patterns, and further may be dispersed in a non-deterministic manner on a substrate. Thus, fiber pattern in a substrate may be used as a basis for authentication.

A second embodiment employs one or more proprietary dyes which are withheld from public availability. These dyes may be selected having desired distinctive optical properties which are readily detectable. Therefore, by detecting the spectrographic properties of the dye, the object on which the dye is deposited may be authenticated. The particular dyes employed may not be critical, but rather that the dyes have limited availability and distinctive characteristics.

In one embodiment, the random fiber pattern is illuminated by a light source and imaged by a high-speed scanner during the production process. The fibers may have particular and distinctive optical characteristics, such as fluorescence, dichroism, particular spectrographic characteristics, or the like. A polarized light source, for example, may be used to cause a proprietary dye in each fiber to fluoresce. In this case, a fiber (or other element) bearing the wrong dye, or in the wrong position or orientation, would be detectable. Further, the scheme is extended to include a plurality of fibers (or other elements) over a region, in which the various fibers must each meet authentication criteria. The fibers need not be identical, though for different types of fibers, different detection conditions may be required, a possible advantage, but also a possible cause of complexity. For example, the density and characteristics of the fibers in the region, and the selected validation/authentication criteria may be established to define a probability of an occurrence of duplicate encoded patterns of $<10^{-15}$. An image of this pattern is then encoded (including information such as the position, number and orientation of each fiber, and as necessary, the distinctive characteristics) as an encrypted digital signature, which is printed on a label, for example as a code, bar code, or other identifier. In the encoding process, it may often be presumed that the label is authentic, and therefore the authentication of the fibers or other elements may be dispensed with or minimized; however, in other cases, the fibers or elements may be fully authenticated, for example by their spectrofluorometric characteristics, as a part of the initial encoding process.

This code number is generated by a secure algorithm, i.e., the algorithm itself is unknown and not determinable and/or the algorithm uses a secure technique which prevents a prediction of the output based on the input, e.g., a one-way trap door function. This means that the generated code can be self-authenticating—the fibers or other elements are authenticated as being of the correct type, and the positions are determined, a compressed vector defined, and passed through a corresponding algorithm, such as a cryptographic hash function. If the result of the hash function at the time of authentication corresponds to the originally encoded pattern, then the object bearing the fibers or other elements (which are preferably integral to the object) is authenticated. If the authentication fails, this probably means that the fiber pattern is incorrect, possibly as a result of counterfeiting. Error tolerance may be obtained by preprocessing the original scanned pattern to normalize feature metrics, and encode a set of likely altered results, thereby permitting authentication of any of the set of likely altered results, without substantially leaking the original pattern.

Alternately, the algorithm may represent a reversible algorithm, in which the code defines the original pattern, and therefore a statistical deviation of the original pattern from the putative pattern to be authenticated may be determined. Normally, the use of a reversible algorithm would be discouraged; however, since in this case a physical authentication process is also imposed, the result is a theoretically weakened security, and not a full breach.

The code on the article is preferably a machine-readable printed or inscribed code (e.g., laser marked, ink jet printed, impact printed, laser printed, etc.), such as a 1-D or 2-D barcode, or the like, though alphanumeric characters may also be employed. At any interrogation point, an inspector can non-destructively validate the pattern and authenticity of the article with an appropriate scanner. The document is authentic only if the code appearing on the scanner display matches the one printed on the document. For travel and identity documents (as well as for other applications), wired or wireless connection to a database for a further level of security may also be used. Thus, for example, the code may be stored in a radio-frequency interrogable device (e.g., RF-ID) or a contactless or contact smart card.

The result is a multi-level security system based on random and non-reproducible physical characteristics of the physical fiber (or other element) arrangement, a determination of that the fiber (or other element) is authentic, and secure encryption technology. The verification process is stand alone, since the scanner is verifying a code match that could only be produced at the secure production site, but can be integrated in an existing reader infrastructure. It is noted that the physical authentication of the fibers need not be integrated into the authentication of their position and/or orientation. Thus, the position and orientation may be determined by a normal camera, and need not be determined, in every embodiment, with an imager capable of authenticating the fibers or other elements. This, in turn, permits the fiber or element position and orientation to be determined using a typical camera or imager used to read bar codes (1D or 2D), and indeed a bar code may be overlaid on the fiber or element pattern to avoid a need to reposition the imager. The physical authenticity of the fibers may then be determined using a separate device, such as a non-imaging spectrofluorospectrometer. Since the position of all optically visible elements is determined by imager, if the proper spectrofluorometric characteristics are received from the imager field of view, then the fibers or other elements present in that view can be authenticated for both position and spectral characteristics. Thus, in one embodiment, a fluorescence signature is obtained using a one or more LED or laser diode illuminators at selected wavelengths, detected by one or more photodetectors which may have particular filters. For example, if the X-max absorption of the fiber is at 590 nm, and fluorescent emission at 650, the authentication system could have LEDs which illuminate at 585, 590 and 595 nm, and photodiodes with filters to respond at 645, 650 and 655 nm. Thus, deviation in the fluorescent characteristics can be readily detected for the set of fibers. In the case of dichroic fibers, a pair of LEDs with crossed polarizing filters may be provided to illuminate the imager region. The imager will register a differential response for each fiber based on its dichroic characteristics, thus distinguishing simple printed patterns which typically display no net dichroism.

In a fashion similar to that used in the currency paper of the United States and other fiber-based security papers, the optically readable elements (e.g., fibers) are randomly dispersed in a document, which is then processed to become, for example, a passport, travel document, ticket, or other original document for which the authenticity must be determined. This can be on all pages of the document, selectively distributed pages, or solely within the cover of the document. While placement may play a role in the overall security afforded by integrating the anti-counterfeit solution into the travel document, one logical place for these features to be authenticated would be near the position wherein the traveler photograph and/or other identification form of credential is located. This would enable coincident interrogation of existing biometric and/or radio frequency identity chip technology. Considering that the issues of cloning of the radio frequency identity chip or duplication of biometric information have been publicized, raising some questions about the integrity of such security features, incorporating this authentication scheme into the substrate provides the ability to confirm the authenticity of the document itself, perhaps even prior to the query of the traveler identity feature.

The techniques according to the present invention are not limited to the preferred embodiments, and therefore various known security features and techniques may be employed to provide a secure authentication system.

The present invention also provides authentication apparatus for verifying authenticity of media according to the present invention.

In the case of a dichroic fiber, the authentication system provides an optical system that reads an optical image of the fibers while a polarization property of incident light is varied. The light from the fibers is then analyzed to verify that the pattern results from fibers having dichroic properties. The pattern of the fibers is then compared with a pattern determine during a pre-authentication step, which may be stored in an encrypted message imprinted on the media, or stored remotely and recalled during an on-line authentication procedure.

In order to provide improved authentication and avoidance of counterfeiting the present invention utilizes fluorescent dichroic indicators. Materials that are dichroic may have different absorption coefficients for light (i.e., electromagnetic energy, typically ranging from infrared to ultraviolet wavelengths) polarized in different directions. When the energy of the incident photon (polarization) corresponds to the absorption transition of the molecule, the interaction between the absorbing dipole and the incident photon is largest and high absorption of incident photons is observed. This energy is, for example, re-emitted by a fluorescent molecule with the plane of polarization of the emitted photons aligned with the emitting dipole of the fluorescent molecule. Most molecules have the absorbing and emitting dipole approximately collinear. When the polarization of the exciting light is collinear with the absorption dipole, the fluorescent emission will be highest. Light polarized normal to the absorbing dipole, on the other hand, is not absorbed to a great extent; hence, the resulting emitted intensity from this absorption is low. Where the light source is not polarized, the dichroism of each fiber will result in respective polarized reflection, transmission, and emission.

According to a preferred embodiment, an authentication indicator comprises a dichroic material. Preferably, the dichroic material will exhibit a high degree of dichroism. It is not important, however, in what form the dichroic materials are introduced into the media being authenticated. For example, there may be situation where authentication is facilitated by using dichroic indicators in the form of ribbons, rectangles, pyramids, spheres, etc. As long as the indicator's dichroism is reasonably preserved during formation of the article (i.e., incorporation of the dichroic indicators with the article), the shape/form of the dichroic indicator is not important.

A preferred form for the dichroic indicator is a fiber. Fibers may advantageously be used to incorporate the desired dichroic behavior into the article since fibers may be incorporated within many processes without detriment to the process (e.g., paper making, weaving, sewing) or dichroic fiber. The fibers may have widely varying cross-sections and lengths. Essentially the only requirement is that the configuration of the fiber not disrupt the underlying manufacturing process (e.g., with aerosol applications the fibers must be sufficiently small to be sprayed). Where otherwise feasible, the dichroic fibers are somewhat elongated since elongated fibers are easier to identify within a matrix of material and can potentially provide more data that shorter fibers (e.g., since different points along the length of a long fiber may be more or less obscured by paper fibers, be closer to or further from the paper surface, etc., and hence, exhibit more or less dichroism). Finally, in some circumstances it may be possible to use fibers of uniform lengths to provide easily verifiable data points—i.e., when inquiring whether a marked article is authentic, one can quickly see if fibers of appropriate lengths are present. Synthetic polymer materials are preferred for the fiber material, e.g., Nylon 6,6. A wide variety of acceptable indicator materials are available at very low cost. For example, polyesters, polyamides, poly(amide-imides) and poly(ester-imides) can be made birefringent. Examples of polymers used in preparing the stretched films having a positive intrinsic birefringence include polycarbonates, polyarylates, polyethylene terephthalate, polyether sulfone, polyphenylene sulfide, polyphenylene oxide, polyallyl sulfone, polyamide-imides, polyimides, polyolefins, polyvinyl chloride, cellulose and polyarylates and polyesters. Examples of negative intrinsic birefringence stretched films include styrene polymers, acrylic ester polymers, methacrylic ester polymers, acrylonitrile polymers, and methacrylonitrile polymers.

Suitable dyes, where necessary or desired, include naphthalimides, coumarins, xanthenes, thioxanthines, naphtholactones, azlactones, methines, oxazines, and thiazines. Rhodols, Rhodamines (See, U.S. Pat. No. 5,227,487, and U.S. Pat. No. 5,442,045), fluoresceins, and flavines are preferred for visible fluorescence. In using dyes, it should be apparent that instead of employing a single dye or modulating the content of a single dye, a plurality of distinct dyes may be added to the fiber matrix, potentially providing distinct and relatively orthogonal coding schemes. For example, Molecular Probes' Alexa dye series includes five fluorescent dyes, typically used to prepare bioconjugates. The absorption spectra of these five spectrally distinct sulfonated rhodamine derivatives—Alexa 488, Alexa 532, Alexa 546, Alexa 568 and Alexa 594 dyes—match the principal output wavelengths of common excitation sources, thus allowing multicolor coding. Of course, various other dyes or compatible sets of dyes may be employed.

Fluorescent resonant energy transfer (FRET) techniques may also be used to label fibers and detect labeling. It is noted that dichroism is not necessary, especially where a complex optical effect, such as fluorescence or FRET is present. Again, by combining techniques, more efficient coding and greater difficulty in counterfeiting fibers is provided.

The dichroic agent can be brought into association with the indicator in a variety of ways. In order to maximize the dichroism, the dichroic agents (e.g., molecules of dye) are aligned maximally; non-dichroism is achieved by a random distribution of dye molecules. Typically, the dye alignment is achieved by a stretching of the polymer matrix during manufacture, which alters an anisotropy and alignment of polymer chains. The dye is interspersed or linked to the chains, and thus is aligned simultaneously. If the fiber is selectively stretched, or selectively annealed after stretching, spatial variations in dichroism will be apparent. The dye may also be bleached, e.g., photobleached, in a secondary process. Since many dyes have a narrow band absorption, such dyes may be selectively bleached, allowing independent control over spatial dye concentration. Heating, or other annealing processes, are typically not selective, and alter the crystalline structure of the entire portion of the fiber. Such selective heating is possible, for example, with infrared laser diodes or even infrared LEDs.

Preferably, when simple fibers are used as the indicator, the dichroic marking material is aligned along the length of the fiber. In this way the fibers will have very different emission spectra (i.e., with respect to intensity) when excited with light polarized parallel versus perpendicular to the fiber axis, assuming the absorption dipole is along the fiber axis. In general, the absorption dipole of the fluorescent marking molecule will not be perfectly aligned with the fiber axis. This is permissible, but it is preferred that the absorption dipole is nearly parallel or orthogonal to the fiber axis.

Where more complex fibers are employed, preferably the transitions involve polarization rotation between extremes. For example, the fibers may be "squished" along 90 degree-displaced axes along its length. Other techniques may be used to selectively orient the molecules in the fiber, for example using magneto-optic recording techniques.

The marking material (e.g., a fluorescent dye) may be associated with the indicator material (e.g., fibers) during formation (i.e., the marking material may be incorporated within the indicator itself), or the marking material may be added to the indicator after formation of the indicator. For example, when fibers are used as the indicators and luminescent dye is used as the marking material a preferred method of assuring maximal dichroism (i.e., maximum coalignment of dye molecules) is to melt blend the fibers and dye and then stretch the fiber. With other fiber/marking dye combinations, it may be possible to achieve satisfactory dichroism without a stretching step, e.g., by dipping the fiber in a container of dye.

For example, when fibers are used as the indicators and luminescent dye is used as the marking material, a preferred method of assuring maximal dichroism is to melt blend the fibers and dye and then stretch the fiber. With other fiber/marking dye combinations, it may be possible to achieve satisfactory dichroism without a stretching step.

The preferred dyes in the present invention are luminescent (i.e., fluorescent or phosphorescent). More preferably, fluorescent dyes are utilized as the marking material. Phosphorescent marking materials may also be used, however. The appropriate dye for use in a particular application will depend upon the specifics of the situation. In general, most preferably a fluorescent dye is selected so that the dye's dichroism is maximized at the intended detector wavelength. The marking dye may be tailored to quite specific applications. For example, a dye that emits in the infrared portion of the spectrum may be used to create an authentication signature that is invisible to the eye yet easily detected with appropriate instrumentation.

The fluorescence signal is preferably provided by a fluorescent dye or pigment doped into the fiber polymer matrix, having a long major axis to align with the polymer chains of the fiber during the drawing process. Known dyes may be used, for example organic fluorescent dyes that have absorption and emission in the infrared to near-ultraviolet range. These dyes are also known for a variety of other uses, such as fluorescence microscopy, chemical detection and tagging, physical photon capture applications, and the like. A fluorescent dye or pigment must also be sufficiently stable, thermally, to withstand the fiber production process as well as uncontrolled environmental exposure. The required/preferred concentrations of dye track those utilized in fiber technology generally—i.e., no special processing is required to combine the indicator and marking materials—except for perhaps an added process step to coalign the dye molecules within/along the indicator fibers as discussed above. However, there are other optical methods that can be employed to achieve a similar authentication benefits using random patterns.

To duplicate labels containing the fluorescent dichroic fibers, a counterfeiter would need to, among other things: duplicate the fluorescent dye used (to produce the same emission behavior at the selected detector wavelength); use fibers of the same general length and shape; and produce counterfeit label stock having the same general number of fibers per a given area of paper. Any attempt to counterfeit the fiber-containing label through a printing-based process would fail since printing would not reproduce the fibers' dichroism, and even the fluorescence would be difficult to achieve.

Thus, at higher levels of authentication, the pattern of the fluorescent dichroic fibers is detected and archived during initial processing thereof (i.e., before the label is circulated). When a particular label is submitted for examination, a detector can be used to ascertain the fibers' position within the paper, as well as its dichroism, e.g., polarization angle, $.theta.$ A three-dimensional (i.e., x, y, $\theta$.) authentication mechanism can therefore easily be provided by using an imaging device, such as a CCD imaging array, with associated polarizer(s). This CCD imaging array may be an area array or line-scan array, the latter requiring a separate scanning system. The polarimeter may include fixed or rotating (variable) polarizers.

At a highest level of security and authentication, the marked label is measured before it is circulated to record the path (x, y), $\theta_\lambda$x,y (polarization angle at wavelength $\lambda$ at a position x,y) $A_\lambda$x,y (specific absorption at wavelength .lambda. at a position x,y), physical disposition of the fibers within the media (e.g., label). It would be very difficult to duplicate these parameters. This data, or a subset thereof, is formulated as a plain text message and encrypted into cipher text by an encryption algorithm, such as the triple 56 bit DES encryption algorithm or the RSA public key-private key algorithm. In the former case, the authentication requires a secure and trusted party, which holds a symmetric key. In the latter case, the public key is published, and may be used to decrypt the message to determine if it corresponds to the label characteristics.

The scanned pattern on the certificate is captured as a set of pixels, and represented internally in the image processor as an image projected on a surface, with the surface not necessary being constrained as a planar sheet. This processor may provide a raster-to-vector conversion process. The printed code is also imaged, and captured by the processor, for example by optical character recognition, bar code recognition, pattern recognition, magnetically ink coded recording (MICR) reader, or other known means. The projected image is then compared with the ideal image represented by the code printed on the certificate. A stochastic analysis is performed of the types and magnitudes of any deviations, as well as correlations of deviations from the ideal. The deviation pattern, as well as any other deviations from the encoded patterns, which for example represent lost or obscured fibers, noise, environmental contamination with interfering substances, errors or interference in the original encoding process, etc., are then used to determine a likelihood that the certificate itself corresponds to the originally encoded certificate. Thus, the determined authenticity is associated with a reliability thereof, based on stochastic variations in the properties of the authentication certificate and stochastic variations in the generation of the associated secure code. A threshold may then be applied to define an acceptable error rate (false positive and false negative) in the authentication process. The reliability of the authentication or a go/no-go indication is then output.

In order to avoid the requirement for encrypting an entire or substantial portion of a representation of an image of the certificate, the medium may be subdivided into a plurality of regions, each region associated with a vector, which, for example is two-dimensional or of higher dimensionality. The vector, which represents an irreversible compression of data derived from the region, is then encoded and encrypted in the encrypted message. For verification, the vector mapping is decrypted and unencoded from the recorded message. The medium is then scanned, and an analogous vector mapping derived from the newly scanned image. The recorded vector map is compared with the measured vector map, allowing a correlation to be determined. In this case, given the large number of degrees of freedom, e.g., a polarization vector for each region or zone, even relatively large deviations between the recorded and measured vector maps may be tolerated in the authentication process. Thus, an initial deskewing and dewarping algorithm may be use to initially align the regional boundaries to achieve maximum cross-correlation. Such algorithms and image processing systems are known in the art. A cross correlation of even 0.1 over tens or hundreds of degrees of freedom may be sufficient to allow highly reliable authentication with a low number of false positives and false negatives.

The label may thus be subdivided into a plurality of zones, each associated with an encrypted code portion. In this case, since each subdivided zone stands alone, any such zone or set of zones with sufficient degrees of freedom may be used to authenticate the entire label. Where the zones are small or have a limited number of degrees of freedom, the reliability of authentication of the entire label by any one zone may be insufficient. Therefore, a plurality of zones may be authenticated, with each authenticated zone adding to the reliability of the resulting authentication. Any zones that fail to authenticate may also be weighted into the analysis, although typically with a lower weight than zones that correctly authenticate.

The present invention therefore provides systems and methods employing self-authenticating and on-line authenticating schemes, allowing determination of object authenticity by evaluation of a non-duplicable and essentially random pattern.

More specifically, one aspect of the present invention provides a method and apparatus for the production and labeling of objects in a manner suitable for the prevention and detection of counterfeiting, which includes a recording apparatus containing a recording medium having macroscopically detectable anisotropic optical properties.

In a dichroic fiber embodiment, a plurality of dyes may be employed within the fibers, either using multiple dyes in a single fiber, or a plurality of fiber types, each having different dye properties. Each dye, having a distinct absorption and fluorescence spectrum, is separately detectable. Further, the respective dye concentrations may be varied during the manufacturing process, or later selectively bleached by, for example, a laser at an absorption maximum wavelength of a particular dye species. The dichroism may also be varied, for example by controlling a stretch process during fiber production, or by heating the fiber above a recrystallization point with, for example, a laser. Thus, for example, using commonly available three-color image detectors (in conjunction with an appropriate optical system), three separate dyes may be detected, providing additional degrees of freedom for an authentication scheme. It is noted that, while dichroic fibers are preferred, it is not necessary for each dye to be associated with a dichroic property or a distinct dichroic property. Thus, the dichroism, fluorescence, and absorption and/or transmission characteristics may potentially be distinct characteristics of the fiber.

In another embodiment of the invention, microspheres or other shaped objects are provided having dichroic properties. In this case, the data map includes the position and polarization axis orientation of the objects, which it should be understood is a three dimensional vector in the case of a linear fluorescent emission axis from a dye and a two dimensional vector in the case of a radially symmetric fluorescent emission from a dye. Advantageously, these objects may either be embedded in the stock or applied later, using a printing process, for example lithography, ink jet printing, specialized laser printing (with care taken to avoid undesired changes to the dichroism in the fuser), and the like.

According to one embodiment of the invention, dichroic fibers are formed of nylon having a fluorescent dye mixed into the polymer matrix. During the forming process, the fiber is stretched, which tends to align the molecules along the stretch axis. This anisotropic characteristic lead to dichroism, which differentially affects light of varying polarization axis. Therefore, due to this differential effect, the fiber will have a light polarization rotation, especially at wavelengths corresponding to the absorption and/or emission of the fluorescent dye. It is noted that the nylon itself may also be dichroic, but typically the effect is not easily observed at visible or other easily measured wavelengths; on the other hand, the dye is specifically selected to have useful optic interactions and to obtain a high degree of anisotropism under the process conditions.

The preferred nylon dichroic fibers allow for a number of identifying variations, for example the amount or type of dye in the fiber, optical, heat, physical or chemical (e.g., chemical or photo-bleaching, heating, stretching or fiber deformation) modifications of the fiber during or after fabrication, or after placement in an identifying substrate. As can be seen, a number of degrees of freedom are possible, providing a number of strategies for detection and making duplication difficult. The preferred variations are the amount of dye and physical stretch, both of which can be controlled, early in the manufacturing process of the fibers. Preferably, these two variations are provided over relatively short distances, for example millimeter ranges or smaller, providing a relatively high information-carrying capability, and this allowing relatively short lengths of fiber to provide sufficient information to identify the substrate.

Alternately, a modulated laser may be used to modify the fiber, to alter the dye and/or molecular chain organization. Such laser coding can be applied on a physical scale of microns, and can be controlled to tight tolerances. Fibers may also be used which are selectively sensitive to environmental conditions, such as temperature, humidity, gasses, and the like, so that a change in characteristics, e.g., optical characteristics, is measured based on a change in such conditions. Thus, for example, a document is provided with fibers that change in color with respect to temperature, humidity, or pH. The document is then analyzed in two or more different states, and the differential response recorded. It is noted that, in order to change pH, an acid gas soluble in the fiber, such as hydrochloric acid, acetic acid, moist carbon dioxide or ammonia, is provided in the environment. Other types of dye indicators are also known.

According to another feature of the invention, an authentication feature of a certificate degrades over time or environmental exposure, making long-term persistence of authentic documents in the market more difficult. Such a component is, for example, a dye or additive that degrades with ambient light or oxygen exposure under normal conditions, or even is the result of a progressive internal chemical reaction, for example due to a catalyst dissolved in the fiber matrix. Of course, this degradation limits the ability to inventory and ship normal stock that are intended to be deemed authentic after a long period of time, and compels expedited authentication. However, for applications where a short time window is appropriate, such "self-destructing" anti-counterfeit technologies may be appropriate.

The present invention also provides a recording apparatus capable of imprinting a desired dichroic pattern on a substrate. This pattern, therefore, could be authenticated by means similar to that provided for fibers. In distinction to fibers, imprinted patterns would be pixelated, on the surface of the medium only, and have very limited dichroic properties. A visual examination would also reveal that the pattern was not due to fibers. Thus, a careful examination could distinguish the methods. However, this allows the use of a common reader device to authenticate distinctly different certificates.

The recording apparatus provides at least two transfer films, having the appropriate dichroic properties, which are selectively deposited on a substrate in a microscopic pixel pattern, to yield the desired pattern.

It is noted that, according to the present invention, the optical properties of the fibers or dyes need not be in a visible optical range, and therefore infrared reactive dyes may be employed. Two advantages result from the use of infrared dues and detection equipment. First, the pattern may be spatially coincident with a visible graphic, thereby increasing spatial utilization efficiency. Second, infrared laser diodes and light emitting diodes are less expensive that their visible counterparts, and are available in various wavelengths; and simple silicon photodiode detectors are appropriate.

According to an embodiment of an authentication device, a tag is provided having visible from a surface thereof a low density non-deterministic dichroic fiber pattern, and a machine-readable code defining the fiber pattern. The authenticity of the tag is therefore dependent on a correspondence of the machine readable code on the tag and the actual fiber pattern on the tag.

The preferred dichroic fibers have a relatively narrow optical absorption bandwidth to excite fluorescence, and therefore require either a carefully selected narrow-band source, such as a laser diode or light emitting diode, or a broadband light source, such as an incandescent lamp. In the case of a broadband source, in order to maintain a high signal to noise ratio, a filter is preferably provided to limit emissions near the fluorescent wavelength.

For example, a narrow band diffraction filter, e.g., 565 nm, passing light at the absorption maximum may be provided to filter the light from a xenon incandescent bulb.

The optical sensor system also includes a filter to pass the fluorescent light emitted from the fibers, but block other stray light. For example, a red, e.g., 620 nm pass, Ratten filter may be used.

In order to detect the dichroism, a rotating polarizer may be employed, while capturing images during various phases of rotation. Typically, the fibers have a dichroism closely related to the physical axis of the fiber. By detecting dichroism, therefore, the existence of a fiber as compared to a normally imprinted indicial may be determined. The detection of dichroic features also advantageously allows digital background subtraction.

Typically, the fibers have a uniform cross section, and thus the significant data included in a fiber pattern is the endpoints and path of the fiber. This information may therefore be efficiently coded, and indeed, much of the information may be truncated without substantial loss of system security.

The tag preferably has a bar code imprinted thereon with self-authenticating information and a serial number. A bard code reader in the authentication device therefore reads the code. The self-authenticating information is then compared with the detected fiber pattern to determine a correspondence thereof. This correspondence may be based on a normalization transform, to account, for example, for image skew or other artifacts. Further, since the tag is subject to change due to environmental factors, an acceptable error rate or fuzzy match correlation may be defined, to avoid false negatives, while maintaining an appropriately high level of security.

The present invention may also be applied to the authentication of optical recording media. According to a first embodiment, an optical disk is provided with a measurable random error rate due to physical imperfections in the optical recording medium. While presently, manufacturing techniques are such that the error rate is low, the base error rate may be artificially increased by inserting impurities in the resin used to form the media, for example a polycarbonate resin. One type of impurity is air-filled glass microbeads (3M) which would have the effect of dispersing light between the read laser and the information pattern, this resulting in random bit errors.

In data recording media, error detection and correction techniques would likely be able to counteract the effects of such defects. On the other hand, in musical compact disks (CDs), which do not employ error detection, such random errors would likely have little effect on the reproduced sonic quality, due to the presence of digital and analog filters in the signal path.

According to the present invention, the position of the defects may be encoded, and therefore verified. It is possible to record a on-off code on a CD, for example by selectively metalizing or demetalizing a circumferential band of the disk in a binary data pattern, which could be read by the read head as a bar code. Demetalization could be effected, for example, by a carbon dioxide laser ablation pattern. The defect data pattern and code are intercepted, for example, at the output of the optical detector or as a component of a digital filter processing the output of the optical sensor. Firmware within the CD player determines a correspondence of the code with the actual defect pattern on the disk, and may block playback of disks that lack correspondence. The player may also use error correction based on the encoded defect locations to counteract the effect of the defects on the signal.

These disks are backwards compatible with existing players, since the errors are generally effectively filtered.

While it is preferred to employ the existing optical pickup of the optical disk drive to read the disk defect characteristics, it is also possible to employ a distinct system. For example, the encoding may be placed partially or entirely on the non-data reading surface of the disk. This encoding may be read within a disk player or separately. For example, a simple LED and photodiode may be provided to read a non-deterministic pattern and code formed on the back of the disk, along a single circumferential path. The non-deterministic pattern may be, for example, a surface roughness or irregularity, a pattern of ink drops or fibers dispersed in a graphic ink, or the like. The code may be simply printed using existing contact or non-contact techniques.

It is a feature of the present invention wherein an excitation source may be employed, the excitation source being a bright light source, such as a xenon incandescent bulb, with a narrow band diffraction filter approximating the absorption maxima filtering said light.

It is an object of the present invention to provide, wherein optionally the absorption and emission wavelengths are narrow, a broad-band receiver having a cutoff filter to block exciting light.

It is a feature of the present invention wherein a polarizer is provided between said broad band receiver and a sample, which rotates between successive exposures, wherein over a half-rotation of said filter, two or more exposures are taken, such that by employing digital background subtraction, the dichroic fibers, which show maximum variance with respect to rotational angle of the filter as compared to background signals, are extracted.

According to the present invention, the label or certificate may be provided with codes having a multiplicity of levels. Thus, even if a first level code is broken, one or more backup codes may then be employed. The advantage of this system over a single level complex code is that the complexity of the detection devices used in the first instance may be reduced, and the nature and even existence of the higher level codes need not be revealed until necessary.

In order to prevent mass duplication of labels or certificates, it is preferable to encrypt and print a code representing varying characteristic of the label or certificate. In verifying the code, the associated characteristics must correspond. Such a system adds markedly to the complexity of any counterfeiting scheme, while still allowing labeling or goods and production of certificates to proceed. In a simpler system, the mere repetition of supposedly random or pseudorandom codes is detected, indicating simple copying.

In order to prevent the replacement of an authentic label on a different item, a unique, random or quasi-unique characteristic of the item is encoded on the label. In this way, relocation of the label to other goods may be detected.

In order to provide robustness against encryption cracking, a plurality of encoding schemes may be employed, for example to avoid complete system failure if one of the encoding schemes is "broken". For example, three different codes may be provided on the certificate, employing three different algorithms, and potentially based on three different sets of criteria.

Preferably, the encoding and authentication employ a system which prevents tampering, reverse engineering or massive interrogation, which might lead to a determination of the underlying algorithm and/or the generation of valid codes for counterfeit goods. Thus, for example, a secure central server may provide authentication services, over secure communications channels.

Self-authentication may be based on a public key algorithm, however, unless this algorithm is highly secure, this is not preferred for high security applications, but may be acceptable in moderate security applications. The risk is that if the private (secret) encryption key is discovered or released, the usefulness of the encoding is lost, and further, until the pool of authentic goods bearing the broken encoding is depleted, counterfeiters may continue undetected. Self-authentication schemes are subject to sequential cracking attempts until the code is broken; once an authentication code (private key) is discovered, it may be used repeatedly.

It is noted that the imprinted code on the certificate need not be visible and/or comprehensible, but rather may itself be a security feature. Thus, special inks, printing technologies, or information storage schemes may be employed. Preferably, proprietary dyes having unique detectable optical signatures are employed.

Another embodiment of the invention provides an authenticatable sealing tape. The tape is imprinted with a machine readable code, which, for example, uniquely identifies the tape portion at repetitive intervals, e.g., every 2 inches. The tape also includes a set of fiducials as physical landmarks and a dichroic fiber pattern, for example due to a low density of fibers adhered to the adhesive side of the tape in a non-deterministic pattern. The tape is tamper evident, such that if the tape is cut or removed, evidence remains of this tampering.

Prior to spooling, the codes and associated fiber patterns are recorded in a database.

When applied, the contents of the sealed container are identified, and the tape identification scanned, with the contents thereafter associated with the identification of the tape. During authentication, the tape is again scanner for identification and fiber pattern, which is then authenticated on-line to ensure authenticity.

While the tape may also be self-authenticating, this poses the issue of false positive authentications if a spool of tape is stolen, since the imprint on the tape does not relate to the contents of the sealed container.

One embodiment of the present invention thus solves the above noted problems and overcomes suboptimizations inherent in the prior art by providing an authentication mechanism utilizing fluorescent dichroic fibers. The fibers are randomly and non-deterministically embedded into or form a part of a substrate. This means that by studying any one substrate, the pattern in any other substrate, and therefore a code representing that pattern, is not made apparent. This pattern may be stored in a database with an identification of the substrate, indexing the stored characteristics of the substrate, and/or encoded on the substrate with an imprinted encrypted code.

The preferred system incorporates a sheet of material, the authentication certificate or label, impregnated with dichroic fibers containing a fluorescent dye, which combines to form a high security system to thwart counterfeiting in a wide range of applications. Dichroic polymer fibers may also form part of the object to be authenticated. These fibers are relatively difficult to produce, and their embedding into paper or woven goods requires special equipment. Further, these fibers are observable with the naked eye, discouraging low sophistication attempted counterfeiting of certificates without this feature. This system allows for instant field verification of labels while maintaining a high level of security against counterfeiting by making the reverse engineering process extremely difficult and expensive. No two labels are ever alike, yet they can be produced very economically. In order to determine if the imprinted code corresponds to the certificate itself, the fiber pattern, which is completely random, is illuminated by a light and read by a scanner. The resulting pattern is then compared to the encoded pattern to determine authenticity.

According to a preferred embodiment, the pattern on the certificate is represented as an image projected on a surface, with the surface not necessary being constrained as a planar sheet. Therefore, relative deformations of the certificate pattern may be resolved through mathematical analysis using known techniques. The relative deformations, as well as any other deviations from the encoded patterns, which for example may represent lost or obscured fibers, noise, environmental contamination with interfering substances, errors or interference in the original encoding process, etc., are then used to determine a likelihood that the certificate itself corresponds to the originally encoded certificate. Thus, the determined authenticity is associated with a reliability thereof, based on stochastic variations in the properties of the authentication certificate and stochastic variations in the generation of the associated secure code. A threshold may then be applied to define an acceptable error rate (false positive and false negative) in the authentication process.

To produce an informational level of security which allows authentication without accessing a central information repository (database), the location or particular characteristics of the dichroic fibers, which are random or unique, are determined, and used to generate an encrypted code, wherein the encryption algorithm key (or private key) is maintained in secrecy. Therefore, the code must match the dichroic fiber location or characteristics for authentication of the certificate. Since the dichroic properties provide a characteristic which existing duplication systems cannot control, the certificate with encoding is very difficult to undetectably duplicate.

According to another embodiment of the invention, fibers may be provided with spatial variation in patterns, such as dichroism, color, coating thickness, or the like, providing additional, and difficult to reproduce, degrees of freedom into the security scheme. These variations may be random or relatively unique, and, for example, may include enough information content to uniquely identify the object. For example, the polarization angle along the length of a dichroic fiber may be controlled by altering a "stretch" of the fiber during fabrication, or post modification, for example by laser diode heating to form a polarization angle pattern on the fiber which varies over distance. The pattern may be truly random, or pseudorandom, with an arbitrarily large repetition interval or have a regular pattern. In any case, as the fiber (either on the object or the certificate itself) is being encoded on an authentication certificate, the fiber is analyzed for the particular property, and this property and possible the relationship to other properties, used, in part, to encode the certificate. It is noted that the replication of such patterns on fibers is particularly difficult, making this a useful additional security feature beyond the mere presence of dichroic fibers.

As stated above, the fiber may be imparted with a varying dichroic characteristic by selectively dying or bleaching a fiber or by inducing dichroism by selectively stretching portions of the fiber. In one embodiment, a beam of light, e.g., a laser, may be used to excite and selectively bleach dye within the fiber, providing a system for "writing" information to the fiber. In another embodiment, the fiber or substrate is coated with a magneto-optic recording layer which is selectively heated above the Curie temperature and selectively subjected to a magnetic field to induce a measurable light polarization effect.

The fiber may be modified during or in conjunction with the manufacturing process, or at a point of use. When a laser is used to modify the fiber, it heat the fiber, thereby altering the alignment of molecules, and/or it may bleach the dye in the fiber, thus reducing the concentration of the fluorescent species. The laser may be driven in a regular pattern, a random pattern, a pseudorandom pattern, or in a chaotic state of operation. In the latter case, the inherent instability of the laser is employed. It is noted that, according to the method of VanWiggeren and Roy, "Communication with Chaotic Lasers", Science, 279:1198-1200 (Feb. 20, 1998), an information signal may be modulated onto the laser output and masked by the chaotic variations, providing an encrypted data signal. By replicating the state of a receiving system laser having similar characteristics, including parameters of operation and starting state, it is possible to decode the data from the output signal. See Also, Gauthier, D. J., "Chaos Has Come Again", Science, 279:1156-1157 (Feb. 20, 1998). Thus, for example, a serial number or other coding may be imparted to the fiber which would be difficult to detect or duplicate without knowledge of the encoding system parameters, providing an additional level of security.

The label formed with the fibers may be identified based on an identifying location of the fibers, and/or identifying characteristics of the fibers. The fibers may be randomly dispersed in a carrier material, at such density to allow reliable identification, but without obscuring identifying features. For example, the fibers may be mixed into pulp to form paper, such as in the process used for U.S. currency. The locations of the fibers are then determined, allowing a correlation between the fiber locations and the identity of the substrate.

The present invention thus encompasses a system that reads a unique characteristic of a label or certificate and imprints thereon an encrypted message defining the unique characteristic, making the label or certificate self-authenticating. Optionally, a unique or identifying characteristic of an object associated with a label or certificate may be further ascertained and printed as an encrypted message on the label, uniquely associating the label or certificate with the object. Preferably, the characteristic of the object is a random tolerance or highly variable aspect, which is difficult to recreate, yet which is comparatively stable over time so that measurements are relatively repeatable. Where the characteristic changes over time, preferably these changes are predictable or provide identification, such as of the date of manufacture.

As stated above, the authentication algorithm may compensate or take into consideration "normal" changes or deviations, thus minimizing rechecks or manual examination of the certificates or labels.

The labeling system therefore includes a reader, for reading the unique characteristics of the label or certificate, such as a polarization sensitive imaging device for reading a distribution of dichroic fibers embedded in paper, and optionally a device which measures an identifying characteristic of the object to be labeled, such as a dimension, tolerance, color, sewing or thread pattern, etc. This information is then encrypted using an algorithm, to produce an encrypted message, which is then printed in the label, for example using a dye sublimation or ink jet printer. The encryption is preferably a multilevel system, for example including a 40-bit algorithm, a 56-bit algorithm, a 128 bit elliptic algorithm, and a 1024 bit algorithm. Each message level is preferably printed separately on the label, for example, the 40 bit encrypted message as an alphanumeric string, the 56 bit encrypted message as a binary or bar code, the 128 bit elliptic encrypted message as a two-dimensional matrix code and the 1024 bit algorithm as a pseudorandom placement of dots of one or more colors on the face of the label. Alternately, the higher level messages may be encrypted by the lower level algorithms, providing a multiple encryption system. Preferably, each encrypted message corresponds to successively more detailed information about the label and/or the object, optionally with redundant encoding or potentially without any overlap of encoded information. This system allows readers to be placed in the field to be successively replaced or upgraded over time with readers that decode the more complex codes. By limiting use of the more complex codes, and release of corresponding code readers, until needed, the risk of premature breaking these codes is reduced. In addition, the use of codes of varying complexity allows international use even where export or use restrictions are in place of the reader devices.

The invention also provides a reader adapted to read the characteristic of the label corresponding to the encoded characteristic, optionally sense or input the characteristic of the associated object, and either manually or automatically verifies the printed code on the label. If the code verifies, the label and/or object are authentic.

Preferably, both the marking system and the reader have a secure memory for the algorithm(s), which is lost in event of physical tampering with the devices. Further, the devices preferably have a failsafe mode that erases the algorithm(s) in case of significant unrecoverable errors. Finally, the systems preferably include safeguards against trivial marking or continuous interrogation, while allowing high throughput or marking and checking of objects and labels.

Since the algorithm memory within the reader may be fragile, a central database or server may be provided to reprogram the unit in case of data loss, after the cause of loss is investigated. Any such transmission is preferably over secure channels, for example 128-bit encryption or so-called secure socket layer (SSL) through a TCP/IP communication protocol. Each reader and marking system preferably has a unique identification number and set of encryption keys for any communication with the central system, and a marking placed on the label indicative of the marking conditions, for example marking system ID, date, location, marking serial number, and the like.

Labels can be affixed to any number of consumer and high security application including, for example, CDs/software, designer clothes, wine, cosmetics, seals, video tapes, floppy disks, perfume, electronics, currency, cassettes, books, records, documents, and financial instruments.

The technologies may also be made integral with such objects.

It is therefore an object of the present invention to provide a recording apparatus which includes a recording medium, having anisotropic optical domains and a means for transferring a portion of the recording medium to a carrier, wherein a bulk portion of the recording medium has macroscopically detectable anisotropic optical properties.

It is also an object of the present invention to provide the aforementioned recording apparatus, wherein the recording medium contains a polymer having crystalline properties, wherein a crystalline domain of the polymer recording medium has anisotropic properties.

It is another object of the present invention wherein the aforementioned transferring means selectively controls an anisotropic characteristic of the recording medium.

It is a further object of the present invention wherein the transferring means selectively controls an axis of the anisotropic characteristic of the recording medium.

It is yet another object of the present invention wherein the carrier is a label adapted for attachment to an object.

It is yet another object of the present invention wherein the recording medium is transferred in a pattern defined by a cipher.

It is an object feature of the present invention wherein a message is encoded on the carrier that contains a self-authenticating description of the pattern.

It is yet another object of the present invention wherein the pattern contains a sparse distribution of recording medium on the carrier.

It is another object of the present invention wherein the pattern contains a predetermined pattern of anisotropic properties.

It is another object of the present invention wherein the recording medium comprises a fluorescent dye composition.

It is an object of the present invention to provide a recording apparatus which contains a recording medium, having anisotropic optical domains, and a print head adapted for transferring a portion of the recording medium to a carrier, wherein a bulk portion of the recording medium has macroscopically detectable anisotropic optical properties.

It is another object of the present invention wherein a recording method comprises the steps of providing a recording medium, having anisotropic optical domains and then transferring a portion of the recording medium to a carrier, wherein a bulk portion of the recording medium has macroscopically detectable anisotropic optical properties.

It is an object of the present invention to provide a method comprising imprinting an authenticatable pattern on a medium and accounting for the imprinting step in an accounting database. In other words, during imprinting, a cost burden may be allocated to the process, and charged on that basis. Alternately, an accounting may be based on the use of recording media, the later authentication process, on a flat rate per unit time, a sale of the equipment and consequent elimination of ongoing accounting, or other alternatives.

It is an object of the present invention to provide a system and method which defines a pattern of recording media on a carrier; authenticates the carrier based on a correspondence of a subsequently detected pattern to the defined pattern; and accounting for an authenticating step.

It is an object of the present invention to provide a method to produce an imprinted carrier, comprising the steps of providing a recording medium, having anisotropic optical properties; and transferring a portion of the recording medium to a carrier.

It is another object of the present invention to provide an authentication device that detects optical polarization patterns, and analyzes these patterns to determine an authenticity based on an expected polarization patterns.

It is yet another object of the present invention to provide an authentication device for authenticating dichroic element containing media, which emits a beam which may be split according to a polarization mode to produce a plurality of split beams, each said split beam interacting with the dichroic elements and being then separately imaged by an imager, or subjected to a dynamically changing polarization filter, with successive images captured by the imager.

It is another object of the present invention to provide a substrate which is self-authenticating based on a public-key method.

It is an object of the present invention to provide a business method wherein a proprietor may engage in a gainful business which includes the steps of (a) accounting for a transferring step in an accounting database thereof; (b) selling dichroic fiber stock; (c) selling self-authenticating labels; (c) selling label inscriptors; (d) charging service fees for the use of said inscriptors or algorithms contained therein; (e) selling authentication devices; (f) charging service charges for the user of authentication devices; (g) charging differential charges based on pass or fail of the verification; (h) charging differential charges based on a level of confidence requested by the user, either at the time of inscription or the time of authentication; (i) paying a set fee to a seller of said authentication system upon discovery of counterfeit articles.

It is another object of the invention to provide an authentication system which is deviance-tolerant, and wherein slight changes in the configuration of a substrate over time does not prevent authentication of an authentic substrate.

It is a further object of the invention to provide an authentication system having at least two layers of authentication, differing a respective degree of security.

It is still further object of the invention to provide an authentication system capable of employing at least two authentication techniques, a first self-authenticating technique, and a second on-line authenticating technique.

It is a feature of the present invention that the aforementioned authentication system provides an off-line (self-) authentication device communicating batch authentication data to a remote central server system for a higher level of analysis, wherein different encryption codes are employed locally and centrally, in order to improve the resistance of the system to security compromise, wherein the remote central server system may optionally employ a complete database of substrate identifications and a set of associated objects, thus confirming that valid substrates have not been authenticated multiple times.

It is a further object of the present invention to provide an authentication device comprising a bar code scanner to read a bar code imprinted on the substrate, and a polarization-sensitive reader for reading a dichroic pattern.

It is an object of the present invention to provide a hand-held device that contains a bar code scanner to read a bar code on an authenticatable carrier, including an encrypted pattern, and a polarization-sensitive reader for reading the encrypted patterns.

It is a feature of the present invention wherein a polarizer is provided between a broad band optical receiver and a sample comprising dichroic elements, which rotates between successive exposures of the optical receiver, wherein over a half-rotation of said filter, two or more exposures are taken, such that by employing digital background subtraction, the dichroic elements, which show maximum variance with respect to rotational angle of the filter as compared to background signals, are extracted.

BRIEF DESCRIPTION OF THE DRAWINGS

The invention will now be described with respect to the drawings of the Figures, in which:

FIG. 14A shows a flow chart detailing a method of authentication relating to the discs of FIGS. 8B and 9;

FIG. 14B shows a flow chart detailing an additional method of authentication for the discs of FIGS. 8B and 9, whereby a non-deterministic pattern is used;

DETAILED DESCRIPTION OF THE PREFERRED EMBODIMENTS

Figure 1:
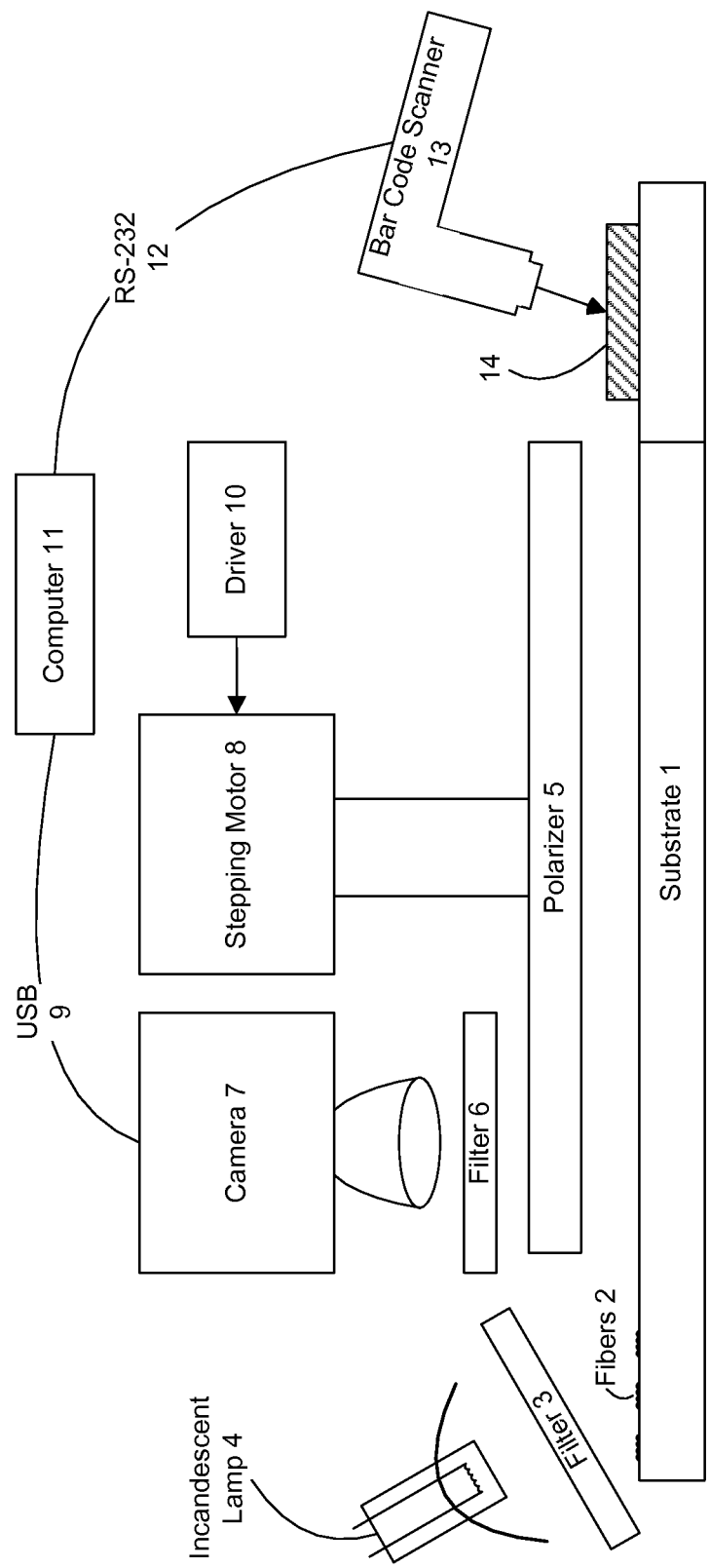
FIG. 1 is a schematic of the authentication process using a hand-held scanner according to the present invention.

The detailed preferred embodiments of the invention will now be described with respect to the drawings. Like features of the drawings are indicated with the same reference numerals.

In FIG. 1, a substrate 1 with dichroic fibers 2 located on it is subject to a filter 3 of an incandescent lamp 4. A polarizer 5 is beneath a filter 6 underneath a camera 7 and this camera 7 via a Universal Serial Bus (USB) 9 is connected to a computer 11 which is in turn connected to a bar code scanner 13 via a RS-232 standard serial port 12. The bar code scanner 13 scans the bar code 14 on the substrate 1 and completes the authentication procedure with the aid of the computer 11.

Figure 2:
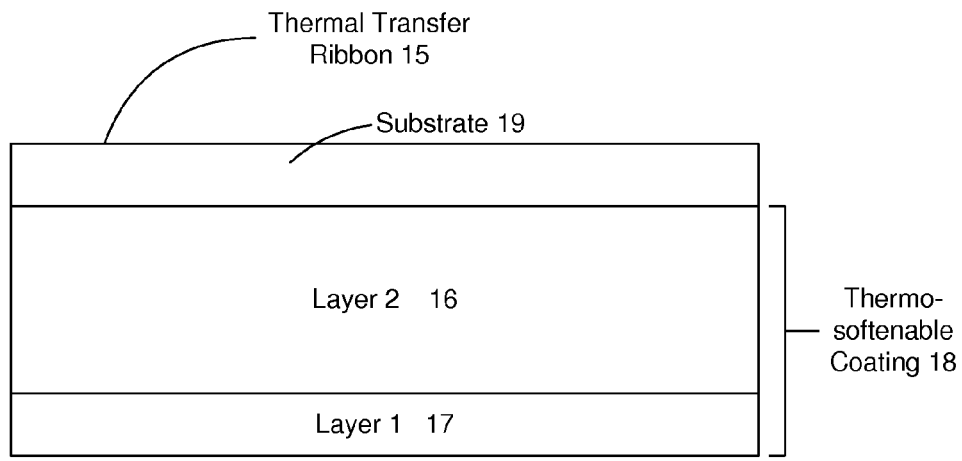
FIG. 2 is a thermal transfer medium before thermal transfer.

FIG. 2 shows a thermal transfer ribbon 15 comprising a substrate 19, and positioned on the substrate 19 is a thermosoftenable coating 18 which comprises a layer 16 and a layer 17. Layer 17 comprises a sensible material, e.g. binder compounds. Layer 16 is crystalline, and has a melting temperature above the printing temperature. Layer 17 contains polymers of selectively curable monomers and/or oligomers, to provide adhesion to the substrate. The melt viscosity and thermal sensitivity of layer 17 is determined by the melting points of the monomers, oligomers, polymers, thermoplastic binder resins and waxes therein and the amounts thereof in each.

Figure 3:
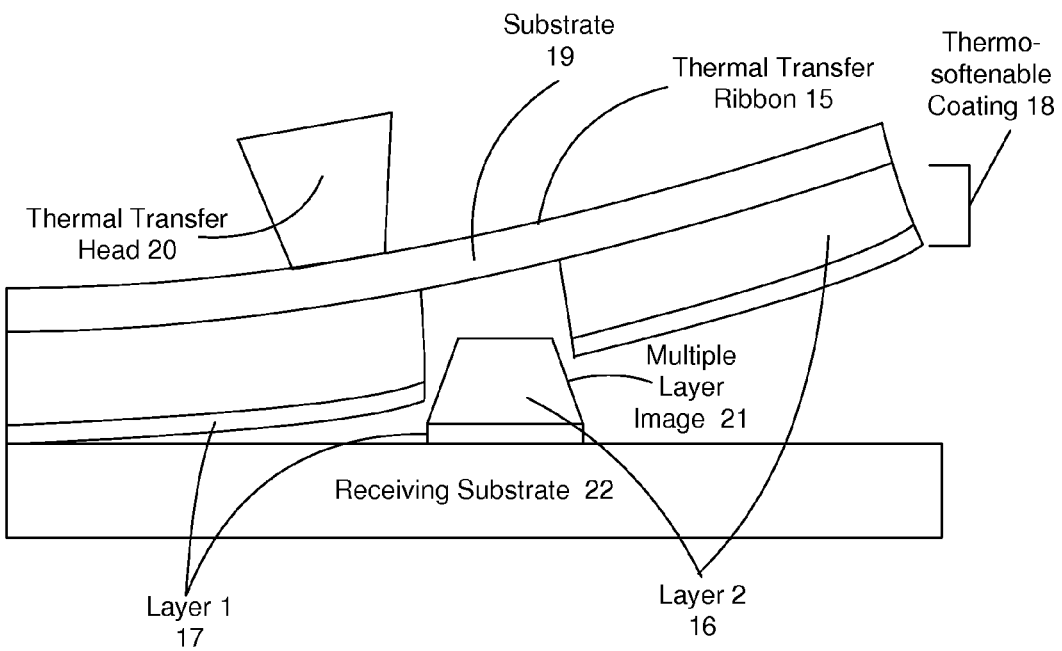
FIG. 3 is a thermal transfer medium of FIG. 2 in the process of forming an image by thermal transfer.

FIG. 3 shows a thermal transfer medium of FIG. 2 in the process of forming an image by thermal transfer. With lower melt viscosity values comes lower cohesion within the coating 18. Low cohesion allows for easier separation from the substrate 19. Exposure to heat from the thermal transfer head 20 causes transfer of both the layers 16 and 17 to a receiving substrate 22 without splitting layer 16 or separating layer 17 and layer 16 upon transfer, so as to form a crystalline layer 16 on top of an adherent layer 17. The layer 16, due to its crystallinity, has dichroic properties, which are retained intact through the process.

Figure 4:
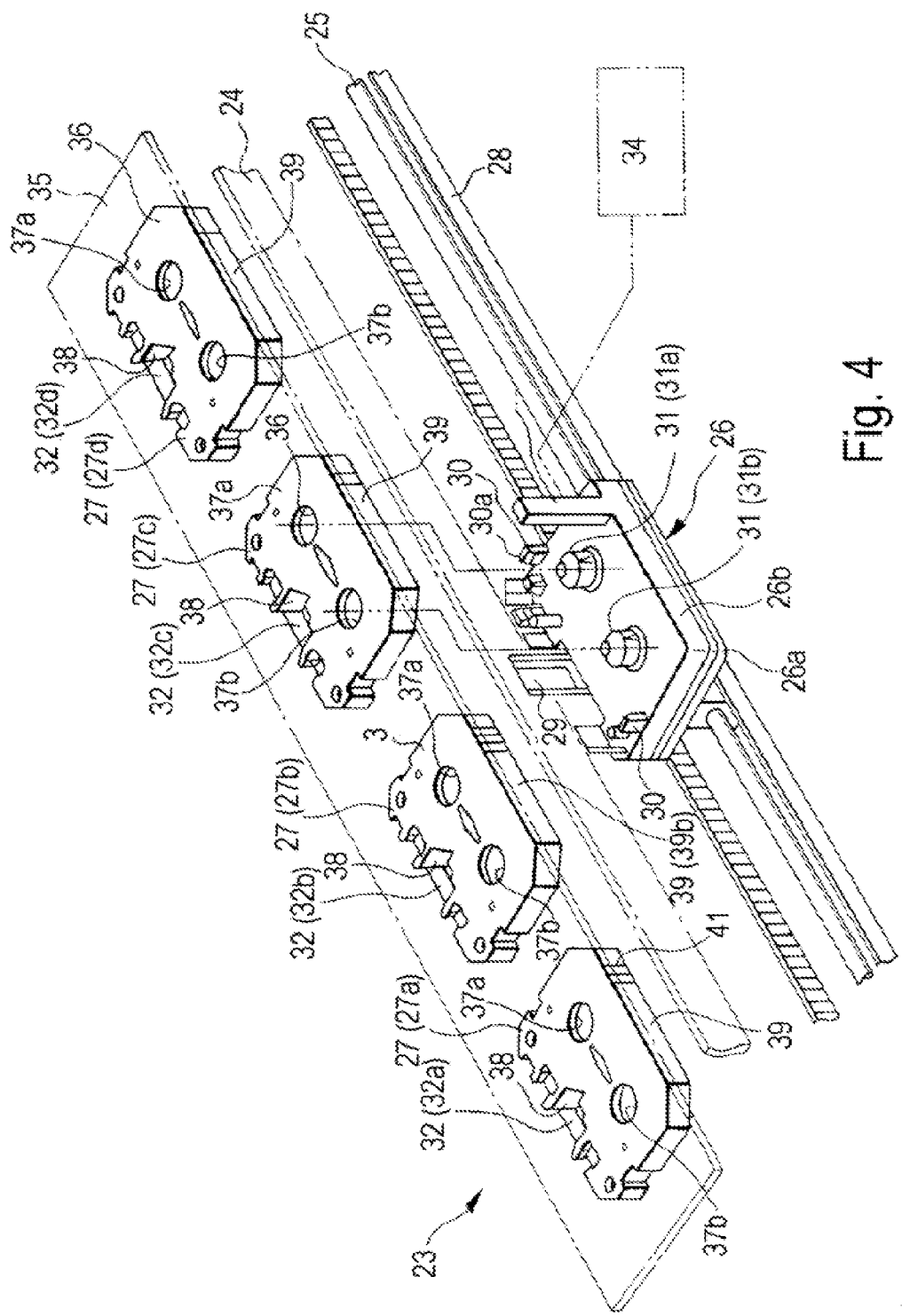
FIG. 4 is a perspective view illustrating the main portion of the pattern thermal transfer printer as contemplated by the present invention.

FIG. 4 shows a thermal transfer printer 23 with a platen 24 having the shape of a flat plate, arranged at a desired position, the recording surface of the platen 24 being oriented generally vertically. In a lower front side of the platen 24, a guide shaft 25 is arranged in parallel to the platen 24. The guide shaft 25 is mounted with a carriage 26 that is divided into an upper portion and a lower portion. The lower portion is a lower carriage 26a mounted on the guide shaft 25. The upper portion is an upper carriage 26b which is accessible, in vertical direction, to the lower carriage 26a mounted with a ribbon cassette 27(27n). The carriage 26 is reciprocated along the guide shaft 25 by driving a drive belt 28 wound around a pair of pulleys, not shown, with an appropriate driving device such as a stepper motor, not shown. The carriage 26 is arranged with a thermal head 29 opposite and accessible to the platen 24 to make recording on a sheet of paper, not shown, held on the platen 24 when the thermal head 29 is pressed the platen 24. The thermal head 29 is provided with a plurality of heat-generating elements, not shown, arranged in an array to be selectively energized based on desired recording information supplied via a host computer. Specifically, the carriage 26 has the plate like upper carriage 26b on top of the lower carriage 26a in a parallel movable manner such that the upper carriage 26b accesses the lower carriage 26a by a pair of parallel cranks (not shown). On the left and right sides of the upper carriage 4b, plate-like arms 30 are disposed in a standing manner with a space between equal to the width of the ribbon cassette 27. Each arm 30 has an engaging portion 30a at its top end being gradually bent inward. At the center portion of the upper cartridge 26b, a pair of rotary bobbins 31(31n) are arranged in a projecting manner with a predetermined interval between them. The pair of bobbins 31 allow an ink ribbon 32(32n) to travel in a predetermined direction. One of the bobbins 31 is a take-up bobbin 31(*a*) for winding the ink ribbon 32, while the other is a supply bobbin 31b for supplying the ink ribbon 32. An optical sensor 33 for detecting the type of the ink ribbon 17 accommodated in the ribbon cassette 27 is disposed on the carriage 26 at its edge away from the platen 24.

The optical sensor 33 is connected to a controller 34 disposed at a desired position of the thermal transfer printer 23 for controlling the recording operation and other operations thereof. The controller 34 is composed of a memory, a CPU, and other components, not shown. Based on a signal outputted from the optical sensor 33 while the carriage 26 is moving, the controller 34 at least determines or detects presence or absence of the ribbon cassette 27, the type of the ink ribbon 32 accommodated in the ribbon cassette 27, the travel distance of the carriage 26 relative to its home position, the open or close state of a canopy 35, and the distance between the pair of adjacent or separated ribbon cassettes 27.

The generally-plated canopy 35 is arranged over the carriage 26 spaced on a frame, not shown, such that the canopy can be opened and closed. In the closed state, the canopy 35 serves to hold down the paper at the exit of a paper feed mechanism, not shown. The canopy 35 has a length, along the carriage 26, generally equivalent to the travel area of the carriage 26. A plurality of cassette holders, not shown, for holding the ribbon cassettes 27 are disposed at predetermined positions on the canopy 35 at the side opposed to the carriage 26. By these cassette holders, the ribbon cassettes 27a, 27b, 27c, and 27d housing ink ribbons 32a, 32b, 33c, and 32d respectively of four different colors and/or dichroic axes, are arranged in a row along the travel direction of the carriage 26. The ribbon cassettes 27a, 27b, 27c, and 27d are selectively passed between the canopy 35 and the carriage 26b, and the cassettes are the same in shape and dimension regardless of the types of the ribbons 32. Each of the ribbon cassettes is composed of a generally flat and rectangular case body 36 made of upper and lower members in which a pair of rotatably supported reels 37, a pair of rotatably supported ribbon feed rollers, not shown, and a plurality of rotatably supported guide rollers facing a ribbon path are disposed. The ink ribbon 32 is wound between the pair of reels 37. The middle of the ribbon path for the ink ribbon 32 is drawn outside. The pair of reels 37, when mounted on the upper carriage 26b, provide the take-up reel for winding the ribbon used for printing and the supply reel for feeding the ribbon 32. A plurality of key grooves are formed on the inner periphery surface of each reel 37 in a manner of spline spaced from each other around the periphery. The inner periphery surface of one reel 37 provides a take-up hole 37a in which the take-up bobbin 31a is engaged. The inner periphery surface of the other reel 37 provides a supply hole 37b in which the supply bobbin 31b is engaged. On the surface of the ribbon cassette 27 opposed to the platen 24 when the ribbon cassette is mounted on the carriage 26, a recess 38 is formed to which the thermal head 29 faces. In this recess 38 the middle of the ribbon 32 is drawn. On the rear side of the ribbon cassette 27 running in parallel to the side on which the recess 38 is formed, an identification marker 39 is disposed for identifying the type of the ink ribbon 32 housed in each ribbon cassette 27.

Figure 5:
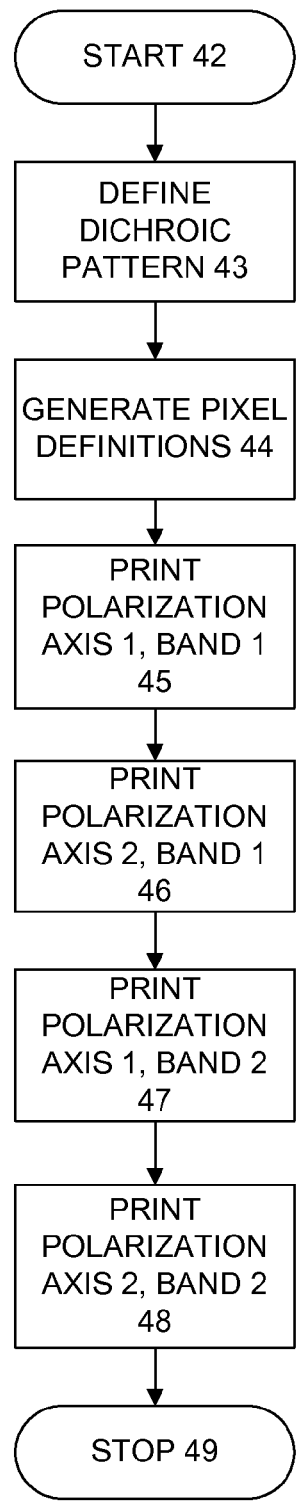
FIG. 5 is a schematic process illustration depicting the determination and reading of dichroic fiber polarization.

In FIG. 5, the start of the process 42 leads to the definition and determination of a dichroic fiber pattern 43 within a substrate or on a label. Next is the generation of a pixel definition 44 followed by printing polarization for axis 1 and band 1 45. Next print polarization axis 2, band 1 46, and then print polarization axis 1 and band 2, and axis 2, band 2, respectively, 47 and 48.

Figure 6:
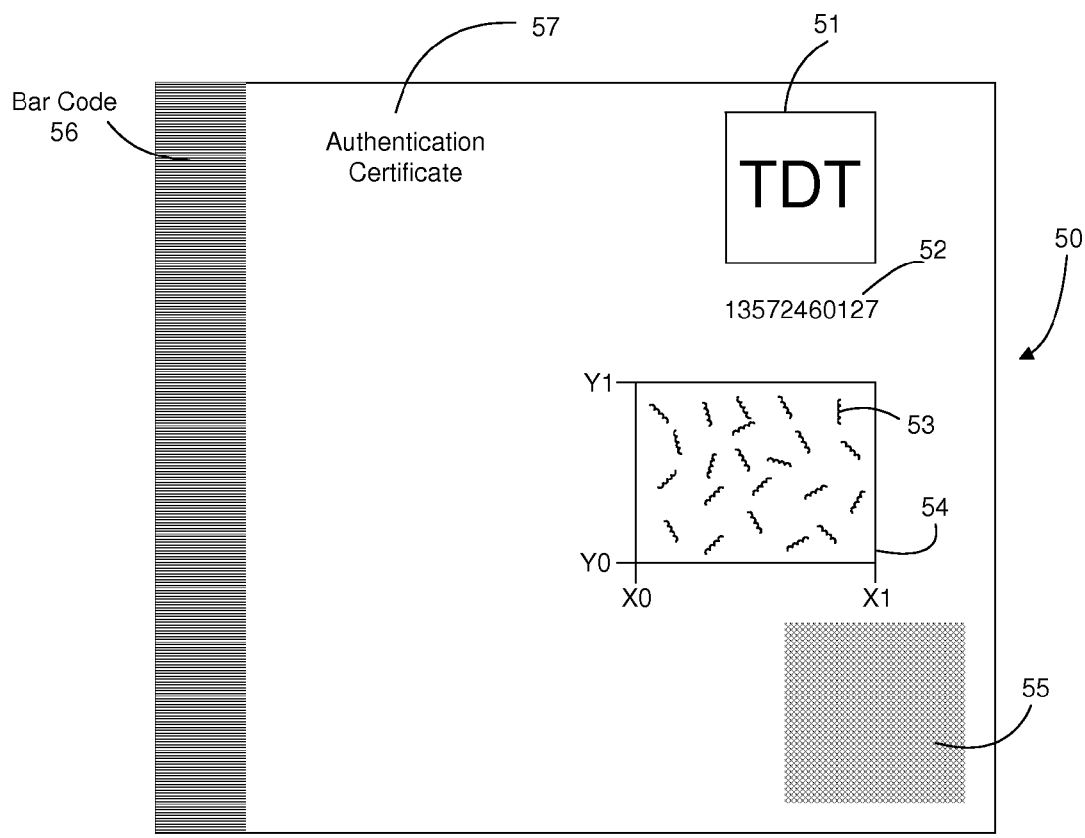
FIG. 6 is an example of an authentication certificate with several levels of security.

FIG. 6 shows an authentication certificate 50 with a bar code 56, a hologram 51 containing the logo of the respective entity employing such a certificate, a numeric representation 52 of the bar code 56, and a patch 54 containing randomly spaced dichroic fibers 53 along an axis $y_0$-$y_1$, and along axis $x_0$-$x_1$. Also included on the certificate is a glyph pattern 55, which is generally considered to be more aesthetic than the bar codes, and is designed chiefly for facsimile transmittal. Optionally the title of the document 57 can be included for an added measure of security.

Figure 7A:
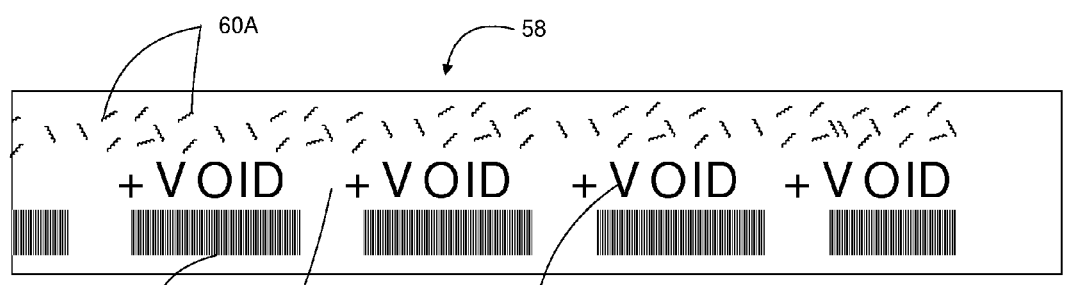
FIG. 7A is an example of authenticating bi-layer tape according to the present invention used to seal goods.

FIG. 7A is a tape 58 used to seal items vulnerable to tampering and counterfeiting such as cartons containing Compact Disc jewel boxes and other valuable merchandise. The tape is itself a bi-layer so that if the tape is attempted to be removed, usually in an inappropriate situation, the bottom face, selectively adhered at distinct points 60 to the item, will expose a visual cue 61 that the item has been tampered with. Also included is a bar code 59 for an added degree of security, which corresponds to the random pattern of dichroic fibers 60A dispersed throughout.

Figure 7B:
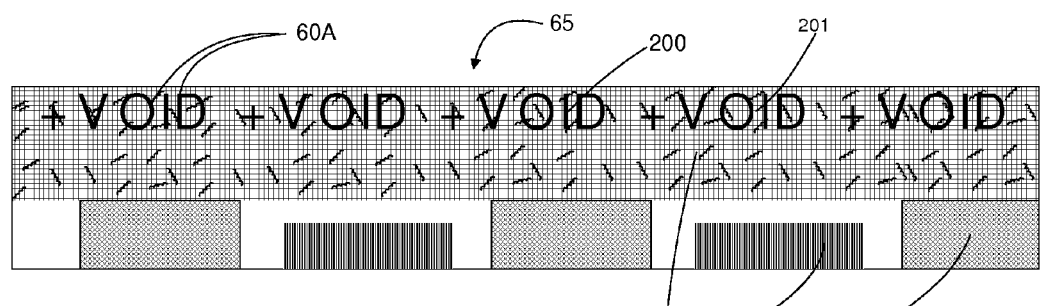
FIG. 7B is a view of the tape of FIG. 7A with the top portion removed.

FIG. 7B shows an authenticatable tape 65 subject to more rigorous security. A grid 200, 201, is printed on the tape to provide fiducial guidance to for detecting a fiber pattern 60A. The tape 65 also has imprinted a serialized bar code 62 and a 2-D bar code 63. The bar code 62 allows on-line authentication, identifying the tape 65 portion, while the 2-D bar code 63 allows self authentication based on the existence of difficult to forge dichroic fibers 60A, in a non-deterministic pattern, formed, for example by allowing fiber dust to settle on the surface of the exposed adhesive of the tape. As in FIG. 7A, the tape 65 is tamper evident, with, for example, a visible message 64 when the tape is lifted.

Figure 8A:
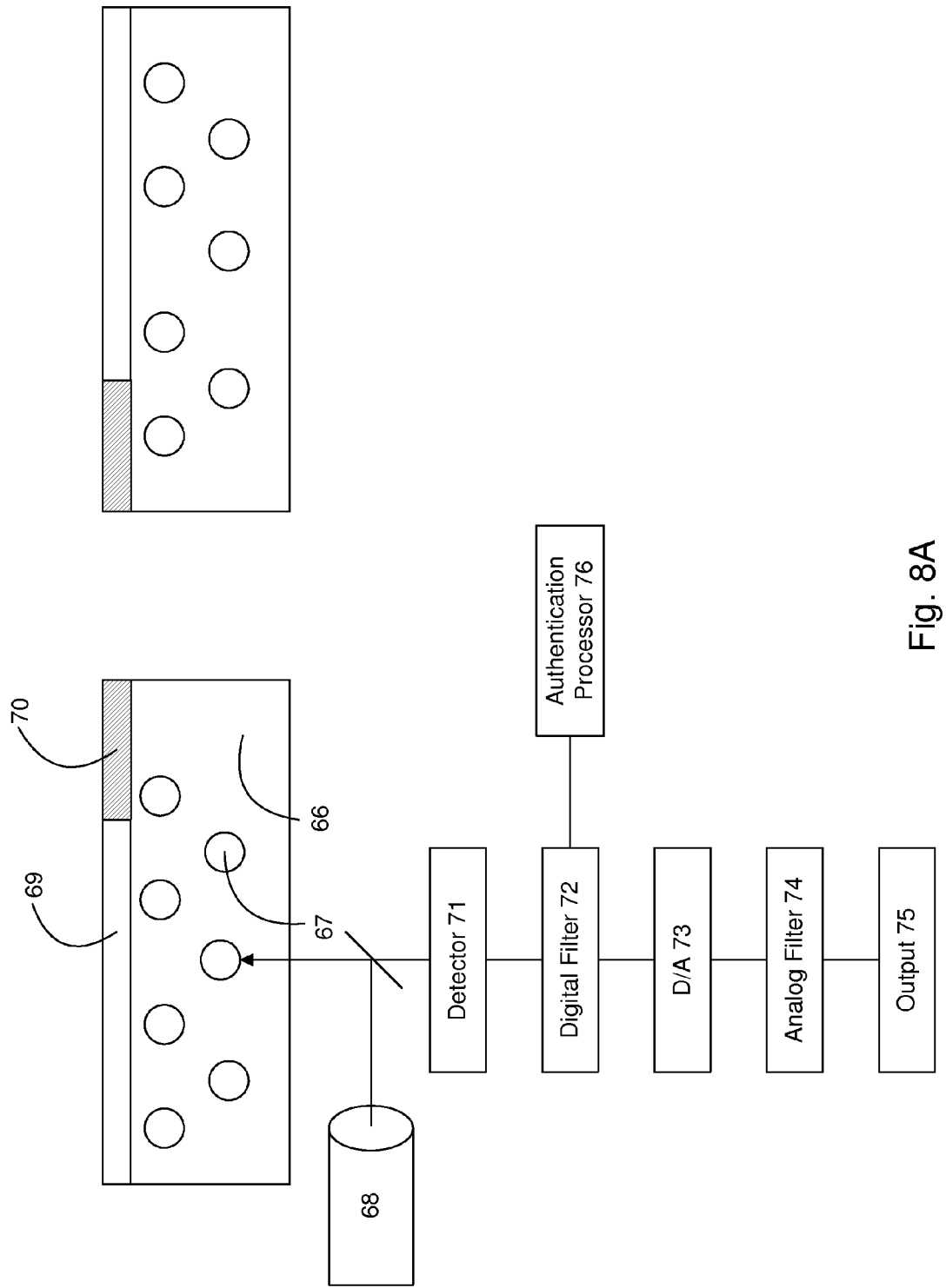
FIG. 8A is a schematic illustration of the authentication process relating to Compact Discs and Digital Video Disks.

FIG. 8A describes the process used to authenticate marked Compact Discs wherein a laser 68 is used to illuminate a Compact Disc 66 with an aluminized coating 69 and an exposed non-aluminized area of the disk has a bar code 70, so that an embedded defect 67 is illuminated, blocking normal reading of the data pattern on the disk, which is read by the detector 71, and then digitally filtered 72 and intercepted by an authentication processor 76. The data is also sent to a digital to analog converter (D/A) 73 and then to an analog filter 74 for output 75.

Figure 8B:
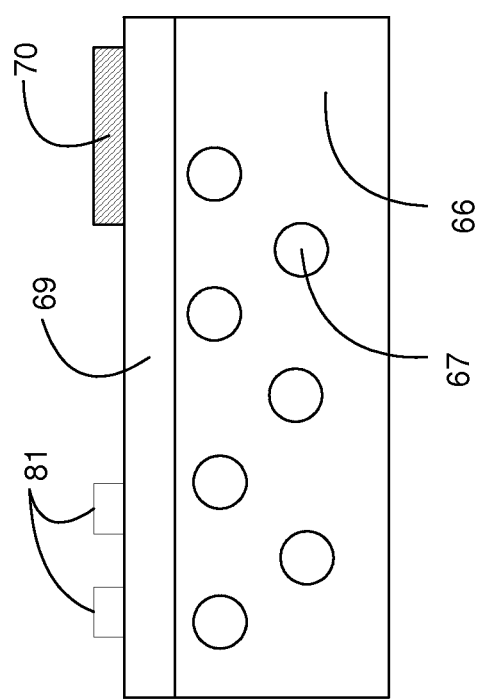
FIG. 8B shows the Compact Discs and Digital Video Disks of FIG. 8A with custom dye particles thereon.

FIG. 8B describes another embodiment of FIG. 8A whereby dye particles 81 are dispersed on top of the Compact Disc 66. Also shown are the original embedded defects 67, which may be, for example, microbubbles, the bar code 70, and the aluminum coating 69.

Figure 9:
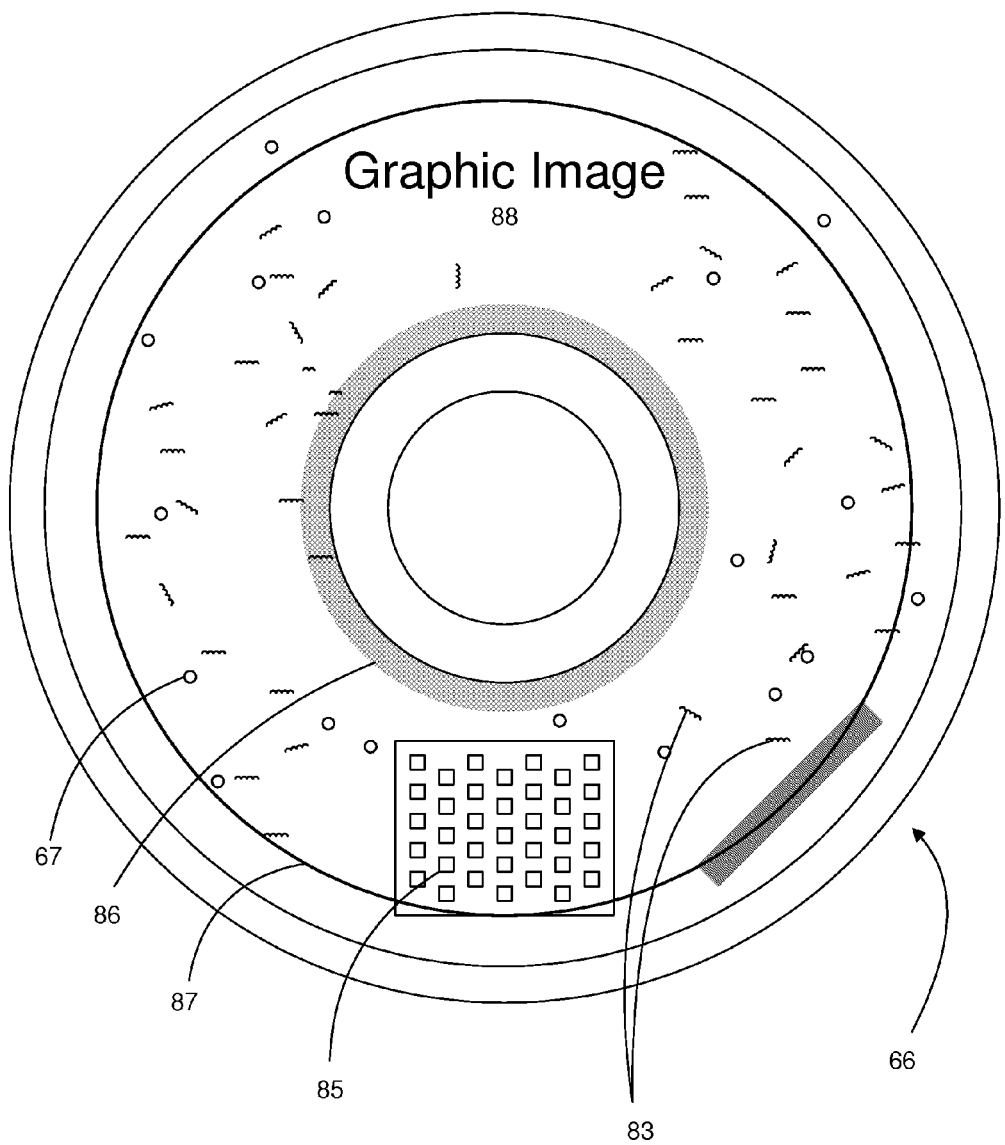
FIG. 9 is a top view of a Compact Discs and Digital Video Disk with several levels of security.

FIG. 9 shows a top view of the disk 66 showcased in FIGS. 8A and 8B with the graphic image 88 visible. Shown are the randomly spaced dichroic fibers 83 interspersed either within the Compact Disc 66 or on the surface, optionally in the advertising material. Also seen are the embedded defects 67 and the bar code 70 in a top view.

Figure 10:
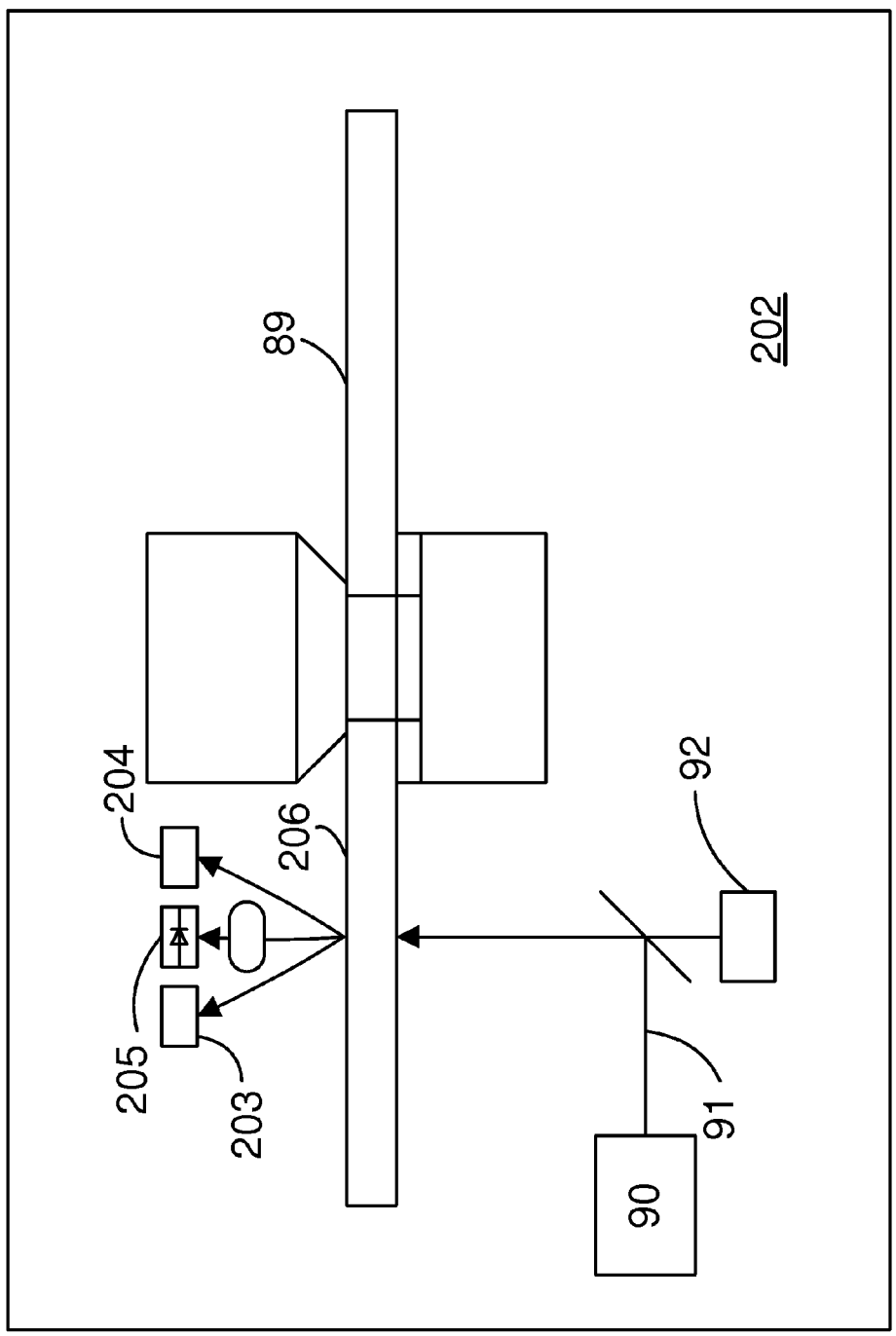
FIG. 10 is a Compact Discs and Digital Video Disk player containing and authenticating a Compact Discs and Digital Video Disks with a laser.

FIG. 10 shows a compact disk drive 202 with a disk 89, whose data pattern is read by a laser 90 and optical sensor 92. The top surface 206 of the disk 89 is read by a light emitting diode 205 and a pair of optical sensors 203, 204. One of the optical sensors detects 203 reflected light, while the other 204 detects fluorescent light (at a different wavelength than the illumination).

Figure 11:
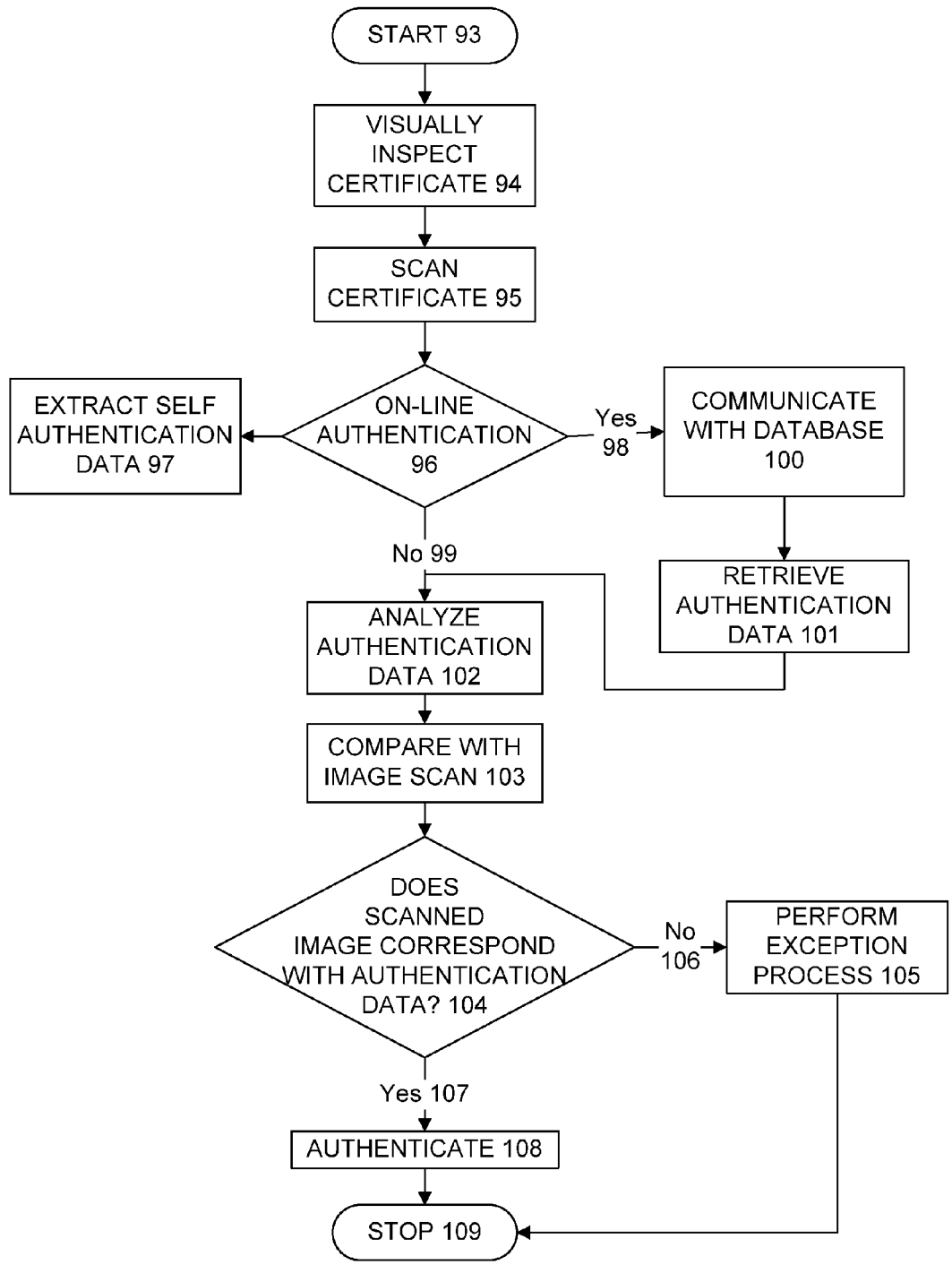
FIG. 11 is a schematic process illustration depicting the method of authentication either with or without on-line authentication.

FIG. 11 describes the process for certificate authentication starting 93 by first visually inspecting the certificate 94 to check for authenticity. Then the certificate is scanned 45 and put through an on-line authentication process 46 where self-authentication data is extracted 97. If on-line authentication is selected 98, then there is communication with the centralized database 100 which retrieves authentication data 101. If the authentication is off-line, the self-authentication data is extracted and processed locally. The authentication data is analyzed further 102 and then compared with the image scan 103. The system checks to verify if the scanned image corresponds with the authentication data. If not 106, an exception process is performed 105. If yes 107, then the article is authenticated 108.

Figure 12A:
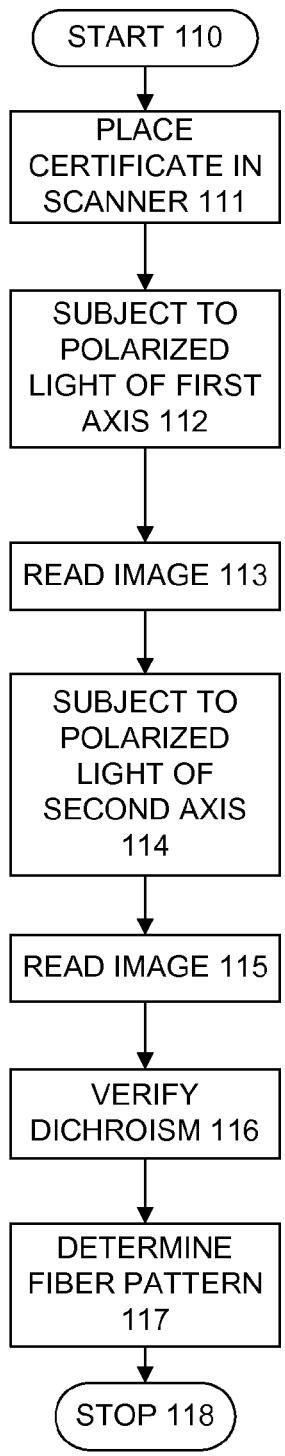
FIG. 12A shows a flow chart detailing method of determining the fiber pattern using two axes of inherent polarization of the fibers in a certificate.

FIG. 12A starts 110 with placing the certificate in the scanner 111. The certificate is subjected to polarized light of the first axis 112 and then the image is read 113. Again it is subject to polarized light of the second axis 114 and the image is read 115. The dichroism is verified 116 and the fiber pattern is thusly determined 117. The process then stops 118.

Figure 12B:
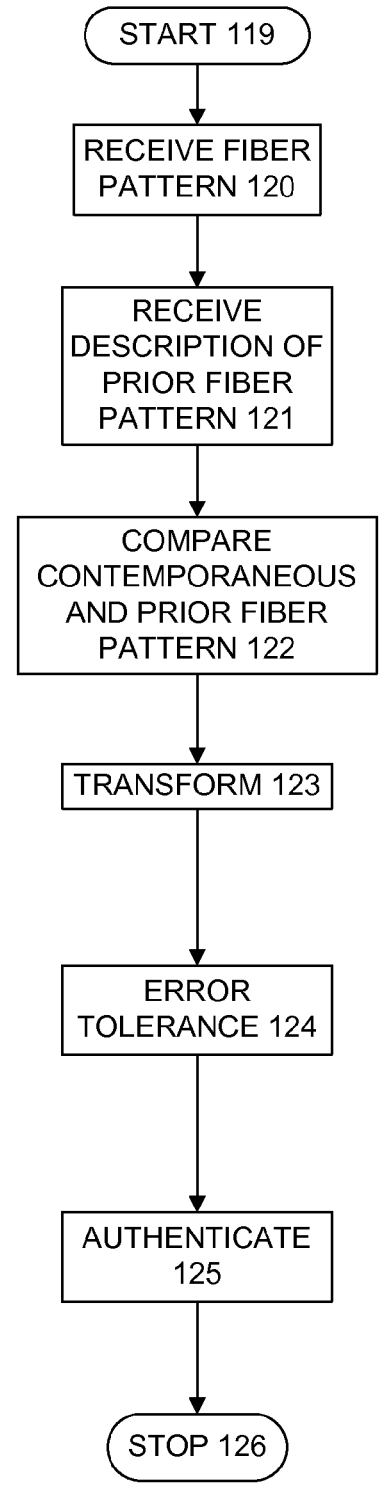
FIG. 12B shows a flow chart detailing a method of authentication.

FIG. 12B starts 119 with receipt of the fiber pattern 120, and then receipt of description of the prior fiber pattern 121. The contemporaneously read and previously determined fiber patterns are then compared 122, with transformation 123 to normalize the data. Likewise, the normalized data is permitted an error tolerance 124. Based on the error tolerance (which may be variable) the normalized data is authenticated 125. The process stops 126.

Figure 13A:
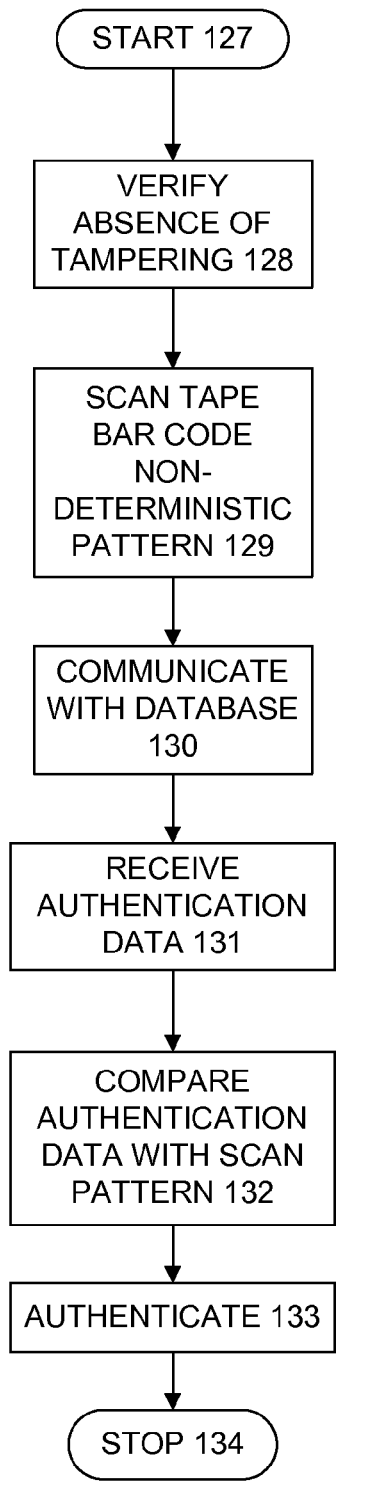
FIG. 13A shows a flow chart detailing a method of authentication relating to the authenticating tape of FIGS. 7A and 7B.

FIG. 13A starts 127 with the verification of the absence of tampering by looking (visual inspection) at the tape 128. The tape is scanned 129, to read a bar code and a non-deterministic pattern 129, and there is communication with the database 130. Then the authentication there system receives the authentication data 131, and a comparison between authentication data with the scan pattern 132 is performed. Based on the results of the comparison, the tape may be authenticated 133, and the process ends 134.

Figure 13B:
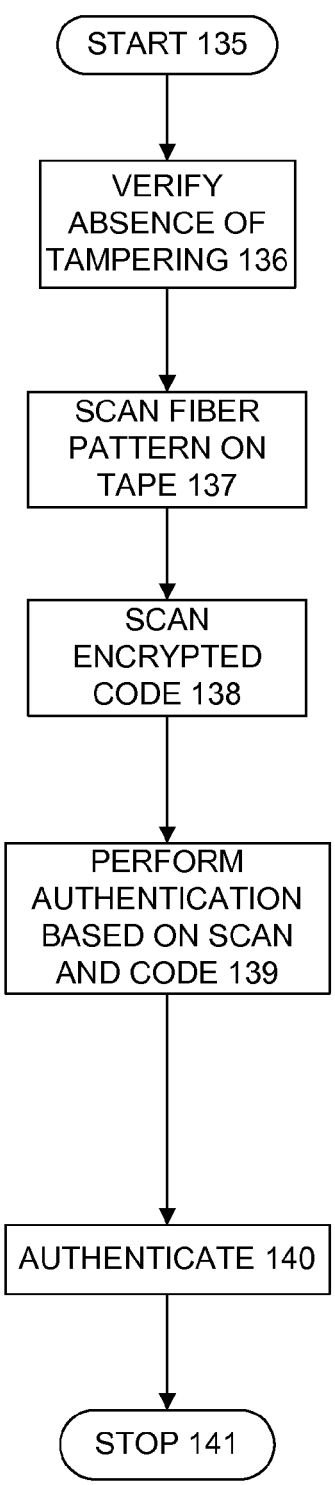
FIG. 13B shows a flow chart detailing a closed method of authentication for the tapes of FIGS. 7A and 7B.

FIG. 13B starts 135 with the verification of the absence of tampering 136 by looking at the tape, and both the fiber pattern on the tape 137 and then the encrypted code 138 are scanned. An authentication 139 is based on the fiber pattern scan and encrypted code. Based on the results of the authentication, an authenticate output 140 is selectively produced, and the process ends 141.

FIG. 14A shows a flow chart of a process for authenticating a compact disk or digital video disk. At the start 142 of the process, the compact disk is loaded into a disk drive 143. A custom imprinted code, located on a peripheral (inner or outer) band of the compact disk, is read 144. This may be read using the normal data read mechanism, which include a laser diode and photodetector, or from an upper surface using a specially provided sensor (in which case a peripheral location of the code would not be necessary).

The drive then, based on the code, seeks "defects" in the disk, at locations defined by the code. 145. The code, therefore, may include track and sector information for a set of defects, which may be limited in number to 5-16 defects. Preferably, the absolute number of defects on any disk is not intentionally made higher than that necessary for authentication. Using the disk read circuitry, the location of the expected defects is correlated with the existence of actual defects, to authenticate the disk 146. If defects are not found at the expected locations, or there are an insufficient number of identified defects, the disk authentication 146 fails.

Since the locations of the defects are encoded, it is possible to correct the output for the existence of the defects by filtering 147. The authentication process is then complete 148, and an authenticated disk may be played normally.

FIG. 14B provides an authentication method which does not employ the normal data laser to read a non-deterministic pattern, and thus does not rely on defects. At the start 149, the disk is loaded into the drive 150. On the top (non-data reading) surface of the disk, a custom code is imprinted. This code is read 151, for example by a one or more light emitting diode-photodiode pair. This code is, for example a bar code disposed circumferentially about a portion of the disk. A non-deterministic pattern is read 152 from the disk, which may be formed as a pattern of ink reflection, a pattern of fibers or ink spots, or the like, in line with the optical read path of the sensor. This optical sensor is not presently provided in known disk drives. The correspondence of the non-deterministic pattern and the read code is then verified 153. The dye spectral characteristics or dichroism of the non-deterministic elements are also verified 154 by optical techniques. Optionally, an on-line authentication procedure 155 may be employed, for example to verify a detailed pattern of fibers on the disk. If the non-deterministic pattern and physical attributes (dye and/or dichroism) correspond to an authentic disk signature, then the disk is authenticated 156, and the disk may be used normally at the end of the process 157. Otherwise, firmware within the drive may be employed to prevent normal usage.

Figure 15:
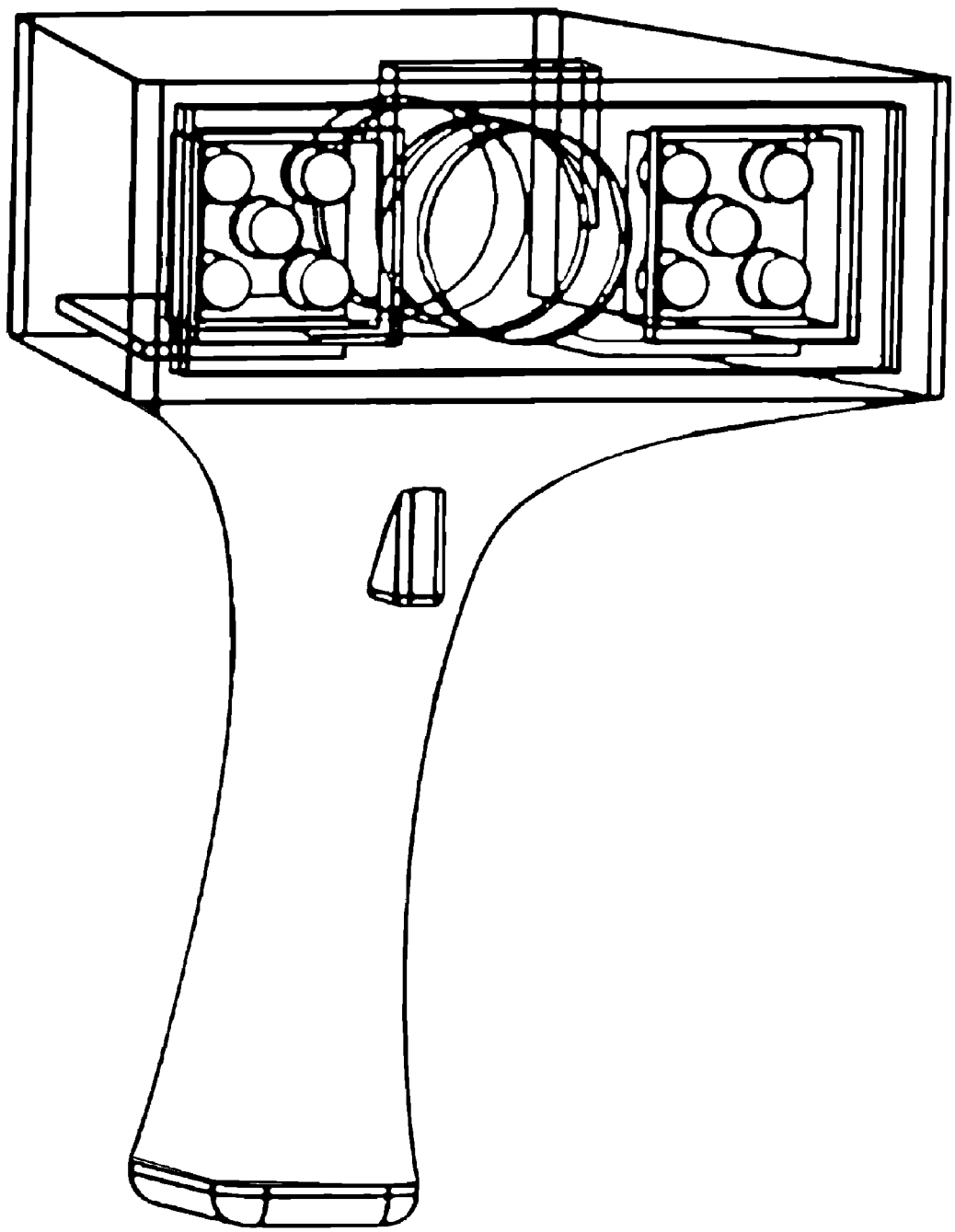
FIG. 15 shows a perspective view of a reader according to an embodiment of the invention.

As shown in FIG. 15, a perspective view of a reader according to an embodiment of the invention is shown. This embodiment provides a non-deterministic system and is inherently difficult, if not impossible to duplicate, and yet is machine-readable and the cost (both economically and algorithmically) of creation is tolerable. This scheme therefore presents a classic asymmetric problem, where the randomness is a normal result of a manufacturing process which does not control for a position and orientation of fibers or other elements in a bulk pulp, but in which a duplication of the result is extraordinarily difficult. The use of a physical authentication process for the elements preempts use of normal image duplication technologies, and in some cases permits human verification of authenticity before a machine is or need be employed. The randomness of the orientations and positions creates a stochastic system that effectively results in a different unique code for each substrate, which in some cases cannot be predicted, and in any case cannot be duplicated.

The conversion of the information to a machine-readable code or symbology (combining the digitized image of the anisotropic optical materials along with their two or three dimensional spatial relationships) is known as digiometry. Importantly, and uniquely, the random optical pattern technology is combinable and compatible with many other security features. In fact, data representing other security features including biometrics as well as electronic pedigree and other supply chain and inventory information can readily be combined with the digiometry to create a security system impervious to duplication, cloning or other aspects of forgery or counterfeiting. Thus, not only can the physical media of a document or object be authenticated, but also information or characteristics associated with the object itself.

To duplicate labels containing the fluorescent dichroic fibers, a counterfeiter would need to, among other things: duplicate the fluorescent dye used (to produce the same emission behavior at the selected detector wavelength); use fibers of the same general length and shape; and produce counterfeit label stock having the same general number of fibers per a given area of paper. Any attempt to counterfeit the fiber-containing label through a printing-based process would fail since printing would not reproduce the fibers' dichroic characteristics, and even matching the fluorescence would be difficult to achieve, especially if a custom dye or set of dyes is employed.

When a particular document, label or article is interrogated, the reader may determine the fibers' position and their dichroism, e.g., polarization angle. A still higher level of security and authentication occurs when the marked article is optically marked before it is circulated to record it optical characteristics including the polarization angle at a specified wavelength, its position, its absorption wavelength, the physical disposition of the fibers within the article. The combination of these parameters is very difficult to duplicate. This data, or a subset of the data, is formulated and then encoded using an encryption algorithm. The final element of security is providing by registering the information relating to the optical and spatial characteristics of the random patterns of the materials in a secure database that may be queried on demand by authorized users to enable matching of the information derived from the verification scan of the article.

During the imaging process, the scanned pattern on the article is captured and represented as an image projected on a surface. The printed code is also imaged, and captured by the processor. This information is then compared with the ideal image represented by the code printed on the article. A stochastic analysis is performed of the types and magnitudes of any deviations, as well as correlations of deviations from the ideal. The deviation pattern, as well as any other deviations from the encoded patterns, including the possibility of lost or obscured fibers, noise, environmental contamination with interfering substances, errors or interference in the original encoding process, etc., are then used to determine the likelihood that the article itself corresponds to the article that was originally encoded.

It is unnecessary to image and encode the entire or a substantial portion of the article. The entire article (document or label) can be subdivided into sectors or regions. Selectively defined by the end-user and defined by the software, the image capture can occur in a predetermined region. This further adds to the complexity of the decoding by a potential counterfeiter and makes the ability to circumvent the random pattern approach to authentication that much more robust.

Also, where the label itself is formed of dichroic fibers, a pattern may be formed on the fibers by photobleaching or annealing, using light or heat, respectively, for example from a laser. Thus, the absence of dichroism may then be determinative of a pattern thereon. Likewise, in a paper label with embedded dichroic fibers, a code may be provided by selectively bleaching or heating fibers within the label to alter their optical characteristics.

There are a number of optional approaches to creating random patterns of optically readable materials that do not require synthetic fibers or threads. For example, other optically reactive or optically responsive materials may be employed. For example, nanocrystalline materials, carbon nanotubes/fullerenes, dendrimers (organic nanoparticles), polyhedral silsesquioxanes (inorganic-organic hybrid nanoparticles), nano-intermediates and nanocomposites are among the alternative nanomaterials that are doped with fluorescent dyes. These materials, microscopic in size, will lend themselves to random dispersal in a range of substrates and materials in which either the processing temperatures or pressures are such that they would destroy or noticeably alter the optical characteristics of Nylon fluorescent dichroic fibers. In the case of nanoparticles, it is typically not efficient to image these at a molecular level, as might be required to determine orientation. Therefore, in one embodiment, a low concentration of nanoparticles is dispersed in a region of an article (or throughout the article), and the positions thereof determined, for example by a spatial pattern of optical properties. As with the fibers, the physical authenticity of the nanoparticles may be determined by secondary means particular to the particles. In order to preempt duplication by printing or lithographic methods, the nanoparticles may be covertly applied to the article, or if integrated into the bulk of an article, depth encoded (e.g., by an attenuation from a standard optical response at a surface). Other techniques may be available to distinguish nanoparticles provided during a normal manufacturing process and those added later using a different process.

The literature reports many fluorescent nanoparticles used for imaging applications including, semiconductor quantum dots, quantum wells, fluorescent silica nanoparticles, silica coated fluorescent polymer particles, dye-loaded latex nanobeads, fluorescent polystyrene particles and fluorochrome conjugated iron oxide nanoparticles. The use of fluorophors and fluorochromes may be used subject to the various constraints of manufacturing, normal use, counterfeit resistance, and authentication.

Finally, the use of fluorescently doped or tagged DNA encoded particles randomly dispersed in a substrate or product may also be utilized to identify a real versus a counterfeit product based on the matching of the random pattern distribution of these materials to a algorithmically derived code printed on the article. The DNA can be separately authenticated using a PCR or complementary binding process, selective restriction endonuclease triggered release of tag, or by other means. Indeed, a DNA sequence may also be used as an information carrier, in a scheme which would be most useful for small volume, high value, authentication scenarios.

Thus, a reduction in size of symbology (reduced size symbology, or RSS), the possibility of microscopic symbology being integrated with the nanomaterials is not out of the realm of possibility. On a simpler scale, the use of phosphorescent particles of like spectral characteristics, or in combinations of varying spectral characteristics, may be provided Beyond its robustness, and with or without database link, the anti-counterfeiting technology may be combinable with many other forms of security features, including biometrics, RFIDs, inks, color variations/layers, micro-printing, holograms, and others. The non-deterministic features may be overt or covert, and the preferred optical (though other types of physical authentication and position and/or orientation measurement techniques may be employed) and logical components can thus be applied to strengthen the security of other anti-counterfeiting technologies without interfering with their function.

Taking biometric techniques as an example, these can be strengthened for:

a. Authenticating the material from which an identification document was manufactured, optionally tying it to whatever specific biometric method is employed by the authorizing organization, or is targeted by a counterfeiter; or b. Rendering a photograph or other zone of an identification document tamper-evident; or c. Enhancing the means of tying one zone of a document to another, for example the front of a document to its back; or d. Any of the above in combination.

Consequently, for example, the system can help biometrics to overcome weaknesses in their ability to counter a theft of document components.

In a sense, the fiber or element pattern security feature can be thought of as a "biometric" of the document or object itself, because of its ability to tie different parts of a protected document and/or its features to one another, while imparting a unique machine-readable identity to every single document.

Further, as the random patterns of materials are "read" by a proprietary scan during manufacture of a label or component, the data allows for the creation of a unique digital and non-deterministic Electronic Pedigree. The Electronic Pedigree is then encrypted, and recorded as a code in association with the scanned zone. The Electronic Pedigree can coexist with any other data represented in or upon the same medium, be it deterministic or non-deterministic. The digital record of the materials need not be located close to the scanned reference zone of an article, and indeed may be stored remotely, and accessible for example through public networks such as the Internet or cellular data networks.

Because articles protected by the aforementioned technologies may be both "self-validating" and unique, the system can be augmented with databases, yet a database is not a system requirement. Thus the system may provide both overt and covert security features and a hierarchy of available data elements from rapid go/no-go to forensic. The multiple covert layers of security make them compatible with implementing operational security models. A considerable quantity of information can be incorporated into symbology printed during a protected document's manufacture or pre-issuance processing. This can go well beyond the imaging information required for authentication, and can be made available in layers to a hierarchy of law enforcement, forensic and investigative users. The information may also include biometric, biographic, geographic and/or other data.

As a consequence of the security information being both digital and unique to a given document, the system is ideally suited for use in conjunction with databases. By establishing real-time communication with a database by a given scanner or scanner hub, the date, time, location and result of a scan together with pre-recorded data on a given document or object can be linked with archival data for that document or its holder, and processed for effective trends analysis and monitoring.

Because documents and assets protected by the system are self-authenticating, prudent database design can entirely preclude a hacker or other thief from gaining knowledge about what is required for successful authentication, even with full database access.

A secure Internet connection to the scanner will naturally offer geographically unrestricted access to such a database in real time by the password hierarchy of anti-counterfeiting users. The system can also implement PIN access (or two- or more factor user authentication schemes, such as biometrics, cryptographic token codes, etc.) to selected data at the scanner itself. Even where a database and/or PIN access to selected data are utilized to promote the customer's security model, an important property of the security feature and scanner combination remains its additional ability to provide stand-alone authentication of each protected document or object.

The dichroic fibers or other authentication elements can be provided in or on an object in a number of different ways. It is amenable to application as a component in a coating, in a lamination, or it can be mixed in with the pulp during papermaking or a melt during polymer processing. This also enhances the ability of the system to mesh with other security features, as earlier herein described.

There have thus been shown and described novel anti-counterfeit articles and novel aspects of anti-counterfeit systems, as well as methods employing same, which fulfill all the objects and advantages sought therefore. Many changes, modifications, variations, combinations, sub-combinations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A method for making an object having a set of randomly dispersed non-photocopyable elements physically associated with the object authenticatable, comprising:
   determining an arrangement of the set of randomly dispersed non-photocopyable elements physically associated with the object by acquiring at least two different images of the elements;
   generating a cryptographically authenticated secure digital signature code from a cryptographic function, from which the arrangement of the set of randomly dispersed non-photocopyable elements physically associated with the object cannot be ascertained, but the identity of a subsequently measured arrangement of the set of randomly dispersed non-photocopyable elements physically associated with the object represented in the digital signature code acquired after the determining, with the determined arrangement is statistically verifiable based on at least a stochastic analysis of deviations of between the subsequently determined arrangement and the determined arrangement; and
   associating the digital signature code with the object.

2. The method according to claim 1, further comprising authenticating the object by:
   illuminating the set of elements;
   subsequently determining the arrangement after the associating;
   verifying a correspondence of subsequently determined arrangement and the determined arrangement represented by the digital signature code.

3. The method according to claim 1, wherein the at least two different images are obtained by illumination of the elements with different optical wavelengths.

4. The method according to claim 1, wherein the at least two different images are obtained by imaging through at least two optical filters having different optical wavelength transmission characteristics.

5. The method according to claim 1, wherein the at least two different images are obtained by different polarization states of a polarization-sensitive imaging system.

6. The method according to claim 1, wherein the at least two different images are obtained through at least two different states of an imaging process sensitive to an optical refraction characteristic of each of the elements.

7. The method according to claim 1, wherein the at least two different images are obtained at different times with respect to an optical illumination pulse.

8. The method according to claim 1, wherein verification of the subsequently determined arrangement based on the cryptographically authenticated secure digital signature code requires a cryptographic authentication key.

9. The method according to claim 1, wherein the set of randomly dispersed non-photocopyable elements and the associated digital signature code are disposed to be readable in a single image of the object.

10. The method according to claim 1, further comprising authenticating the object with a hand-held authentication device comprising at least one illuminator, at least one digital camera, an automated processor, a digital memory communicating with the automated processor, a power supply, and an authentication control interface.

11. A method for making an object having a set of randomly dispersed non-photocopyable elements physically associated with the object authenticatable, comprising:
   determining an arrangement of the set of randomly dispersed non-photocopyable elements physically associated with the object by acquiring at least two different images of the elements with at least one electronic imager;
   generating a cryptographically authenticated secure digital signature code from a cryptographic function using at least one automated processor, from which the arrangement of the set of randomly dispersed non-photocopyable elements physically associated with the object cannot be ascertained, but the identity of a subsequently measured arrangement of the set of randomly dispersed non-photocopyable elements physically associated with the object represented in the digital signature code acquired after the determining, with the determined arrangement being statistically verifiable based on at least a stochastic analysis of deviations of between the subsequently determined arrangement and the determined arrangement; and printing the digital signature code in association with the object.

12. The method according to claim 11, wherein the optical imager comprises a digital camera in a configuration adapted to read an optical pattern which is not representable as a CIE tristimulus value due to at least one of dichroism, fluorescence, phosphorescence, refraction, diffraction, lasing, and hyperspectral color characteristics.

13. The method according to claim 12, wherein the digital camera acquires a plurality of images respectively differing in at least an optical filtering, relative position with respect to the set of elements, time with respect to a time-varying illumination.

14. The method according to claim 11, wherein the at least one automated processor further generates a cryptographically authenticated one-way trap door function secure digital signature code from the cryptographic function.

15. The method according to claim 11, wherein the at least one automated processor further statistically verifies the identity of the subsequently measured arrangement represented in the digital signature code acquired after the determining with the determined arrangement, based on at least a stochastic analysis of deviations of between the subsequently determined arrangement and the determined arrangement.

16. The method according to claim 11, wherein the set of elements comprise fluorescent particles, further comprising illuminating the set of randomly dispersed non-photocopyable elements, with an optical illuminator, at a first wavelength, and acquiring the at least one image corresponding to a fluorescence, with the at least one optical imager at a second wavelength.

17. The method according to claim 11, wherein the at least two different images are obtained under at least one of different optical illumination conditions and different optical filtering conditions.

18. The method according to claim 11, wherein the at least two different images are obtained at different relative positions with respect to the elements.

19. The method according to claim 11, wherein the at least one electronic imager and the at least one automated processor are contained within a hand-held authentication device further comprising at least one illuminator, a digital memory communicating with the at least one automated processor, a power supply, and an authentication control interface.

20. A method for authenticating an object having a set of randomly dispersed non-photocopyable elements physically associated with the object, comprising:

determining an arrangement of the set of randomly dispersed non-photocopyable elements physically associated with the object by acquiring at least two different images of the elements;

reading a cryptographically authenticated secure digital signature cryptographic code physically associated with the object generated based on a cryptographic function and an arrangement of the set of randomly dispersed non-photocopyable elements physically associated with the object determined prior to the determining, from which the prior determined arrangement of the set of randomly dispersed non-photocopyable elements physically associated with the object cannot be ascertained;

determining, with at least one automated processor, an identity of the determined arrangement with the prior determined arrangement, based on at least a stochastic analysis of the determined arrangement and information available from the cryptographically authenticated secure digital signature cryptographic code.

* * * * *